(12) United States Patent
Greff et al.

(10) Patent No.: US 9,040,529 B2
(45) Date of Patent: May 26, 2015

(54) 4-PHENYLAMINO-PYRIMIDINE DERIVATIVES HAVING PROTEIN KINASE INHIBITOR ACTIVITY

(75) Inventors: Zoltán Greff, Budapest (HU); Zoltán Varga, Budapest (HU); György Kéri, Budapest (HU); Gábor Németh, Budapest (HU); László Örfi, Budapest (HU); Csaba Szántai Kis, Budapest (HU)

(73) Assignee: Vichem Chemie Kutató Kft., Budapest (HU)

( * ) Notice: Subject to any disclaimer, the term of this patent is extended or adjusted under 35 U.S.C. 154(b) by 144 days.

(21) Appl. No.: 13/517,120

(22) PCT Filed: Dec. 17, 2010

(86) PCT No.: PCT/HU2010/000145
§ 371 (c)(1),
(2), (4) Date: Jun. 21, 2012

(87) PCT Pub. No.: WO2011/077171
PCT Pub. Date: Jun. 30, 2011

(65) Prior Publication Data
US 2012/0258968 A1    Oct. 11, 2012

(30) Foreign Application Priority Data
Dec. 21, 2009   (HU) ..................................... 0900798

(51) Int. Cl.
*A61K 31/5377* (2006.01)
*C07D 239/42* (2006.01)
*C07D 401/04* (2006.01)
*C07D 403/04* (2006.01)
*C07D 403/14* (2006.01)
*C07D 409/14* (2006.01)

(52) U.S. Cl.
CPC ............ *C07D 239/42* (2013.01); *C07D 401/04* (2013.01); *C07D 403/04* (2013.01); *C07D 403/14* (2013.01); *C07D 409/14* (2013.01)

(58) Field of Classification Search
CPC .......................... C07D 239/42; A61K 31/5377
USPC .......... 514/234.5, 256; 544/122, 327
See application file for complete search history.

(56) References Cited

U.S. PATENT DOCUMENTS

| | | |
|---|---|---|
| 3,478,030 A | 11/1969 | Short |
| 3,950,525 A | 4/1976 | De Angelis et al. |
| 6,107,305 A | 8/2000 | Misra et al. |
| 6,114,365 A | 9/2000 | Pevarello et al. |
| 6,949,544 B2 | 9/2005 | Bethiel et al. |
| 8,673,950 B2 | 3/2014 | Nettekoven et al. |
| 2003/0008883 A1 | 1/2003 | Grant et al. |
| 2007/0191344 A1 | 8/2007 | Choidas et al. |
| 2008/0275063 A1 | 11/2008 | Schauerte et al. |

FOREIGN PATENT DOCUMENTS

| | | |
|---|---|---|
| WO | 2008/132138 A1 | 11/2008 |
| WO | 2012/059371 A1 | 5/2012 |

OTHER PUBLICATIONS

Hartung et al., Efficient microwave-assisted synthesis of highly functionalized pyrimidine derivatives; Tetrahedron 62(43); pp. 10055-10064, (2006).*
Norman et al.: "Novel Vanilloid Receptor-1 Antagonists: 1. Conformationally Restricted Analogues of trans-Cinnamides", J. Med. Chem., 2007, vol. 50, pp. 3497-3514.
Steele et al.: "Identification of a small molecule beta-secretase inhibitor that binds without catalytic asparate engagement", Bioorganic & Medicinal Chemistry Letters, 2009, vol. 19, pp. 17-20.
Doherty et al.: "4-Aminopyrimidine tetrahydronaphthols: A series of novel vanilloid receptor-1 antagonists with improved solubility properties", Bioorganic & Medicinal Chemistry Letters, 2008, vol. 18, pp. 1830-1834.

* cited by examiner

*Primary Examiner* — James O. Wilson
*Assistant Examiner* — Ebenezer O Sackey
(74) *Attorney, Agent, or Firm* — Jason D. Voight

(57) ABSTRACT

The invention relates compounds of general formula (I) and pharmaceutically acceptable salts and solvates thereof wherein
  $R^1$ is halogen, vinylene-aryl, substituted aryl, heteroaryl or a benzo[1,3]dioxolil group,
  W is a group of formula —NH—$SO_2$—$R_2$ or heteroaryl group or $NHR^3$ group where $R^3$ is hydrogen or heteroaryl; and n is 1, 2, 3 or 4.
Furthermore, the present invention is directed to pharmaceutical composition containing at least one compound of general formula (I) and/or pharmaceutically acceptable salts or solvates thereof and for the use of them for the preparation of pharmaceutical compositions for the prophylaxis and/or the treatment of protein kinase related, especially CDK9-related diseases e.g. cell proliferative disease, infectious disease, pain, cardiovascular disease and inflammation.

9 Claims, No Drawings

4-PHENYLAMINO-PYRIMIDINE DERIVATIVES HAVING PROTEIN KINASE INHIBITOR ACTIVITY

This is the National Stage of International Application PCT/HU2010/000145, filed Dec. 17, 2010.

FIELD OF THE INVENTION

The present invention relates to 4,6-disubstituted aminopyrimidines and pharmaceutically acceptable salts and solvates thereof, the use of these derivatives as pharmaceutically active agents, in particular for the prophylaxis and/or the treatment of protein kinase related, especially CDK9-related diseases e.g. cell proliferative disease, infectious disease, pain, cardiovascular disease and inflammation. Furthermore, the present invention is directed towards pharmaceutical composition containing at least one of the methylenesulfone or methylenesulfonamide derivatives of 4,6-disubstituted aminopyrimidines and/or pharmaceutically acceptable salts or solvates thereof and for the use of the compounds according to the invention for the preparation of pharmaceutical compositions for the prophylaxis and/or treatment of the above diseases.

BACKGROUND OF THE INVENTION

Protein kinases are dedicated to transfer phosphate group from ATP to one or more OH groups of a substrate protein. In this process they play catalytic role in phosphorylation reactions in living cells. Phosphorylation is the mode of information transmission on biomolecular level and can regulate the activity of certain proteins, which are tipically other protein kinases. There are about 1000 protein kinases known. There are receptor protein kinases, which are located in cellular membranes and non-receptor protein kinases, which are located in the cell plasm. We speak about tyrosine protein kinases when one can phosphorylate tyrosine OH and serine-threonine protein kinases when one can phosphorylate serine or threonine OH group. CDKs are non-receptor serine-threonine protein kinases that require cycline for their activity (Cycline Dependent protein Kinases).

One of the most important and fundamental processes in biology is the division of cells during the cell cycle. This process ensures the controlled production of subsequent generations of cells with defined biological function. It is a highly regulated phenomenon and responds to a diverse set of cellular signals both within the cell and from external sources. Cyclin dependent kinases (CDKs) play a key role in regulating the cell cycle machinery. These complexes consist of two components: a catalytic subunit (the kinase) and a regulatory subunit (the cyclin). To date, thirteen kinase subunits have been identified in humans (Chen et al., Biochem. Biophys. Res. Commun. 2007, 354, 735-40; S. Mani et al., Exp. Opin. Invest. Drugs 2000, 9(8), 1849-1870, J. C. Sergere et al., Biochem. Biophys. Res. Commun. 2000, 276, 271-277, D. Hu et al, J. Biochem. Chem. 2003, 278(10), 8623-8629).

It is known that CDKs play a role in the regulation of cellular proliferation. Therefore, CDK inhibitors could be useful in the treatment of cell proliferative disorders such as cancer, neuro-fibromatosis, psoriasis, fungal infections, endotoxic shock, transplantation rejection, vascular smooth cell proliferation associated with artherosclerosis, pulmonary fibrosis, arthritis, glomerulonephritis and post-surgical stenosis and restenosis (U.S. Pat. No. 6,114,365).

CDKs are also known to play a role in apoptosis. Therefore CDK inhibitors could be useful in the treatment of cancer; autoimmune diseases, for example systemic lupus, erythematosus, autoimmune mediated glomerulonephritis, rheumatoid arthritis, psoriasis, inflammatory bowel disease, and autoimmune diabetes; neurodegenerative diseases for example Alzheimer's disease, AIDS-related dementia, Parkinson's disease, amyotrophic lateral sclerosis, retinitis pigmentosa, spinal muscular atrophy and cerebellar degeneration; myelodysplastic syndromes, aplastic anemia, ischemic injury associated with myocardial infarctions, stroke and reperfusion injury, arrhythmia, atherosclerosis, toxin-induced or alcohol related liver diseases; hematological diseases, for example, chronic anemia and aplastic anemia; degenerative diseases of the musculoskeletal system, for example, osteoporosis and arthritis, cystic fibrosis, multiple sclerosis, kidney diseases and cancer pain and for the treatment of cardiovascular diseases (U.S. Pat. No. 6,107,305 and WO 02/100401).

Further it is known that CDK inhibitors could be used for the treatment of virally induced infectious diseases, such as EBV, HBV, HCV and HIV (WO 02/100401). Recently, it was described, that HIV-1 replication could be affected by inhibiting CDKs (C. de la Fuenta, Current HIV research, 2003, 1(2), 131-152; Y. K. Kim et al., Molecular and Cellular Biology, 2002, 22(13), 4622-4637). Especially CDK9 is reported to be essential for the HIV-1 replication (H. S. Mancebo et al, Genes Dev. 1997, 11(20): 2633-44, O. Flores et al., Proc. Natl. Acad. Sci. USA. 1999, 96(13):7208-13). CDK9 is also involved in the development of pain: both cyclin T1 and CDK9 stimulate the basal promoter activity of TNFa, a pro-inflammatory cytokine and pain mediator that controls expression of inflammatory genetic networks. For mediation of cellular TNF receptor responses, the nuclear factor-KB (NFκB) pathway is crucial. TNFa triggers its recruitment to cytokine genes while NFκB interacts with the p-TEFb complex for stimulation of gene transcription (Barboric M. et al., NFκB Binds P-TEFb to Stimulate Transcriptional Elongation by RNA Polymerase II. Molecular Cell, 2001, Vol. 8, 327-337).

Additionally, it has been shown that CDK9 is a binding partner of TRAF2, a member of the TNFa receptor complex (MacLachlan T. K. et al., Binding of CDK9 to TRAF2. J. Cell Biochem., 1998, 71(4), 467-478), while GP130, a subunit of the pro-inflammatory IL6 receptor complex has recently been identified as another potential binding partner of CDK9 (Falco G. D. et al., CDK9, a member of the cdc2-like family of kinases, binds to gp130, the receptor of the IL-6 family of cytokines. Oncogene, 2002, 21(49), 7464-7470). As a key player in TNFa and interleukin signaling as well as NFκB mediated expression of several genes (e.g. cytokines as pain mediators), CDK9 can thus be considered as a central target for the treatment of inflammatory pain.

There also exists a strong link between CDK9 and caridac hypertrophy (reviewed in Sano & Schneider, Circulation Research, 2004, 95, 867) and inhibitors of CDK9 are expected to be effective in the treatment of cardiovascular diseases, such as caridac hypertrophy.

Most of the known CDK inhibitors, such as olomoucine, roscovitine (CYC202), purvalanols, indolinones, paullones and 7-hydroxy-staurosporine are focusing on the inhibiton of CDK1 and CDK2 with the goal of antitumor activity (Current Opinion in Pharmacalogy, 2003, 3, 1-9). A summary of the known CDK inhibitors is given by M. Huwe et al. (A. Huwe et al., Angew Chem Int Ed Engl. 2003; 42(19): 2122-38). Flavopiridol is described as a low-molecular, but unselective inhibitor of CDKs, including CDK9 (W. Filgueira de Azevedo et al., Biochem. and Biophys. Res. Commun. 2002, 293(1), 566-571). Other compounds that were shown to inhibit CDKs are staurosporine, fascaplysin and hymenialdisine.

The use of 4-aminopyrimidine derivatives as neuroprotective agents is described in WO 02/12198. These compounds generally contain as a basic residue a substituted amine in para position of the anilino part of the molecule and it is stated that these compounds did not inhibit MEK1/2 kinase activity in P19 neurons. U.S. Pat. No. 3,950,525 describes the use of 4-amino-6-aryl-pyrimidines as platelet aggregation inhibitors and bronchodilators. U.S. Pat. No. 3,478,030 describes the synthesis of benzamide substituted anilino aminopyrimidine derivatives. These compounds are used as potent dilators of coronary arteries. WO 02/79197 describes the use of aryl-substituted 2-aminopyrimidine derivatives as protein kinase inhibitors, for example as inhibitor of JNK, GSK-3, Src, Lck or CDK2. Certain 4,6-disubstituted aminopyrimidines are described in WO 05/026129. WO 05/026129 describes derivatives which are useful as pharmaceutically active agents, especially for the prophylaxis and/or treatment of infectious diseases, including opportunistic diseases, prion diseases, immunological diseases, autoimmune diseases, bipolar and clinical disorders, cardiovascular diseases, cell proliferative diseases, diabetes, inflammation, transplant rejections, erectile dysfunction, neurodegenerative diseases and stroke. However, the 4,6-disubstituted aminopyrimidines described in WO 05/026129 are structurally different to those described in the present application.

WO 06/125616 describes the use of CDK inhibitors, including CDK9 inhibitors, such as the 4,6-disubstituted aminopyrimidines disclosed in WO 05/026129, for the treatment of pain and inflammatory diseases.

There is a high unmet medical need to develop CDK inhibitors, useful in treating various medical conditions or diseases associated with CDK activation, in particular those conditions or diseases concerning CDK9 kinase activity, which is associated with cell proliferative disease, infectious disease, pain, cardiovascular disease and inflammation.

Compounds having similar structure are claimed in WO 2005/026129, WO 2008/132138 and US 2008/0275063 but there is no alkylene chain between the methylenesulfone or methylenesulfonamide group and the aryl moiety in the disclosed compounds.

In one aspect of the present invention, the compounds of the present invention or pharmaceutically acceptable salts and solvates thereof can be used as an inhibitor for a protein kinase, preferably as an inhibitor for a cellular protein kinase.

In a particular embodiment of these aspects said cellular protein kinase is a cyclin-dependent protein kinase (CDK). The cyclin-dependent protein kinase can be selected from the group comprising: CDK1, CDK2, CDK3, CDK4, CDK5, CDK6, CDK7, CDK8, CDK9, CDK10, CDK11, CDK12, CDK13, CrkRS (Crk7, CDC2-related protein kinase 7), CDKL1 (cyclin-dependent kinase-like 1); KKIALRE, CDKL2 (cyclin-dependent kinase-like 2), KKIAMRE, CDKL3 (cyclin-dependent kinase-like 3), NKIAMRE, CDKL4, similar to cyclin-dependent kinase-like 1, CDC2L1 (cell division cycle 2-like 1), PITSLRE B, CDC2L1 (cell division cycle 2-like 1), PITSLRE A, CDC2L5 (cell division cycle 2-like 5), PCTK1 (PCTAIRE protein kinase 1), PCTK2 (PCTAIRE protein kinase 2), PCTK3 (PCTAIRE protein kinase 3) or PFTK1 (PFTAIRE protein kinase 1). In particular such embodiments, said cyclin-dependent protein kinase is CDK9.

Although only CDK9 inhibitory effect is proved, inhibition of other CDKs can be expected as there are close relationship amongst cyclin dependent kinases. It can be assumed by a skilled person that other kinases also can be inhibited by the compounds of this invention because of the highly conserved ATP binding site which is presented in all protein kinases. Vast majority of small molecule inhibitors block kinases by binding to the ATP binding site, so these inhibitors have a general inhibitory effect on protein kinases (including CDKs, too, of course).

According to the current state of the art multiple kinase inhibitors are considered to be better to develop in contrast to selective ones, as they could block alternative signaling pathways and this way they show enchanced cellular and in vivo effect. However, selective inhibition of CDK9 can also be fruitful especially in the treatment of HIV infections. Unexpected side effect can be avoided by inhibiting only one key kinase.

With respect to the highly conserved ATP binding site which is presented in all protein kinases it is a well-based assumption that the compounds according to the invention have a general protein kinase inhibitory, especially CDK inhibitory effect.

SUMMARY OF THE INVENTION

It is an object of the present invention to provide compounds of general formula (I) and pharmaceutically acceptable salts and solvates thereof having protein kinase inhibitor, preferably cycline dependent protein kinase (CDK) inhibitor activity which can be used as pharmaceutically active agents, in particular for prophylaxis and/or treatment of one or more disease or medical condition selected from: cell proliferative disease, such as cancer; infectious disease, such as retroviral infectious disease, including HIV; pain, such as inflammatory pain and neuropathic pain; cardiovascular disease, such as cardiac hypertrophy; and inflammation, methods to treat said disease, as well as compositions comprising at least one of those compounds and/or pharmaceutically acceptable salts thereof as pharmaceutically active ingredients. The invention also relates to the use of the compounds of general formula (I) and pharmaceutically acceptable salts thereof for the preparation of a pharmaceutical composition for the prophylaxis and/or treatment of the above diseases.

Further advantageous features, aspects and details of the invention are evident from the, the description, the examples and the drawings and the claims.

According to the first aspect of the invention it relates to novel 4,6-disubstituted aminopyrimidine compounds of general formula (I) and pharmaceutically acceptable salts and solvates thereof

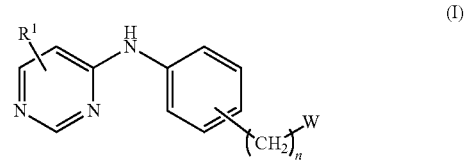

wherein
$R^1$ is halogen;
   vinylene-aryl;
   aryl, which may be substituted with one or more substituent selected from the following group:
      alkoxy, which is substituted in some embodiments with one or more halogen or with aryl, which can be further substituted in some embodiments with one or more halogen;

halogen,
alkyl, which is optionally substituted with one or more halogen or alkoxy, preferably with halogen,
alkylaryloxy, which may be substituted with alkoxy, which is optionally substituted with one or more halogen,
aminocarbonyl,
amino, which is optionally substituted with one or two alkyl,
alkylthio,
alkylsulfinyl or alkylsulfonyl,
aryloxy,
hydroxyl;
group of formula (a)

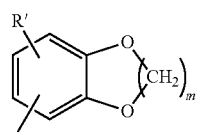

wherein m is 1, 2 or 3, preferably 1, and R' is hydrogen, halogen, alkyl or alkoxy;
heteroaryl;
W is a
group of formula (b)

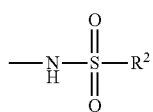

wherein $R^2$ stands for
alkyl, alkoxy or aryl, which groups are optionally substituted with one or more
halogen,
heteroaryl,
benzyl, which is optionally substituted with one or more halogen, alkyl or alkoxy,
amino, which is optionally substituted with one or two alkyl;
heteroaryl group, which is optionally substituted with a $(CH_2)_k$-heterocycloalkyl group, where k is 0, 1, 2 or 3;
NH—$R^3$, wherein $R^3$ is hydrogen, alkyl, alkoxy, aryl, aryloxy, heteroaryl, heteroaryloxy, aminoalkyl, aminoaryl or aminoheteroaryl; and
n is 1, 2, 3 or 4.

In particular embodiments of the invention, the compound of general formula (I) is selected from the following group:

Example 1: N-[3-(6-Chloro-pyrimidin-4-ylamino)-benzyl]-methanesulfonamide
Example 2: N-{3-[6-(2-Benzyloxy-phenyl)-pyrimidin-4-ylamino]-benzyl}-methanesulfonamide
Example 3: N-[3-(6-Styryl-pyrimidin-4-ylamino)-benzyl]-methanesulfonamide
Example 4: N-{3-[6-(2-Phenoxy-phenyl)-pyrimidin-4-ylamino]-benzyl}-methanesulfonamide
Example 5: N-{3-[6-(2-Ethoxy-phenyl)-pyrimidin-4-ylamino]-benzyl}-methanesulfonamide
Example 6: N-{3-[6-(2-Methoxy-phenyl)-pyrimidin-4-ylamino]-benzyl}-methanesulfonamide
Example 7: N-{3-[6-(4-Fluoro-2-methoxy-phenyl)-pyrimidin-4-ylamino]-benzyl}-methanesulfonamide
Example 8: N-{3-[6-(2-Isopropoxy-phenyl)-pyrimidin-4-ylamino]-benzyl}-methanesulfonamide
Example 9: N-{3-[6-(5-Fluoro-2-methoxy-phenyl)-pyrimidin-4-ylamino]-benzyl}-methanesulfonamide
Example 10: N-(3-{6-[2-(4-Fluoro-benzyloxy)-phenyl]-pyrimidin-4-ylamino}-benzyl)-methanesulfonamide
Example 11: N-[3-(6-o-Tolyl-pyrimidin-4-ylamino)-benzyl]-methanesulfonamide
Example 12: N-{3-[6-(2-Ethyl-phenyl)-pyrimidin-4-ylamino]-benzyl}-methanesulfonamide
Example 13: N-{3-[6-(2-Fluoro-6-methoxy-phenyl)-pyrimidin-4-ylamino]-benzyl}-methanesulfonamide
Example 14: N-{3-[6-(4-Fluoro-2-isopropoxy-phenyl)-pyrimidin-4-ylamino]-benzyl}-methanesulfonamide
Example 15: N-{3-[6-(2-Trifluoromethoxy-phenyl)-pyrimidin-4-ylamino]-benzyl}-methanesulfonamide
Example 16: N-{3-[6-(2-Fluoro-phenyl)-pyrimidin-4-ylamino]-benzyl}-methanesulfonamide
Example 17: N-{3-[6-(2,4-Difluoro-phenyl)-pyrimidin-4-ylamino]-benzyl}-methanesulfonamide
Example 18: N-{3-[6-(2-Trifluoromethyl-phenyl)-pyrimidin-4-ylamino]-benzyl}-methanesulfonamide
Example 19: N-{3-[6-(4-Methoxy-phenyl)-pyrimidin-4-ylamino]-benzyl}-methanesulfonamide
Example 20: 3-{6-[3-(Methanesulfonylamino-methyl)-phenylamino]-pyrimidin-4-yl}-benzamide
Example 21: N-[3-(6-Phenyl-pyrimidin-4-ylamino)-benzyl]-methanesulfonamide
Example 22: N-{3-[6-(3-Amino-phenyl)-pyrimidin-4-ylamino]-benzyl}-methanesulfonamide
Example 23: N-{3-[6-(2,3-Dimethoxy-phenyl)-pyrimidin-4-ylamino]-benzyl}-methanesulfonamide
Example 24: N-{3-[6-(2,4-Dimethoxy-phenyl)-pyrimidin-4-ylamino]-benzyl}-methanesulfonamide
Example 25: N-{3-[6-(4-Chloro-2-methoxy-phenyl)-pyrimidin-4-ylamino]-benzyl}-methanesulfonamide
Example 26: N-{3-[6-(2-Methoxy-5-methyl-phenyl)-pyrimidin-4-ylamino]-benzyl}-methanesulfonamide
Example 27: N-[3-(6-Benzo[1,3]dioxol-4-yl-pyrimidin-4-ylamino)-benzyl]-methanesulfonamide
Example 28: N-{3-[6-(2-Methylsulfanyl-phenyl)-pyrimidin-4-ylamino]-benzyl}-methanesulfonamide
Example 29: N-{3-[6-(2-Methanesulfinyl-phenyl)-pyrimidin-4-ylamino]-benzyl}-methanesulfonamide
Example 30: N-(3-{6-[2-(4-Trifluoromethoxy-phenoxymethyl)-phenyl]-pyrimidin-4-ylamino}-benzyl)-methanesulfonamide
Example 31: N-{3-[6-(2-Propoxy-phenyl)-pyrimidin-4-ylamino]-benzyl}-methanesulfonamide
Example 32: N-{3-[6-(1H-Pyrazol-4-yl)-pyrimidin-4-ylamino]-benzyl}-methanesulfonamide
Example 33: N-[4-(6-Chloro-pyrimidin-4-ylamino)-benzyl]-methanesulfonamide
Example 34: N-{4-[6-(2-Methoxy-phenyl)-pyrimidin-4-ylamino]-benzyl}-methanesulfonamide
Example 35: N-{4-[6-(2-Benzyloxy-phenyl)-pyrimidin-4-ylamino]-benzyl}-methanesulfonamide
Example 36: N-(4-{6-[2-(4-Fluoro-benzyloxy)-phenyl]-pyrimidin-4-ylamino}-benzyl)-methanesulfonamide
Example 37: N-{4-[6-(2-Ethoxy-phenyl)-pyrimidin-4-ylamino]-benzyl}-methanesulfonamide
Example 38: N-{4-[6-(5-Fluoro-2-methoxy-phenyl)-pyrimidin-4-ylamino]-benzyl}-methanesulfonamide
Example 39: N-{4-[6-(4-Fluoro-2-methoxy-phenyl)-pyrimidin-4-ylamino]-benzyl}-methanesulfonamide Example 40: N-{4-[6-(2-Phenoxy-phenyl)-pyrimidin-4-ylamino]-benzyl}-methanesulfonamide
Example 41: N-{4-[6-(2-Methylsulfanyl-phenyl)-pyrimidin-4-ylamino]-benzyl}-methanesulfonamide
Example 42: N-{4-[6-(2,4-Difluoro-phenyl)-pyrimidin-4-ylamino]-benzyl}-methanesulfonamide
Example 43: N-{4-[6-(2-Trifluoromethyl-phenyl)-pyrimidin-4-ylamino]-benzyl}-methanesulfonamide
Example 44: N-{4-[6-(2-Fluoro-phenyl)-pyrimidin-4-ylamino]-benzyl}-methanesulfonamide
Example 45: N-[4-(6-Phenyl-pyrimidin-4-ylamino)-benzyl]-methanesulfonamide
Example 46: N-{4-[6-(3-Amino-phenyl)-pyrimidin-4-ylamino]-benzyl}-methanesulfonamide hydrochloride
Example 47: N-{4-[6-(3-Methoxy-phenyl)-pyrimidin-4-ylamino]-benzyl}-methanesulfonamide
Example 48: N-{4-[6-(4-Fluoro-2-isopropoxy-phenyl)-pyrimidin-4-ylamino]-benzyl}-methanesulfonamide
Example 49: N-(4-{6-[2-(3-Fluoro-benzyloxy)-phenyl]-pyrimidin-4-ylamino}-benzyl)-methanesulfonamide
Example 50: N-(4-{6-[2-(4-Methoxy-benzyloxy)-phenyl]-pyrimidin-4-ylamino}-benzyl)-methanesulfonamide
Example 51: N-{4-[6-(2-Isobutoxy-phenyl)-pyrimidin-4-ylamino]-benzyl}-methanesulfonamide
Example 52: N-[4-(6-Pyridin-3-yl-pyrimidin-4-ylamino)-benzyl]-methanesulfonamide
Example 53: N-{4-[6-(2-Propoxy-phenyl)-pyrimidin-4-ylamino]-benzyl}-methanesulfonamide
Example 54: N-{4-[6-(4-Chloro-2-methoxy-phenyl)-pyrimidin-4-ylamino]-benzyl}-methanesulfonamide
Example 55: N-{4-[6-(2,3-Dimethoxy-phenyl)-pyrimidin-4-ylamino]-benzyl}-methanesulfonamide
Example 56: N-{4-[6-(2-Isopropoxy-phenyl)-pyrimidin-4-ylamino]-benzyl}-methanesulfonamide
Example 57: N-{4-[6-(4-Methoxy-phenyl)-pyrimidin-4-ylamino]-benzyl}-methanesulfonamide
Example 58: N-{4-[6-(1H-Pyrazol-4-yl)-pyrimidin-4-ylamino]-benzyl}-methanesulfonamide
Example 59: (1H-Benzoimidazol-2-yl)-[3-(6-chloro-pyrimidin-4-ylamino)-benzyl]-amine
Example 60: (1H-Benzoimidazol-2-yl)-{3-[6-(2-methoxy-phenyl)-pyrimidin-4-ylamino]-benzyl}-amine
Example 61: (1H-Benzoimidazol-2-yl)-{3-[6-(4-fluoro-2-methoxy-phenyl)-pyrimidin-4-ylamino]-benzyl}-amine
Example 62: (1H-Benzoimidazol-2-yl)-{3-[6-(5-fluoro-2-methoxy-phenyl)-pyrimidin-4-ylamino]-benzyl}-amine
Example 63: (3-Benzoimidazol-1-ylmethyl-phenyl)-(6-chloro-pyrimidin-4-yl)-amine
Example 64: (3-Benzoimidazol-1-ylmethyl-phenyl)-[6-(2-methoxy-phenyl)-pyrimidin-4-yl]-amine
Example 65: (3-Benzoimidazol-1-ylmethyl-phenyl)-[6-(4-fluoro-2-methoxy-phenyl)-pyrimidin-4-yl]-amine
Example 66: (3-Benzoimidazol-1-ylmethyl-phenyl)-[6-(5-fluoro-2-methoxy-phenyl)-pyrimidin-4-yl]-amine
Example 67: 2-[3-(6-Chloro-pyrimidin-4-ylamino)-benzyl]-isoindole-1,3-dione
Example 68: 2-{3-[6-(2-Methoxy-phenyl)-pyrimidin-4-ylamino]-benzyl}-isoindole-1,3-dione
Example 69: (3-Aminomethyl-phenyl)-[6-(2-methoxy-phenyl)-pyrimidin-4-yl]-amine hydrochloride
Example 70: 2,6-Dichloro-N-{3-[6-(2-methoxy-phenyl)-pyrimidin-4-ylamino]-benzyl}-benzenesulfonamide
Example 71: Propane-1-sulfonic acid 3-[6-(2-methoxy-phenyl)-pyrimidin-4-ylamino]-benzylamide
Example 72: 4-Fluoro-N-{3-[6-(2-methoxy-phenyl)-pyrimidin-4-ylamino]-benzyl}-benzenesulfonamide
Example 73: Thiophene-2-sulfonic acid 3-[6-(2-methoxy-phenyl)-pyrimidin-4-ylamino]-benzylamide
Example 74: N-{3-[6-(2-Methoxy-phenyl)-pyrimidin-4-ylamino]-benzyl}-C-phenyl-methanesulfonamide
Example 75: N-{3-[6-(4-Hydroxy-phenyl)-pyrimidin-4-ylamino]-benzyl}-methanesulfonamide
Example 76: N-{4-[6-(4-Hydroxy-phenyl)-pyrimidin-4-ylamino]-benzyl}-methanesulfonamide
Example 77: (1H-Benzoimidazol-2-yl)-{3-[6-(4-fluoro-2-isopropoxy-phenyl)-pyrimidin-4-ylamino]-benzyl}-amine
Example 78: 4-(6-{3-[(1H-Benzoimidazol-2-ylamino)-methyl]-phenylamino}-pyrimidin-4-yl)-phenol
Example 79: (3-Benzoimidazol-1-ylmethyl-phenyl)-[6-(2-fluoro-6-methoxy-phenyl)-pyrimidin-4-yl]-amine
Example 80: (3-Benzoimidazol-1-ylmethyl-phenyl)-[6-(2-isopropoxy-phenyl)-pyrimidin-4-yl]-amine
Example 81: (3-Benzoimidazol-1-ylmethyl-phenyl)-[6-(4-fluoro-2-isopropoxy-phenyl)-pyrimidin-4-yl]-amine
Example 82: 4-[6-(3-Benzoimidazol-1-ylmethyl-phenylamino)-pyrimidin-4-yl]-phenol
Example 83: 3-[6-(3-Benzoimidazol-1-ylmethyl-phenylamino)-pyrimidin-4-yl]-phenol
Example 84: 4-Fluoro-N-{3-[6-(2-methoxy-phenyl)-pyrimidin-4-ylamino]-benzyl}-benzamide
Example 85: 1-(4-Fluoro-phenyl)-3-{3-[6-(2-methoxy-phenyl)-pyrimidin-4-ylamino]-benzyl}-urea
Example 86: (4-Benzoimidazol-1-ylmethyl-phenyl)-(6-chloro-pyrimidin-4-yl)-amine
Example 87: (4-Benzoimidazol-1-ylmethyl-phenyl)-[6-(2-methoxy-phenyl)-pyrimidin-4-yl]-amine
Example 88: (4-Benzoimidazol-1-ylmethyl-phenyl)-[6-(4-fluoro-2-isopropoxy-phenyl)-pyrimidin-4-yl]-amine
Example 89: 4-[6-(4-Benzoimidazol-1-ylmethyl-phenylamino)-pyrimidin-4-yl]-phenol
Example 90: (6-Chloro-pyrimidin-4-yl)-(3-indol-1-ylmethyl-phenyl)-amine
Example 91: (3-Indol-1-ylmethyl-phenyl)-[6-(2-methoxy-phenyl)-pyrimidin-4-yl]-amine
Example 92: (6-Chloro-pyrimidin-4-yl)-[3-(2-morpholin-4-ylmethyl-benzoimidazol-1-ylmethyl)-phenyl]amine
Example 93: [6-(2-Methoxy-phenyl)-pyrimidin-4-yl]-[3-(2-morpholin-4-ylmethyl-benzoimidazol-1-ylmethyl)-phenyl]-amine
Example 94: [6-(4-Fluoro-2-methoxy-phenyl)-pyrimidin-4-yl]-[3-(2-morpholin-4-ylmethyl-benzoimidazol-1-ylmethyl)-phenyl]-amine

DETAILED DESCRIPTION OF THE INVENTION

In preferred embodiments the novel 4,6-disubstituted aminopyrimidine compounds according to the present invention are compounds of general formula (II) or (III),

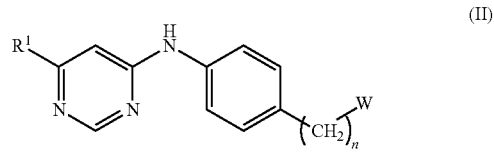

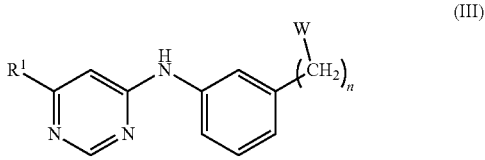

(III)

wherein the substituents have the above meanings. It is underlined that the phrases alkyl, alkoxy, aryl, heteroaryl, halogen etc. used in the definitions are given precisely below.

The preferred substituent and symbol meanings are as follows:

The symbol n is preferably 1 to 3, more preferably 1 or 2 and most preferably 1.

In the meaning of $R^1$ the aryl is preferably phenyl. It is optionally substituted with the substituents given above, preferably with alkoxy, halogen and alkyl. In a more preferred embodiment the phenyl is substituted with an alkoxy group (preferably in its second position) and optionally by halogen in one or more other position(s). In some preferred embodiment this phenyl is disubstituted.

In another preferred embodiment $R^1$ is a group of (a) wherein m is 1 or 2, more preferably 1.

In a further preferred embodiment $R^1$ is 5- or 6-membered heteroaryl containing 1 or 2 N-atom, preferably pyridine or pyrazole group, more preferably pyrazole group.

W has the following preferred meanings:

a) A group of formula (b) wherein $R^2$ is $C_{1-4}$ alkyl, preferably $C_{1-2}$ alkyl, most preferably methyl (i.e. those compounds where the —$(CH_2)_n$—W part is a methanesulfonamide group).

In another preferred embodiment $R^2$ stands for heteroaryl, which is preferably a 5- or 6-membered heteroaryl containing a heteroatom selected from the group of N, O and S, more preferably of 1 or 2 S-atom. In this case, $R^2$ is most preferably thiophene group.

b) In a further preferred embodiment W is heteroaryl, more preferably a fused bicyclic heteroaryl group which contains at least one heteroatom selected from the group of N, O and S (the heteroatom is preferably N) in one of the rings (this ring can be aromatic or non-aromatic) and the other ring is a benzene ring (these two rings are fused together to form the fused bicyclic heteroaryl group). More preferably the fused bicyclic heteroaryl group is an indolyl or isoindolyl group. Preferably this fused bicyclic heteroaryl ring joins to the $(CH_2)_n$ group of formula (I) through its N-atom. The fused bicyclic heteroaryl group can be substituted with 1 or 2 oxo group in the heteroatom (preferably nitrogen) containing ring. The fused bicyclic heteroaryl group also can be substituted with halogen, $C_{1-4}$ alkyl or $C_{1-4}$ alkoxy in the benzene ring. It means that in the meaning of W the heteroaryl is preferably a fused bicyclic heteroaryl, optionally substituted with one or more (preferably two) substituent selected from the following group: oxo, halogen, $C_{1-4}$ alkyl or $C_{1-4}$ alkoxy, more preferably from the group of oxo and halogen. In this preferred case W is a fused bicyclic heteroaryl, optionally substituted with one or more (preferably two) substituent selected from the group of oxo and halogen.

Examples of these preferred group are formulae groups (c), (d) and (e):

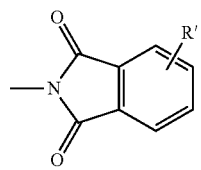

(c)

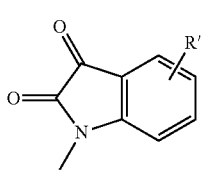

(d)

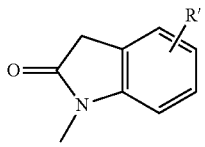

(e)

where in more preferred embodiments R' is hydrogen, halogen or $C_{1-4}$ alkyl, most preferably hydrogen.

When W stands for heteroaryl, in a further preferred embodiment W is a group of formula (f):

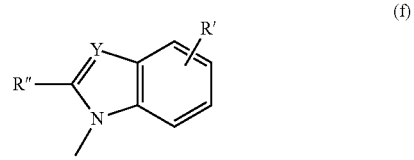

(f)

where Y is C or a heteroatom selected from the group of N, O and S (preferably C or N, most preferably N) and substituted with R' in the benzene ring wherein R' stands for hydrogen, halogen, $C_{1-4}$ alkyl or $C_{1-4}$ alkoxy, more preferably R' is hydrogen, halogen or $C_{1-4}$ alkyl, most preferably hydrogen (i.e. 1-benzimidazolyl group which can be named as 1-benzoimidazolyl or benzimidazo-1-yl or benzoimidazo-1-yl).

In a further preferred embodiment the group of formula (f) is substituted with a group of R", which stands for hydrogen or —$(CH_2)_k$-heterocycloalkyl group, where k is 0, 1, 2 or 3, preferably 1 or 2, most preferably 1. The heterocyloalkyl is preferably saturated ring of 4 to 7 atoms, more preferably of 5 or 6 ring atoms, wherein 1 or 2 ring member(s) is/are selected from the group consisting of O, S and $NR^x$ and the remaining atoms are carbon (where $R^x$ is hydrogen or a usual substituent, preferably alkyl). In a more preferred embodiment the heterocyloalkyl is saturated ring of 5 or 6 ring atoms, wherein 1 or 2 heteroatom ring member(s) is/are selected from the group consisting of O, S and NH. The heteroatom ring member is preferably NH. Most preferably the heterocycloalkyl group is morpholinyl.

c) In a further preferred embodiment W stands for a group of NH—$R^3$. $R^3$ is preferably hydrogen or heteroaryl. The heteroaryl group is preferably a fused bicyclic heteroaryl group which contains at least one heteroatom selected from the group of N, O and S (preferably N) in one of the rings (this ring can be aromatic or non-aromatic) and the other ring is a benzene ring (these two rings are fused together to form the fused heteroaryl ring). In a more preferred embodiment $R^3$ is a group of formula (g):

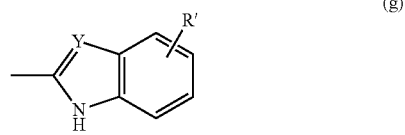

wherein Y is C or a heteroatom selected from the group of N, O and S (C or N, most preferably N), optionally substituted with R' in the benzene ring wherein R' stands for hydrogen, halogen, $C_{1-4}$ alkyl or $C_{1-4}$ alkoxy, more preferably R' is hydrogen, halogen or $C_{1-4}$ alkyl, most preferably hydrogen (i.e. 2-benzimidazolyl which can be named as 2-benzoimidazolyl or benzimidazo-2-yl or benzoimidazo-2-yl).

In a further preferred embodiment $R^3$ is —CO-aryl or —CO—NH-aryl, where the aryl is optionally substituted with one or more halogen. In a more preferred embodiment the aryl is phenyl which is optionally substituted with halogen. In another embodiment $R^3$ is phenyl substituted with halogen, preferably with F.

The especially preferred embodiments are as follows: compounds of Example 5, 6, 7, 13, 35, 37, 39, 48, 53, 54, 56, 64, 65, 66, 68, 69 and 71. These compounds showed CDK9 inhibitory effect at nanomolar or low nanomolar range and this fact enables us to expect beneficial use of them for the prophylaxis and/or treatment of diseases mentioned above. The following compounds showed the best pharmaceutical activity: compounds of Example 5, 6, 48, 53, 56, 64, 65, 66 and 68 especially those where 1-benzimidazolyl moiety (as a meaning of W in general formula (I)) is presented: see Example 64, 65 and 66.

In the context of the present invention, general formula (I) includes all stereoisomeric forms of the compounds of the present invention. The term "stereoisomer" as used herein includes all possible stereoisomeric forms, including all chiral, diastereomeric, racemic forms and all geometric isomeric forms of a structure, unless the specific stereochemistry or isomer form is specifically indicated. Where the compounds of the present invention contain one or more chiral centers, all possible enantiomeric and diastereomeric forms, as well as the racemate, are included. It is well known in the art how to prepare optically active forms, such as by resolution of racemic forms or by synthesis from optically active starting materials. All processes used to prepare compounds of the present invention and intermediates made therein are considered to be part of the present invention.

In the context of the present invention, it is intended to include all crystalline and polymorph forms and prodrugs of the compounds of the present invention.

The term "prodrug", as employed herein, denotes a compound that is a drug precursor which, upon administration to a subject, undergoes chemical conversion by metabolic or chemical processes to yield a compound of formula (I) or a salt and/or solvate thereof. A discussion of prodrugs is provided in T. Higuchi and V. Stella, Pro-drugs as Novel Delivery Systems (1987) Volume 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

The term "salt" means any ionic compound formed between one of the embodiments of the present invention and an acidic or basic molecule that can donate or accept ionic particle to/from its partner. The quaternary amine salts are also included.

Pharmaceutically acceptable (i.e., non-toxic, physiologically acceptable) salts are preferred, although other salts are also useful. Salts of the compounds of the formula (I) may be formed, for example, by reacting a compound of formula (I) with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are known.

The term "solvate" means a compound formed by the combination of solvent molecules with molecules or ions of the solute (solvation). Solute can be any of the embodiments of the present invention and the solvent can be water or any organic solvent.

The term "halogen" means fluorine, chlorine, bromine or iodine atoms.

The term "alkyl" refers to straight- or branched-chain saturated hydrocarbon groups having 1 to 6 carbon atoms (which can be named as $C_{1-6}$ alkyl, too). These groups may or may not be branched. Examples of alkyl include, but are not limited to, methyl, ethyl, n-propyl, i-propyl, n-butyl, s-butyl, t-butyl, n-pentyl, s-pentyl and s-hexyl.

In addition, the term is intended to include both unsubstituted and substituted alkyl groups, the latter referring to alkyl moieties having one or more hydrogen atoms replaced by usual substituents of alkyl groups, preferably selected from the following group: halogen, hydroxyl, alkoxy, cyano, amino and nitro. In preferred embodiments alkyl groups are unsubstituted or substituted with halogen. If another type of substituent is applied, then that is given in the definition [e.g. (alkyl)(aryloxy), alkylthio, alkylsulfinyl or alkylsulfonyl].

The term "aryl" is intended to mean any stable monocyclic or polycyclic aromatic moiety, which contains 6 to 14 carbon members, preferably 6 to 10 carbon members per ring. This includes benzene ring or benzene ring system fused to one or more further benzene rings, to form, e.g., anthracene, phenanthrene or naphthalene ring systems, or fused to heteroaryl rings.

The phenyl group is a preferred meaning of "aryl".

As used herein, the term "heteroaryl" refers to any stable mono- or polycyclic aromatic moiety containing one or more nitrogen, sulfur and/or oxygen heteroatoms together with the carbon ring-forming atoms. Heteroaryl moieties contain 5 to 13 members per ring, preferably 5 to 10. The phrase embraces such polycyclic rings where at least one of the rings is aromatic. Moreover, the phrase embraces all tautomeric forms, too.

In addition, the term is intended to include both unsubstituted and substituted heteroaryl groups. In case when one or more hydrogen atom(s) is/are replaced by usual substituents of heteroaryl groups, preferably the substituent(s) can be selected from the following group: halogen, hydroxyl, alkyl, alkoxy, cyano, amino and nitro. N-oxides and sulfur oxides and dioxides are also permissible substitutions where the substitution is made on a heteroatom. In preferred embodiments the heteroaryl group is unsubstituted or substituted with halogen.

Examples of "heteroaryl" groups used herein include furanyl, thiophenyl, pyrrolyl, imidazolyl, pyrazolyl, triazolyl, tetrazolyl, thiazolyl, triazolyl, oxazolyl, isoxazolyl, oxadiazolyl, oxo-pyridyl, thiadiazolyl, isothiazolyl, pyridyl, pyridazyl, pyrazinyl, pyrimidyl, quinazolinyl, quinolinyl, isoquinolinyl, benzofuranyl, benzothiophenyl, benzimidazolyl, indolyl, isoindolyl, indazolyl, and substituted versions thereof.

The term "aryloxy" is intended to mean an aryl group coupling via oxygen.

The term "heteroaryloxy" is intended to mean a heteroaryl group coupling via oxygen.

The term "alkoxy" is intended to mean an alkyl group coupling via oxygen.

The term "alkylthio" is intended to mean an alkyl group coupling via sulphur.

The term "vinylene-aryl" is intended to mean an aryl group coupling via —CH=CH— vinyl group.

The term "heterocycloalkyl" intended to mean a saturated ring of 4 to 7 atoms, preferably 5 or 6 ring atoms, wherein 1 or 2 ring members are selected from the group consisting of O, S and $NR^x$ and the remaining atoms are carbon (where $R^x$ is hydrogen or a usual substituent, preferably alkyl). There are no adjacent oxygen and/or sulfur atoms in the rings. Non-limiting examples of heterocycloalkyl rings are piperidyl, pyrrolidinyl, piperazinyl, morpholinyl, thiomorpholinyl, thiazolidinyl, 1,3-dioxolanyl, 1,4-dioxanyl, oxazolinyl, tetrahydrofuranyl, tetrahydrothiophenyl and tetrahydrothiopyranyl, preferably morpholinyl.

In any cases when substituent names follow each other means that all substituents are present in the certain position in the given order [e.g. ($C_{1-6}$ alkyl)($C_{6-10}$ aryloxy), see for example in Example 30].

In case of compounds of general formula (I) it can be declared that where an alkyl substitution is applied in a part of the molecule, then the corresponding alkoxy derivative can be prepared by a skilled person and vica versa. Moreover, when a phenyl or condensed phenyl group is present in the molecule, then the relating derivative having usual substituents in the phenyl ring can be prepared on the basis of the knowledge of a skilled person. The usual substituent is halogen, alkyl or alkoxy in general. In a further aspect of the present invention, the compounds of the present invention are used as pharmaceutically active agents. Further aspects of the present invention relate to the use of the compounds of the present invention for the preparation of a pharmaceutical composition useful for inhibition of protein kinase activity, preferably in prophylaxis and/or treatment of a disease selected from the group of cell proliferative disease, such as cancer; pain, such as inflammatory pain and neuropathic pain; inflammation; cardiovascular diseases, such as cardiac hypertrophy; and infectious disease, such as viral infections including HIV.

Other aspects of the present invention relate to methods for inhibition of protein kinase activity, preferably for prophylaxis and/or treatment of a disease selected from then group of cell proliferative disease, such as cancer; pain, such as inflammatory pain and neuropathic pain; inflammation; cardiovascular disease, such as cardiac hypertrophy; and infectious disease, such as viral infections including HIV; comprising administering to an individual a compound according to the present invention.

In certain embodiments of these aspects of the invention, the disease for prophylaxis and/or treatment can be found in an individual, such as a patient in need of such prophylaxis and/or treatment. An "individual" means a multi-cellular organism, for example an animal such as a mammal, including a primate. In addition to primates, such as humans, a variety of other mammals can be treated according to a method that utilizes one or more compounds of the present invention. For example, other mammals including, but not limited to, cows, sheep, goats, horses, dogs, cats, guinea pigs, rabbits, rats, mice or other bovine, ovine, equine, canine, feline, or rodent species can be used. In one particular such embodiment of these aspects, the individual is a human.

Another subject of the invention is providing pharmaceutical composition containing as active ingredient one or more compound(s) of general formula (I) together with one or more usual pharmaceutical auxiliary material(s). Formally another subject is the use of the compounds of general formula (I) in preparing such compositions. The applicable auxiliary materials are those which are generally applied in the preparation of pharmaceutical compositions, e.g. carriers, diluents, vehicles, coloring agents, flavoring agents, stabilizers, surfactants, carriers for the preparation of sustained release compositions etc. Further details can be found in the following book: Comprehensive Medicinal Chemistry (Corwin Hansch; Chairman of Editorial Board), Pergamon Press 1990, Volume 5., Chapter 25.2). The role of CDK9 in diseases such as and cardiovascular- and cell proliferative disorders, virus infections is described in details by Shudong Wang and Peter M. Fischer (Trends in Pharmacological Sciences, 29, 6, 2008, 302-313). Considering these facts certain embodiments of the present invention or their pharmaceutically acceptable salts and solvates can be used for the preparation of a pharmaceutical composition for prophylaxis and/or treatment of a disease selected from then group of cell proliferative disease, such as cancer; pain, such as inflammatory pain and neuropathic pain; inflammation; cardiovascular disease, such as cardiac hypertrophy; and infectious disease, such as viral infections including HIV. In addition a recent review by Bert M. Klebl and Axel Choidas (Future Virol. 1, 3, 2006, 317-330) describes the function of CDK9 in the propagation of HIV virus.

Hence, in a further aspect of the present invention, a method for preventing and/or treating infectious disease, including opportunistic disease, in a mammal, including a human, is provided, which method comprises administering to the mammal an amount of at least one compound of the present invention, effective to prevent and/or treat said infectious disease, including a opportunistic disease. In a particular embodiment of this method, the infectious disease, including opportunistic disease, includes virally induced infectious diseases. The virally induced infectious diseases, including opportunistic diseases, are caused by retroviruses, hepadnaviruses, herpesviruses, flaviviridae, and/or adenoviruses. In a further particular embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, including certain embodiments where the lentivirus is HIV-1 or HIV-2, or wherein the oncoretrovirus is selected from the group consisting of: HTLV-I, HTLV-II or BLV. In a further particular embodiment of this method, the hepadnavirus is selected from HBV, GSHV or WHV, including certain embodiments where the hepadnavirus is HBV, or wherein the herpesivirus is selected from the group comprising: HSV I, HSV II, EBV, VZV, HCMV or HHV 8, including certain embodiments where the herpesivirus is HCMV, or wherein the flaviviridae is selected from HCV, West Nile or Yellow Fever. Preferably in a particular embodiment of this aspect, the infectious disease is caused by HIV-1 or HIV-2.

As used herein, a "cell proliferative disease" includes a disease or disorder that affects a cellular growth, differentiation, or proliferation process. As used herein, a "cellular growth, differentiation or proliferation process" is a process by which a cell increases in number, size or content, by which a cell develops a specialized set of characteristics which differ from that of other cells, or by which a cell moves closer to or further from a particular location or stimulus. A cellular growth, differentiation, or proliferation process includes amino acid transport and degradation and other metabolic processes of a cell. A cellular proliferation disorder may be characterized by aberrantly regulated cellular growth, proliferation, differentiation, or migration. Cellular proliferation disorders include tumorigenic diseases or disorders. As used herein, a "tumorigenic disease or disorder" includes a disease or disorder characterized by aberrantly regulated cellular growth, proliferation, differentiation, adhesion, or migration, which may result in the production of or tendency to produce tumors. As used herein, a "tumor" includes a benign or malignant mass of tissue. Examples of cellular growth or proliferation disorders include, but are not limited to tumors, cancer, autoimmune diseases, viral diseases, fungal diseases, neurodegenerative disorders and cardiovascular diseases.

As described above, in certain embodiments of the invention, the compounds of the present invention are pharmaceutically active agents for prophylaxis and/or treatment of cell proliferative disease, including cancer. Thus, these compounds can be used for the manufacture of a pharmaceutical formulation for prophylaxis and/or treatment of cell proliferative disease, including such disease in a mammal such as a human.

Compounds of the present invention may also be useful in the chemoprevention of cancer. Chemoprevention is defined as inhibiting the development of invasive cancer by either blocking the initiating mutagenic event or by blocking the progression of pre-malignant cells, such as by blocking growth of the tumor, that have already suffered an insult or inhibiting tumor relapse. Compounds disclosed herein may also be useful in inhibiting tumor angiogenesis, metastasis and inducing apoptosis.

CDK9 is known to be involved in cardiac hypertrophy (reviewed in Sano & Schneider, Circulation Research, 2004, 95, 867). Activation of CDK9 to pathophysiological levels leads to mitochondrial dysfunction, apoptosis, and heart failure via suppression of PGC-1, an essential co-activator for the transcription of nuclear and mitochondrial genes that encode mitochondrial proteins (Sano et al., EMBO J., 2004, 23, 3559-3569), and hence blockade of CDK9 activity is an accepted strategy expected to aid in the treatment of cardiac hypertrophy. Cardiac hypertrophy is the heart's response to a variety of extrinsic and intrinsic stimuli that impose increased biomechanical stress. While hypertrophy can eventually normalize wall tension, it is associated with an unfavorable outcome and threatens affected patients with sudden death or progression to overt heart failure. Accumulating evidence from studies in human patients and animal models suggests that in most instances hypertrophy is not a compensatory response to the change in mechanical load, but rather is a maladaptive process. Cardiac hypertrophy, or thickening, of the heart muscle (myocardium) occurs in response to increased stress on the heart. It typically involves one of the bottom chambers of the heart, which are known as the ventricles. The right ventricle pumps blood to the lungs and the left ventricle pumps blood to the body. The most common causes of hypertrophy are related to increased blood pressure in either the lungs or the body. The extra work of pumping blood against the increased pressure causes the ventricle to thicken over time, the same way a body muscle increases in mass in response to weightlifting.

In particular embodiments the compounds of the present invention can be used for prophylaxis and/or treatment of a cardiovascular disease selected from: cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis, including such disease in a mammal, such as a human.

In certain embodiments of the invention, the compounds of the present invention may also be used to treat one or more of any type of pain, including such pain in a mammal, such as a human. In particular such embodiments said pain comprises inflammatory pain and/or neuropathic pain. Generally, pain is defined as an unpleasant sensory and emotional experience associated with actual or potential tissue damage, or described in terms of such damage, according to the International Association for the Study of Pain (IASP). Specifically, pain may occur as acute or chronic pain.

Another subtype of pain, inflammatory pain, can occur as acute as well as chronic pain. Resulting injuries of tissue and neurons must not but may develop into long-lasting chronic neuropathic pain effects in succession to such inflammatory events. Inflammatory pain is mediated by noxious stimuli like e.g. inflammatory mediators (e.g. cytokines, such as TNFcc, prostaglandins, substance P, bradykinin, purines, histamine, and serotonine), which are released following tissue injury, disease, or inflammation and other noxious stimuli (e.g. thermal, mechanical, or chemical stimuli). In addition, cytokines and growth factors can influence neuronal phenotype and function (Besson J. M., The neurobiology of pain, Lancet, 1999, 353(9164), 1610-1615). These mediators are detected by nociceptors (sensory receptors) that are distributed throughout the periphery of the tissue. Said nociceptors are sensitive to noxious stimuli (e.g. mechanical, thermal, or chemical), which would damage tissue if prolonged (Koltzenburg M, Neural mechanisms of cutaneous nociceptive pain, Clin J Pain, 2000, 16(3 Suppl), 131-138). A particular class of so called C-nociceptors represent a class of "silent" nociceptors that do not respond to any level of mechanical or thermal stimuli but are activated in presence of inflammation only.

Neuropathic (or neurogenic) pain, arises as a result of peripheral or central nerve dysfunction and includes a variety of conditions that differ in aetiology as well as location. Generally, the causes of neuropathic pain are diverse, but share the common symptom of damage to the peripheral nerves or components of central pathways. Without being bound by theory, the causative factors of neuropathic pain may be metabolic, viral or a mechanical nerve lesion. Neuropathic pain is believed to be sustained by aberrant somatosensory processes in the peripheral nervous system, the CNS, or both. Neuropathic pain is not directly linked to stimulation of nociceptors, but instead, is thought to arise e.g. from oversensitization of glutamate receptors on postsynaptic neurons in the gray matter (dorsal horn) of the spinal cord. Neuropathic pain is associated with conditions such as nerve degeneration in diabetes and postherpetic neuralgia (shingles). Neuropathic pain conditions are the consequence of a number of diseases and conditions, including diabetes, AIDS, multiple sclerosis, stump and phantom pain after amputation, cancer-related neuropathy, post-herpetic neuralgia, traumatic nerve injury, ischemic neuropathy, nerve compression, stroke and spinal cord injury.

Summarizing, available analgesic drugs often only produce insufficient pain relief. Although tricyclic antidepressants and some antiepileptic drugs, for example gabapentine, lamotrigine and carbamazepine, are efficient in some patients, there remains a large unmet need for efficient drugs for the treatment of these conditions. In conclusion, there is a high unmet need for safe and effective methods of treating one or more of any type of pain, in particular chronic inflammatory and/or neuropathic pain.

The term "pain" as used herein generally relates to any type of pain and broadly encompasses types of pain such as acute pain, chronic pain, inflammatory and neuropathic pain.

One aspect of the invention relates to methods and compositions for treating one or more of any type of pain, including those referenced herein, comprising administering an effective amount of at least one compound according to the present invention to a subject in need thereof, including where such subject is a mammal such as a human.

In other aspect of the present invention relates to a pharmaceutical composition comprising at least one compound according to the present invention as an active ingredient, together with at least one pharmaceutically acceptable carrier, excipient and/or diluent, in combination with an analgesic agent, wherein said analgesic agent has a mechanism of action other than inhibition of a CDK.

In certain embodiments of the invention, the compounds of the present invention are pharmaceutically active agents for prophylaxis and/or treatment of inflammatory diseases. Thus, these compounds can be used for the manufacture of a pharmaceutical formulation for prophylaxis and/or treatment of inflammation and inflammatory disease in mammals, including humans.

Inflammatory diseases can emanate from infectious and non-infectious inflammatory conditions which may result from infection by an invading organism or from irritative, traumatic, metabolic, allergic, autoimmune or idiopathic causes as shown in the following list:

I. Acute infections
A. Viral B. Bacterial
II. Noninfectious causes
Chronic (granulomatous) diseases

| A. Bacterial | B. Spirochetal |
| C. Mycotic (Fungal) | D. Idiopathic |

IV. Allergic, immune, and idiopathic disorders
A. Hypersensitivity reactions
B. Immune and idiopathic disorders
V. Miscellaneous inflammatory conditions
A. Parasitic infections
B. Inhalation causes:
　Acute (thermal) injury
　Pollution and inhalant allergy
　Carcinogens
　Radionecrosis
C. Radiation injury:

In yet another particular embodiment, said inflammation is mediated preferably by the cytokines TNF-α, IL-1β, GM-CSF, IL-6 and/or IL-8.

EXAMPLES

A) Syntheses of Compounds

A1) General Synthesis Schemes

The synthesis of the derivatives of 4,6-disubstituted pyrimidines according to the present invention was preferably carried out according to the general synthetic sequence, shown in Scheme 1, involving in a first step amination of the pyrimidine ring followed by Suzuki reaction or an inverse order of the reaction steps.

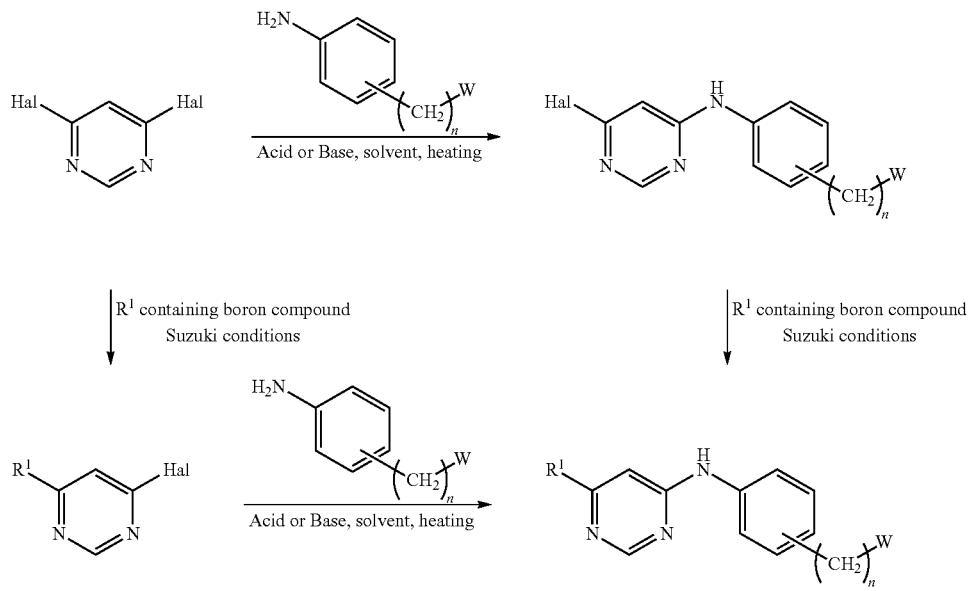

Introduction of the amine moiety to the pyrimidine ring can be performed by known methods (J. E. Arrowsmith et al., Journal of Medicinal Chemistry 1989, 32(3), 562-568, J. R. Porter et al, Bioorganic Medicinal Chemistry Letters 2002, 12(12), 1595-1598). For example, as outlined in Scheme 1, amination is performed by reacting equimolar quantities of 4,6-dihalogenated pyrimidine and an amino compound in a polar solvent, and in the presence of an organic base or an organic or inorganic acid at temperatures in the range of 50 to 120° C. Preferably, the polar solvent is N-methyl-2-pyrrolidinone (NMP) or a lower alcohol, such as isopropanol or butanol, the organic base is selected for instance from N,N-diisopropylethylamine (DIPEA), N-methyl-piperidine or NEt$_3$, the acid can be selected for instance from HCl, H$_2$SO$_4$, CH$_3$COOH and the reaction is carried out at a temperature in the range of 60 to 110° C., preferably in the range of 70 to 100° C. It is to be understood, that the reaction temperature depends on the reactivity of the amino compound: for less reactive amino compounds a reaction temperature in the range of 80 to 110° C. is preferred and in these cases a higher boiling solvent such as isopropanol, butanol or NMP affords the desired compounds in good yields.

The introduction of R$^1$ into the pyrimidine scaffold as outlined in Scheme 1, is performed preferably via Suzuki coupling at temperatures in the range of 60 to 110° C., preferably at temperatures in the range of 70 to 100° C., more preferably between 75 to 90° C. (I. Minoru, K. Machiko, T. Masanao, Synthesis 1984, 936-938; J. P. Wolfe, R. A. Singer, B. H. Yang and S. L. Buchwald, Journal of the American Chemical Society 1999, 121, 9550-9561).

The reaction is carried out in organic solvents, such as DME, DMF, THF, dioxane or methanol or this reaction is carried out in a mixture of an organic solvent and water, such as DMF/water, DME/water or THF/water, in the presence of a base, such as NaHCO$_3$, NaOH, TlOH, NaOMe, K$_2$CO$_3$, K$_3$PO$_4$, NEt$_3$, Cs$_2$CO$_3$ or Tl$_2$CO$_3$ and in the presence of a catalyst, such as PdCl$_2$(dppf) {[1,1-bis-(diphenylphosphino)ferrocene] dichloropalladium II}, Pd(PPh$_3$)$_4$ or PdCl$_2$(PPh$_3$)$_2$ or a catalyst/ligand system, such as Pd(OAc)$_2$/PPh$_3$, Pd(OAc)$_2$/2-(Dicyclohexylphosphino)-biphenyl or Pd(OAc)$_2$/tris (2,4,6-trimethoxyphenyl) phosphine.

The R$^1$ containing boron compound used for this reaction is selected from the group comprising:

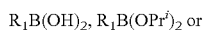

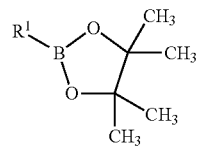

The chemistry described above can be done in either order and further derivatisation can be carried out after amination and before/after subsequent Suzuki cross coupling. Other suitable methods will be apparent to the chemist skilled in the art as will be the methods for preparing the starting materials and intermediates. When protecting groups have been used, optionally a final deprotecting step can be carried out according to general deprotecting reactions known to a person skilled in the art.

During the preparation of some embodiments of the current invention the following reaction scheme (Scheme 2) is applied. In the prepared compounds —NHSO$_2$R$_2$ stands in the meaning of W.

Scheme 2

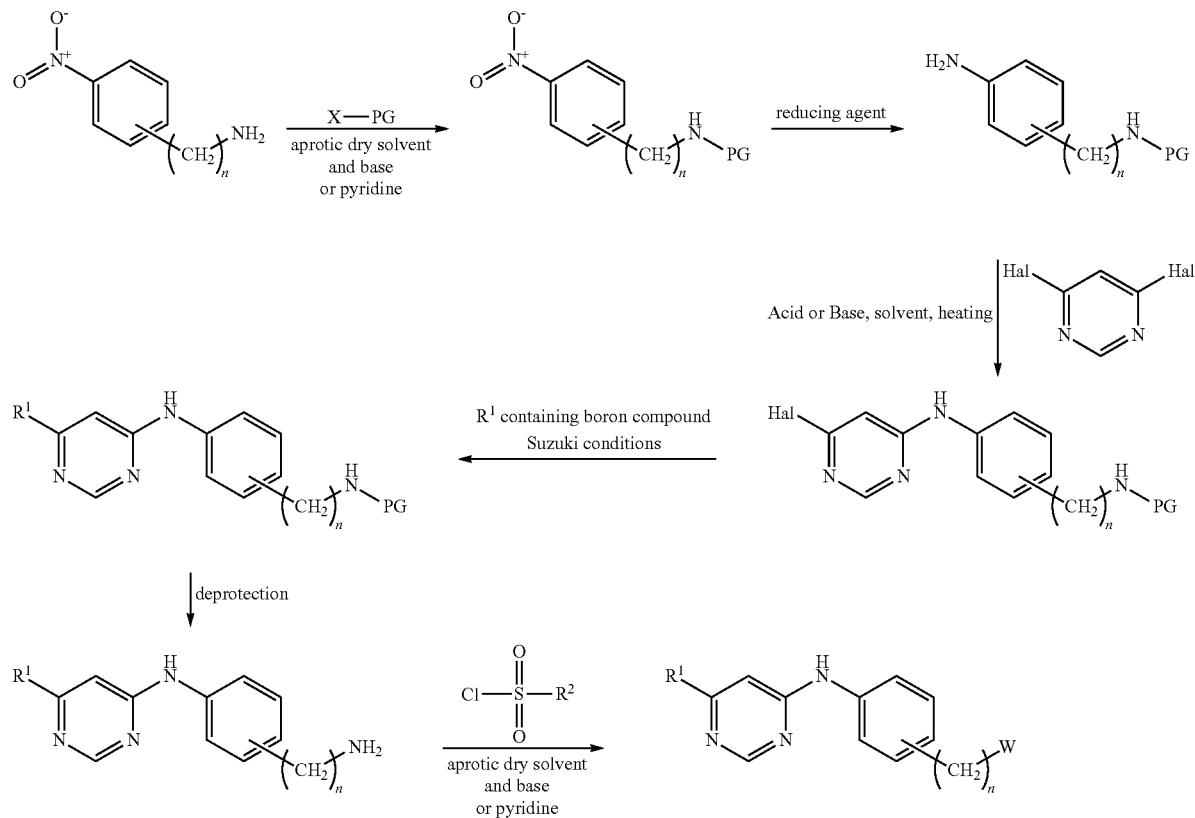

PG represents protecting group. Choosing proper protecting group is essential but it should be known to a person skilled in the art. X stands for a leaving group which can be any halogen, mesyloxy, trifluoromesyloxy or hydroxy group depending on the protecting group applied. $R^2$ stands for optionally substituted any alkyl, aryl or heteroaryl group. Other groups are as defined above. This reaction route involves an acylation step after deprotection that may be carried out preferably in pyridine by a sulfonyl chloride at a temperature in the range of 0 to 40° C. Amination of dihalo pyrimidine and the Suzuki conditions were same as described above. Reducing agent means all reagent that can be applied for the reduction of nitro group to amine are known to a person skilled in the art or described in Handbook of Reagents for Organic Synthesis: Oxidizing and Reducing Agents (2003), preferably $H_2$/Pt, $H_2$/Pd, $H_2$/Raney-$N_1$, $N_2H_4$—optionally catalyst (Pt, Pd or Raney-Ni), Sn, Fe, Zn, $SnCl_2$ or sodium dithionite. Solvents are preferably alcohol (any type), acetic acid or water under basic, neutral or acidic conditions at a temperature in the range of 20 to 120° C.

In addition, compounds $H_2N$-Ph-$(CH_2)_n$—W of the present invention (where W is —$NHSO_2R_2$) can be synthesized as follows (Scheme 3):

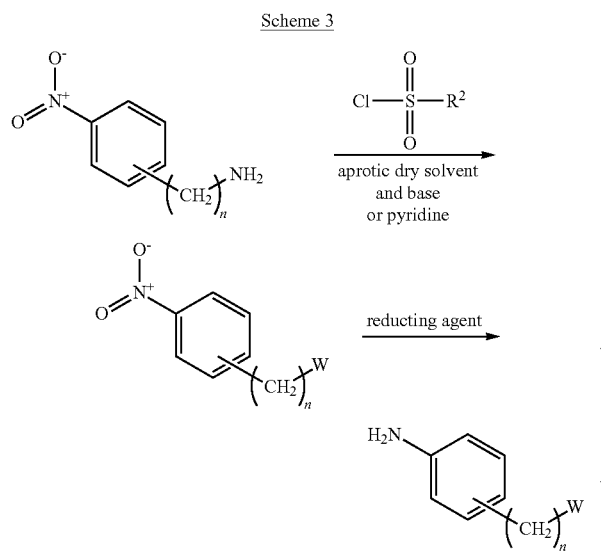

Scheme 3

Groups and conditions as described above.

Alternatively the compounds $H_2N$-Ph-$(CH_2)_n$—W of the present invention can be synthesized [where W is group of (c), (d), (e) and (f)] as depicted in Scheme 4:

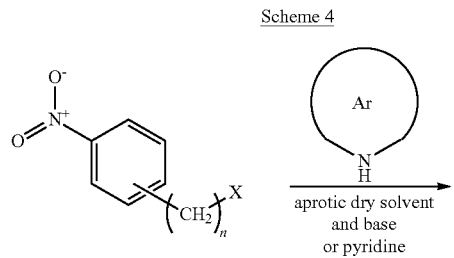

Scheme 4

Ar together with —NH— stands for a heteroaryl group which contains at least one N-atom. The heteroaryl group in question has a partly acidic NH functionality in the ring. In this case first step involves alkylation of a partly acidic NH containing heteroaromatic or condensed heteroaromatic ring system. This step can be carried out in an aprotic dry solvent preferably dichloromethane, tetrahydrofurane, N,N-ditehyl-formamide dioxane benzene, toluene or acetonitrile at a temperature in the range of 0 to 80° C. in the presence of any organic or inorganic base preferably trietylamine, N,N-diisopropyl-ethylamine, DBU, dialkyl-aniline, DMAP alkali-carbonate, -hydrocarbonate, -hydroxide, -hydride, -alkoxyde. Other groups and conditions as described above.

Alternatively the compounds $H_2N$-Ph-$(CH_2)_n$—W of the present invention can be synthesized [especially where W is group of (g)] as depicted in Scheme 5:

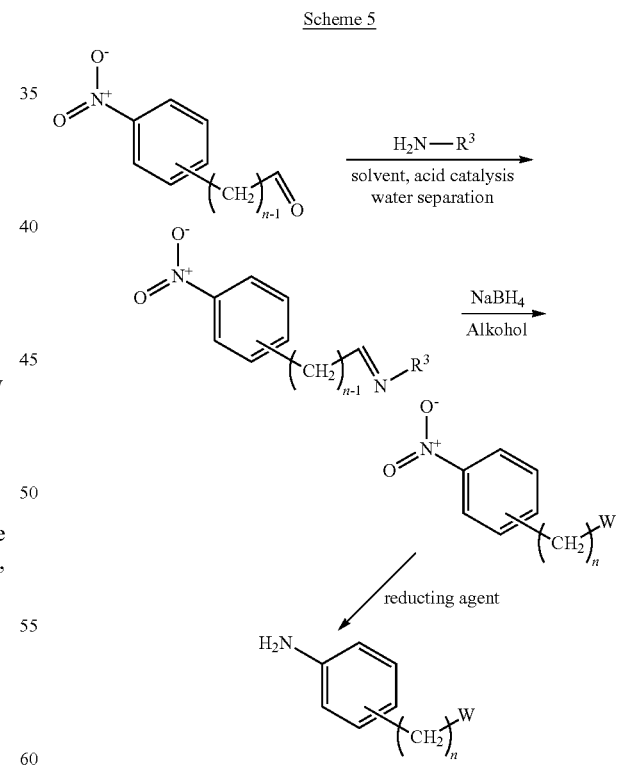

Scheme 5

In Scheme 5 $R^3$ represents alkyl, alkoxy, aryl, aryloxy, heteroaryl, heteroaryloxy, aminoalkyl, aminoaryl or aminoheteroaryl. The aldehyde compound can be condensed with a primary amino derivative in an organic solvent preferably in any alcohol, toluene, benzene, terahydrofurane, dioxane or acetonitrile applying water separation equipment or some materials to catch water that produces during the reaction. Applied reaction temperature is in the range of 50 to 120° C. Furthermore, additional acid catalyst can be used such as organic or inorganic acids, preferably benzenesulfonic acid, p-taluenesulfonic acid, methanesulfonic acid, trifluoromethanesulfonic acid, acetic acid, trifluoroacetic acid, hydrochloric acid, sulfuric acid phosphonic acid or nitric acid. Then the resulted imines can be reduced to secondary amines by alkali borohydrides preferably sodium borohydride in alcohols at a temperature in the range of 20 to 85° C. Other groups and conditions as described above.

In this reaction the quality of the applied primery amine (which can be a hydrazine type compound, if $R^3$ represents aminoalkyl, aminoaryl or aminoheteroaryl, or hydroxylamine type compound, if $R^3$ represents alkoxy, aryloxy, and heteroaryloxy) is not limited practically (apart from those which cause an extreme steric hindrance). This is the reason why the meaning of $R^3$ is claimed broadly.

A2) Preparation of Specific Compounds

Example 1

(N-[3-(6-Chloro-pyrimidin-4-ylamino)-benzyl]-methanesulfonamide)

Step 1:

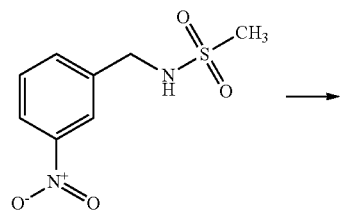

5.0 g 3-Nitro-benzylamine hydrochloride (26.5 mmol) was dissolved in 50 cm³ abs. pyridine and the mixture was cooled in an ice bath to 0° C. 2.61 cm³ methanesulfonyl chloride (3.864 g, 34 mmol) was added droppwise. The mixture was stirred for two hours at 0° C. and overnight at room temperature. It was evaporated under reduced pressure and 150 cm³ of 0.5 N HCl was added. The suspension was extracted three times with 70-70 cm³ of ethyl-acetate. The combined organic layer was washed with brine, dried over $MgSO_4$, decolorized with activated carbon and evaporated to dryness. The process resulted in a light orange oil (ca. 6 g) which was used directly without further purification in the next step.

Step 2:

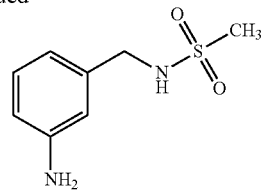

6.104 g N-(3-Nitro-benzyl)-methanesulfonamide (obtained in Step 1, 26.5 mmol) was dissolved in 100 cm³ of methyl-alcohol and dichloromethane 1:1 mixture 1 g of Pd catalyst (10% Pd on activated carbon) was added. The mixture was stirred vigorously in $H_2$ atmosphere under atmospheric pressure at room temperature until TLC was indicated the completion of the reaction. The catalyst was filtered off and the filtrate was evaporated to dryness. The residual yellow solid (ca. 5 g) was used directly without any further purification in the next step.

Step 3:

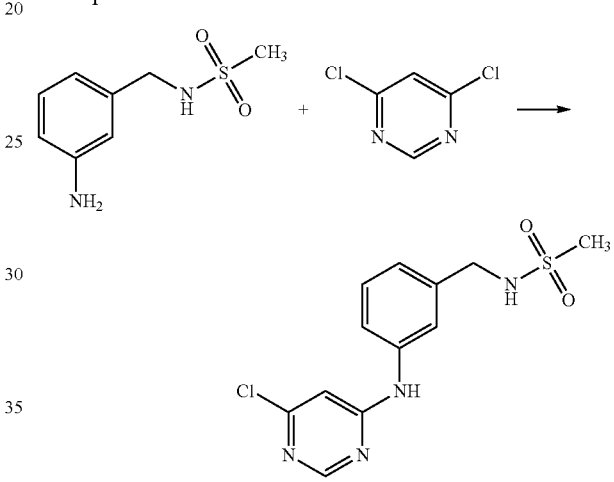

5.309 g N-(3-Amino-benzyl)-methanesulfonamide (obtained in Step 2, 26.5 mmol) and 4.739 g 4,6-dichloropyrimidine (31.81 mmol) was dissolved in 120 cm³ of isopropyl-alcohol, 6.93 cm³ N,N-diisopropyl-ethylamine (5.140 g, 39.76 mmol) was added and the mixture was refluxed for four days. The reaction mixture was cooled to room temperature and the precipitated compound was filtered off. The light yellow product was washed well with diethyl-ether and air-dried. 3.612 g N-[3-(6-Chloro-pyrimidin-4-ylamino)-benzyl]-methanesulfonamide was obtained in more than 98% purity and in 44% overall yield. For analitical results and compound identification see Table 1. The compound was used as a starting material in the preparation of Example 2-32 and 75.

Example 2

(N-{3-[6-(2-Benzyloxy-phenyl)-pyrimidin-4-ylamino]-benzyl}-methanesulfonamide)

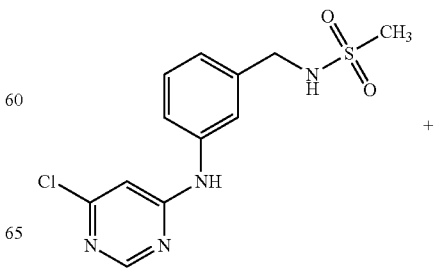

-continued

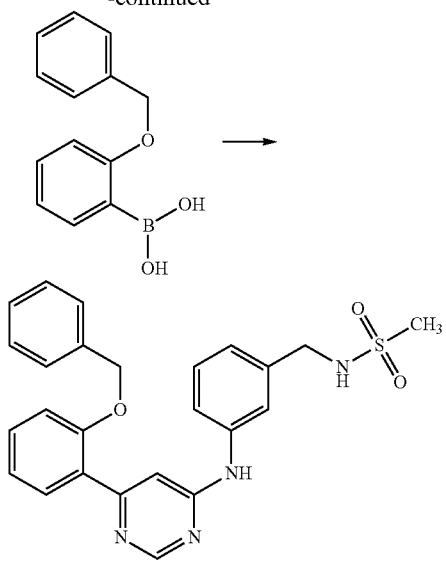

219 mg N-[3-(6-Chloro-pyrimidin-4-ylamino)-benzyl]-methanesulfonamide (prepared in Example 1) (0.70 mmol) was suspended in 30 cm³ dimethoxyethane and the flask was filled with argon properly. 58 mg Tetrakis(thriphenylphosphine) palladium[0] (0.05 mmol) was added and the mixture was stirred at room temperature for 30 minutes. Then 228 mg 2-benzyloxyphenyl-boronic acid (1 mmol), 318 mg anhydrous Na₂CO₃ (3 mmol) and 6 ml water was added. The mixture was ferluxed overnight while slow argon flow was being applied. The reaction mixture was poured to 80 cm³ 1M NaH₂PO₄ solution and it was extracted three times with 50-50 cm³ of ethyl-acetate. The combined organic layer was washed with brine, dried over MgSO₄, decolorized with activated carbon and evaporated to dryness. The residual solid was recrystallized from minimal amount of acetonitrile and air-dried to give the desired product (127 mg, 40% yield). For analitical results and compound identification see Table 1.

Example 3-32 and 75

Compounds were prepared according to a same manner described in Example 2 using the appropriate boronic acid and reaction time (until TLC indicates the completion of the reaction). Yields were between 15-70% and in some cases column chromatography was used to purify products. For analitical results and compound identification see Table 1.

Example 33

(N-[4-(6-Chloro-pyrimidin-4-ylamino)-benzyl]-methanesulfonamide)

Step 1:

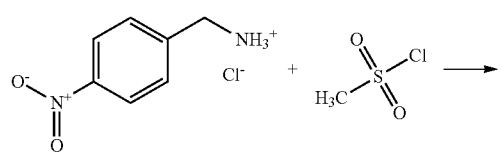

-continued

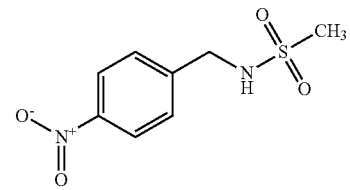

5.0 g 4-Nitro-benzylamine hydrochloride (26.5 mmol) was dissolved in 50 cm³ abs. pyridine and the mixture was cooled in an ice bath to 0° C. 2.61 cm³ methanesulfonyl chloride (3.864 g, 34 mmol) was added droppwise. The mixture was stirred for two hours at 0° C. and overnight at room temperature. It was evaporated under reduced pressure and 150 ml of 0.5 N HCl was added. The suspension was extracted three times with 70 cm³ of ethyl-acetate. The combined organic layer was washed with brine, dried over MgSO₄, decolorized with activated carbon and evaporated to dryness. The process resulted in a light orange solid (ca. 6 g) which was used directly without further purification in the next step.

Step 2:

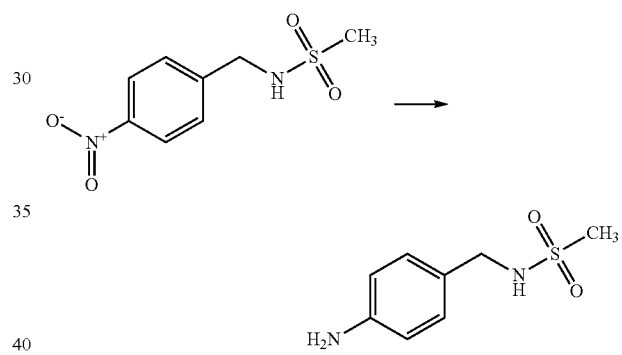

6.104 g N-(4-Nitro-benzyl)-methanesulfonamide (obtained in Step 1, 26.5 mmol) was dissolved in 100 cm³ of methyl-alcohol and dichloromethane 1:1 mixture 1 g of Pd catalyst (10% Pd on activated carbon) was added. The mixture was stirred vigorously in H₂ atmosphere under atmospheric pressure at room temperature until TLC was indicated the completion of the reaction. The catalyst was filtered off and the filtrate was evaporated to dryness. The residual off-white solid (ca. 5 g) was used directly without any further purification in the next step.

Step 3:

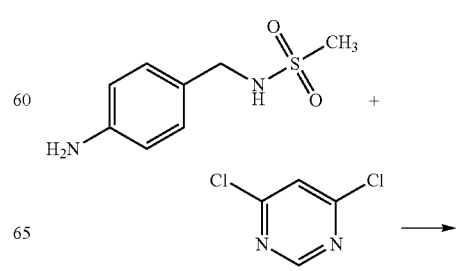

-continued

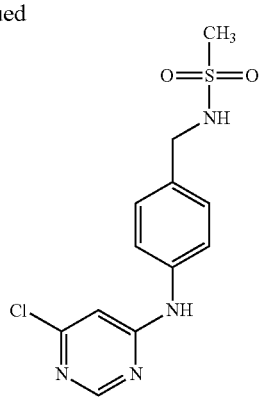

5.309 g N-(4-Amino-benzyl)-methanesulfonamide (obtained in Step 2, 26.5 mmol) and 4.739 g 4,6-dichloropyrimidine (31.81 mmol) was dissolved in 120 cm³ of isopropyl-alcohol, 6.93 cm³ N,N-diisopropyl-ethylamine (5.140 g, 39.76 mmol) was added and the mixture was refluxed for four days. The reaction mixture was cooled to room temperature and the precipitated compound was filtered off. The light yellow product was washed well with diethyl-ether and air-dried. 3.813 g N-[4-(6-Chloro-pyrimidin-4-ylamino)-benzyl]-methanesulfonamide was obtained above 98% purity in 46% overall yield. For analitical results and compound identification see Table 1. The compound was used as a starting material in the preparation of Example 34-58 and 76.

Example 34

(N-{4-[6-(2-Methoxy-phenyl)-pyrimidin-4-ylamino]-benzyl}-methanesulfonamide)

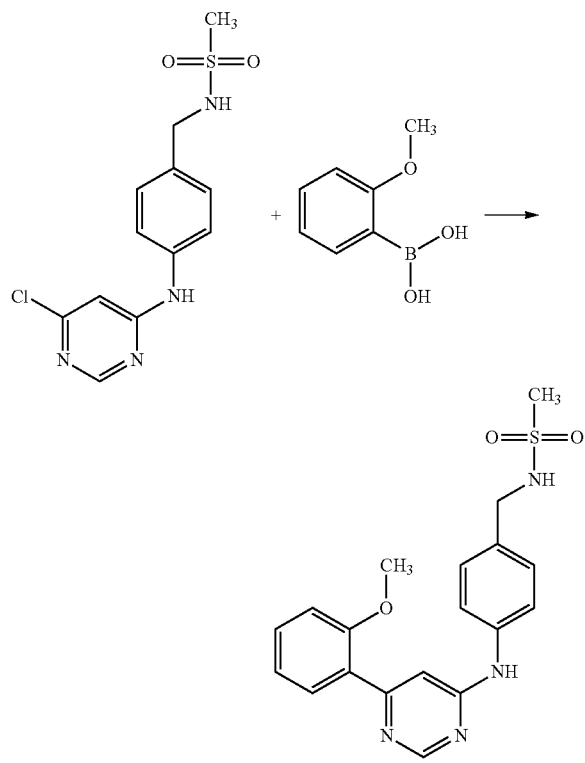

219 mg N-[4-(6-Chloro-pyrimidin-4-ylamino)-benzyl]-methanesulfonamide (prepared in Example 33) (0.70 mmol) was suspended in 30 cm³ dimethoxyethane and the flask was filled with argon properly. 58 mg Tetrakis(thriphenylphosphine) palladium[0] (0.05 mmol) was added and the mixture was stirred at room temperature for 30 minutes. Then 152 mg 2-methoxyphenyl-boronic acid (1 mmol), 318 mg anhydrous $Na_2CO_3$ (3 mmol) and 6 ml water was added. The mixture was ferluxed overnight while slow argon flow was being applied. The reaction mixture was poured to 80 cm³ 1M $NaH_2PO_4$ solution and it was extracted three times with 50-50 cm³ of ethyl-acetate. The combined organic layer was washed with brine, dried over $MgSO_4$, decolorized with activated carbon and evaporated to dryness. The residual solid was recrystallized from minimal amount of acetonitrile and air-dried to give the desired product (173 mg, 45% yield). For analitical results and compound identification see Table 1.

Example 35-58 and 76

Compounds were prepared according to a same manner described in Example 33 using the appropriate boronic acid and reaction time (until TLC indicates the completion of the reaction). Yields were between 15-70% and in some cases column chromatography was used to purify products. For analitical results and compound identification see Table 1.

Example 59

((1H-Benzoimidazol-2-yl)-[3-(6-chloro-pyrimidin-4-ylamino)-benzyl]-amine)

Step 1:

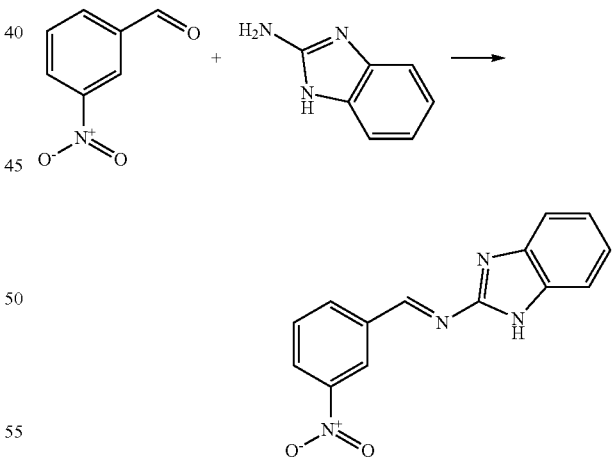

6.045 g 3-Nitrobenzaldehyde (400 mmol) was dissolved in 100 cm³ of toluene and 5.326 g 2-aminobenzimidazole (40 mmol) and 10 mg of p-toluenesulfonamide was added. The reaction mixture was refluxed overnight using Dean-Stark trap. The precipitated solid was filtered off after cooling to room temperature, washed with toluene and air dried. Yield: 9.37 g (88%) yellow powder. It was used directly without any further purification in the next step.

Step 2:

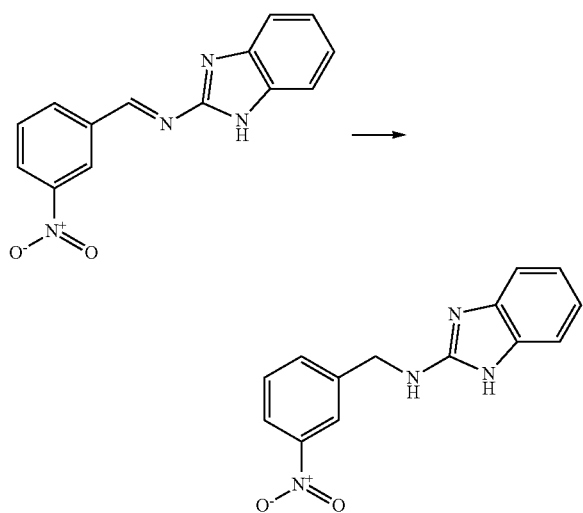

9.319 g (1H-Benzoimidazol-2-yl)-(3-nitro-benzylidene)-amine (obtained in Step 1, 35 mmol) was dissolved in 350 cm³ of ethyl-alcohol and 1.513 g sodium borohydride (40 mmol) was added in portions. The reaction mixture was stirred for 6 hours at 40-50° C. Then the mixture was evaporated under reduced pressure, 200 cm³ of water was added and it was extracted with 3×100 cm³ ethyl-acetate. Combined organic layer was washed with brine, dried over MgSO₄, decolorized with activated carbon and evaporated to dryness. The residual solid was recrystallized from minimal amount of acetonitrile and air-dried to give the desired product as an off-white solid. Yield: 8.15 g (87%). Ret. time: 0.46-2.21-2.43 min., (M+H)⁺=269 (M−H)⁻=267; ¹HNMR (DMSO-d₆, 300 MHz), δ (ppm): 10.93 (s, 1H), 8.25 (s, 1H), 8.10 (d, J=8.13 Hz, 1H), 7.85 (d, J=7.62 Hz, 1H), 7.63 (t, J=8.85 Hz, 1H), 7.28 (t, J=6.06 Hz, 1H), 7.13 (d, J=8.22 Hz, 2H), 6.96 (m, 2H), 4.64 (d, J=6.12 Hz, 2H).

Step 3:

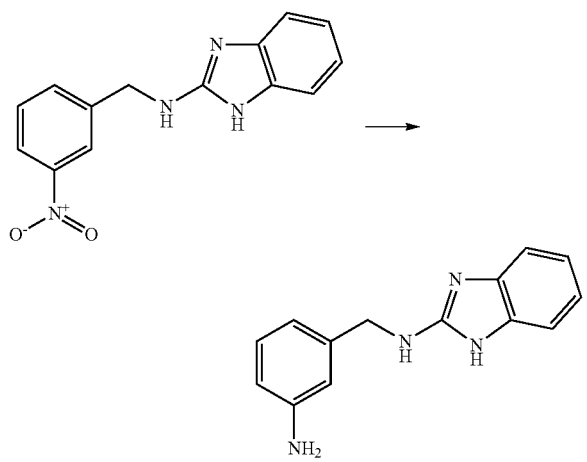

8.048 g (1H-Benzoimidazol-2-yl)-(3-nitro-benzyl)-amine (obtained in Step 2, 30 mmol) was dissolved in 150 cm³ of ethyl-alcohol and 27.076 g SnCl₂ dihydrate (120 mmol) was added in portions. The reaction mixture was refluxed for 6 hours. Then the mixture was evaporated under reduced pressure, 200 cm³ of 2N NaOH and 150 cm³ of ethyl-acetate was added and it was stirred for 30 minutes vigorously while it was being cooled in an ice bath. The precipitated solid was filtered off on a Buchner funnel and washed well with ethyl-acetate. Filtrate was separated and extracted further three times with 100-100 cm³ ethyl-acetate. The combined organic layer was washed with brine, dried over MgSO₄, decolorized with activated carbon and evaporated to dryness. The residual solid was recrystallized from minimal amount of acetonitrile and air-dried to give the desired product as an off-white solid. Yield: 4.78 g (67%). Ret. time: 0.45-1.56 min., (M+H)⁺=239 (M−H)⁻=237; ¹HNMR (DMSO-d₆, 300 MHz), δ (ppm): 10.97 (s, 1H), 7.10 (bs, 2H), 6.97-6.78 (m, 4H), 6.56 (s, 1H), 6.50 (d, J=7.47 Hz, 1H), 6.42 (d, J=7.83 Hz, 1H), 4.98 (s, 2H), 4.36 (d, J=6.00 Hz, 2H).

Step 4:

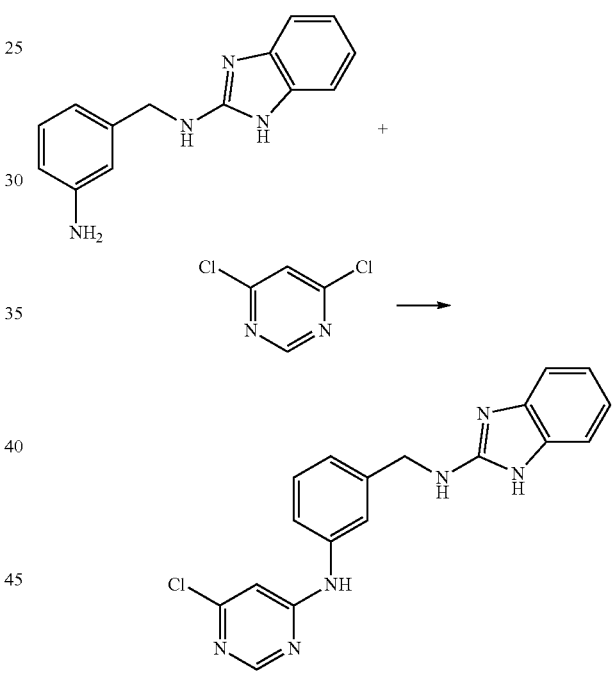

2.500 g (3-Amino-benzyl)-(1H-benzoimidazol-2-yl)-amine (obtained in Step 3, 10.50 mmol) and 1.879 g 4,6-dichloropyrimidine (12.61 mmol) was dissolved in 100 cm³ of isopropyl-alcohol, 2.64 cm³ N,N-diisopropyl-ethylamine (1.956 g, 15.13 mmol) was added and the mixture was refluxed for four days. Then the mixture was evaporated under reduced pressure, 100 cm³ of water was added and it was extracted with 3×70 cm³ ethyl-acetate. Combined organic layer was washed with brine, dried over MgSO₄ and evaporated to a yellowish oil. The residue was crystallized from minimal amount of acetonitrile and washed with diethyl-ether to give the desired product as an off-white solid. Yield: 3.11 g (85%). For analitical results and compound identification see Table 1. The compound was used as a starting material in the preparation of Example 60-62, 77 and 78.

Example 60

((1H-Benzoimidazol-2-yl)-{3-[6-(2-methoxy-phenyl)-pyrimidin-4-ylamino]-benzyl}-amine)

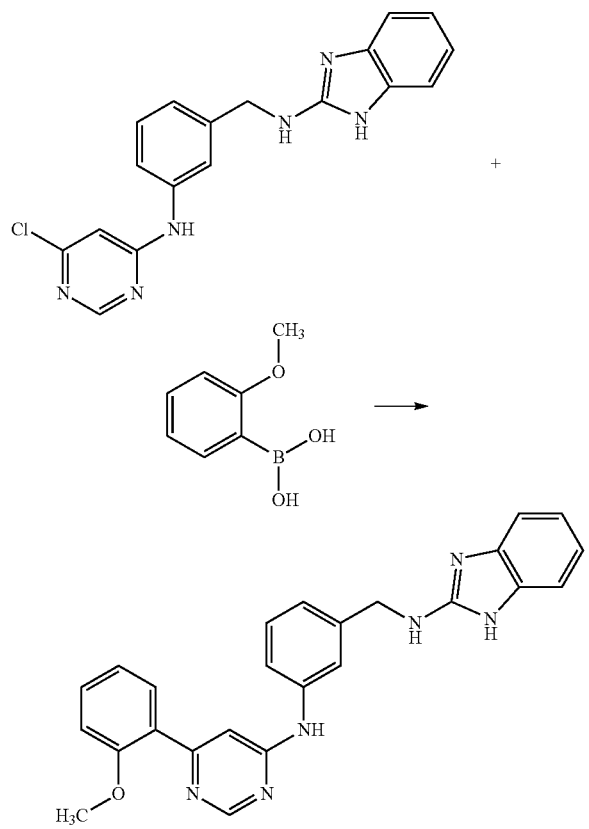

246 mg (1H-Benzoimidazol-2-yl)-[3-(6-chloro-pyrimidin-4-ylamino)-benzyl]-amine (prepared in Example 59) (0.70 mmol) was suspended in 30 cm³ dimethoxyethane and the flask was filled with argon properly. 58 mg Tetrakis(triphenylphosphine) palladium[0] (0.05 mmol) was added and the mixture was stirred at room temperature for 30 minutes. Then 152 mg 2-methoxyphenyl-boronic acid (1 mmol), 318 mg anhydrous $Na_2CO_3$ (3 mmol) and 6 ml water was added. The mixture was ferluxed overnight while slow argon flow was being applied. The reaction mixture was poured to 80 cm³ 1M $NaH_2PO_4$ solution and it was extracted three times with 50-50 cm³ of ethyl-acetate. The combined organic layer was washed with brine, dried over $MgSO_4$, decolorized with activated carbon and evaporated to dryness. The residual solid was recrystallized from minimal amount of acetonitrile and air-dried to give the desired product (146 mg, 50% yield). For analitical results and compound identification see Table 1.

Example 61-62, 77 and 78

Compounds were prepared according to a same manner described in Example 60 using the appropriate boronic acid and reaction time (until TLC indicates the completion of the reaction). Yields were between 50-70%. For analitical results and compound identification see Table 1.

Example 63

((3-Benzoimidazol-1-ylmethyl-phenyl)-(6-chloro-pyrimidin-4-yl)-amine)

Step 1:

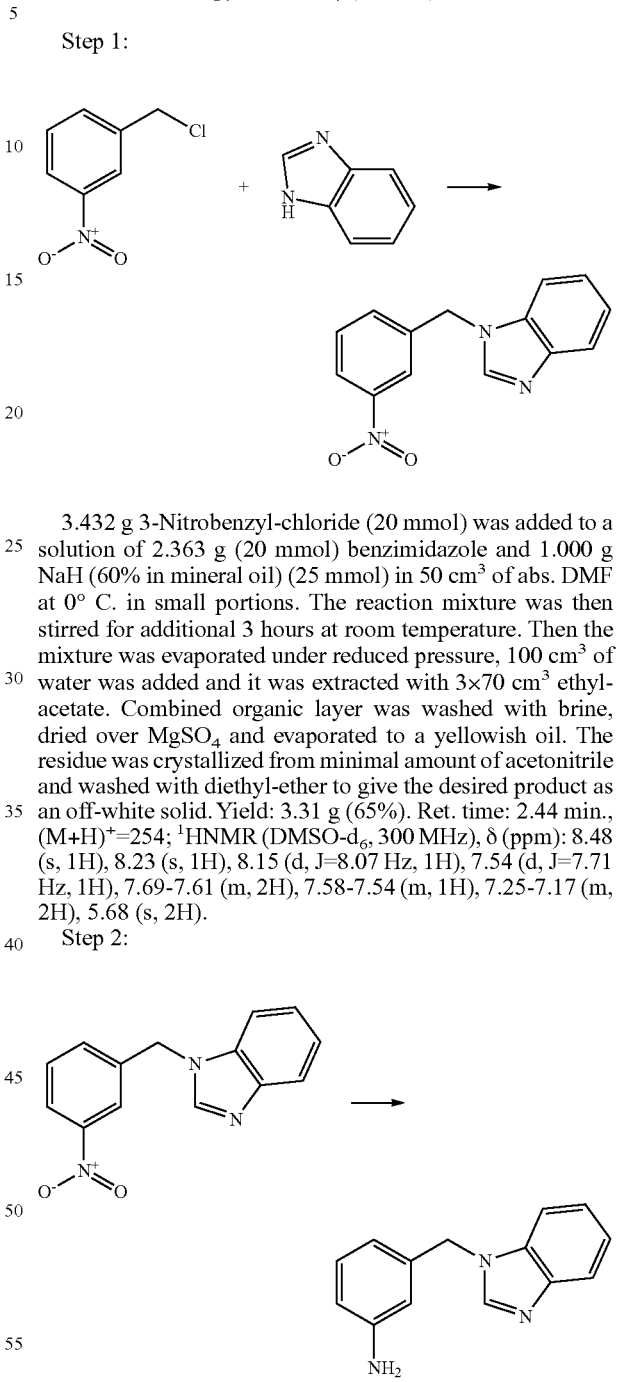

3.432 g 3-Nitrobenzyl-chloride (20 mmol) was added to a solution of 2.363 g (20 mmol) benzimidazole and 1.000 g NaH (60% in mineral oil) (25 mmol) in 50 cm³ of abs. DMF at 0° C. in small portions. The reaction mixture was then stirred for additional 3 hours at room temperature. Then the mixture was evaporated under reduced pressure, 100 cm³ of water was added and it was extracted with 3×70 cm³ ethyl-acetate. Combined organic layer was washed with brine, dried over $MgSO_4$ and evaporated to a yellowish oil. The residue was crystallized from minimal amount of acetonitrile and washed with diethyl-ether to give the desired product as an off-white solid. Yield: 3.31 g (65%). Ret. time: 2.44 min., $(M+H)^+=254$; ¹HNMR (DMSO-$d_6$, 300 MHz), δ (ppm): 8.48 (s, 1H), 8.23 (s, 1H), 8.15 (d, J=8.07 Hz, 1H), 7.54 (d, J=7.71 Hz, 1H), 7.69-7.61 (m, 2H), 7.58-7.54 (m, 1H), 7.25-7.17 (m, 2H), 5.68 (s, 2H).

Step 2:

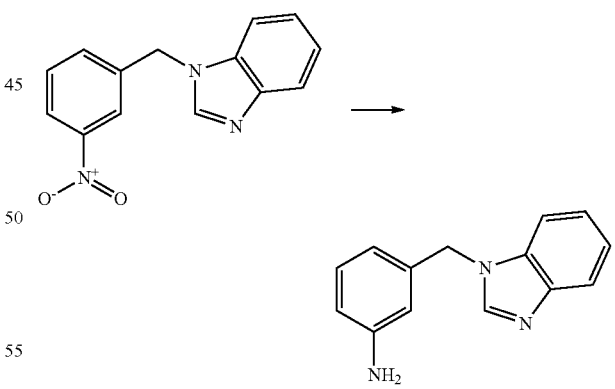

3.206 g 1-(3-Nitro-benzyl)-1H-benzoimidazole (obtained in Step 1, 12.66 mmol) was dissolved in 150 cm³ of ethyl-alcohol and 11.425 g $SnCl_2$ dihydrate (50.64 mmol) was added in portions. The reaction mixture was refluxed for 6 hours. Then the mixture was evaporated under reduced pressure, 100 cm³ of 2N NaOH and 70 cm³ of ethyl-acetate was added and it was stirred for 30 minutes vigorously while it was being cooled in an ice bath. The precipitated solid was filtered off on a Buchner funnel and washed well with ethyl-acetate. Filtrate was separated and extracted further three times with 70-70 cm³ ethyl-acetate. The combined organic layer was washed with brine, dried over MgSO₄, decolorized with activated carbon and evaporated to dryness. The residual solid was recrystallized from minimal amount of acetonitrile and air-dried to give the desired product as an off-white solid. Yield: 2.37 g (84%). Ret. time: 0.45-1.53 min., (M+H)⁺=224; ¹HNMR (DMSO-d₆, 300 MHz), δ (ppm): 8.32 (s, 1H), 7.65 (m, 1H), 7.46 (m, 1H), 7.22-7.15 (m, 2H), 6.96 (t, J=7.68 Hz, 1H), 6.46-6.39 (m, 3H), 5.32 (s, 2H), 5.06 (s, 2H).

Step 3:

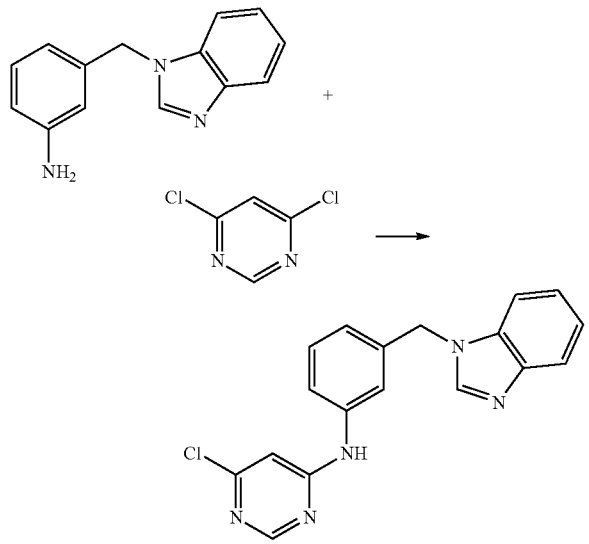

1.451 g 3-Benzoimidazol-1-ylmethyl-phenylamine (obtained in Step 2, 6.5 mmol) and 1.162 g 4,6-dichloropyrimidine (7.8 mmol) was dissolved in 70 cm³ of isopropyl-alcohol, 1.64 cm³ N,N-diisopropyl-ethylamine (1.215 g, 9.4 mmol) was added and the mixture was refluxed for five days. Then the mixture was evaporated under reduced pressure, 100 cm³ of water was added and it was extracted with 3×70 cm³ ethyl-acetate. Combined organic layer was washed with brine, dried over MgSO₄ and evaporated to a yellowish oil. The residue was crystallized from minimal amount of acetonitrile and washed with diethyl-ether to give the desired product as an off-white solid. Yield: 1.78 g (82%). For analitical results and compound identification see Table 1. The compound was used as a starting material in the preparation of Example 64-66 and 79-83.

Example 64

((1H-Benzoimidazol-2-yl)-{3-[6-(2-methoxy-phenyl)-pyrimidin-4-ylamino]-benzyl}-amine)

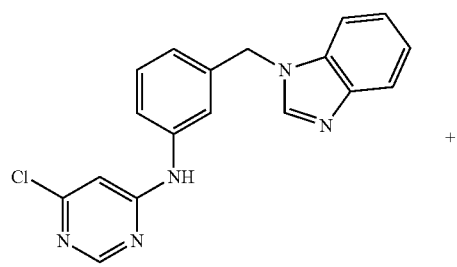

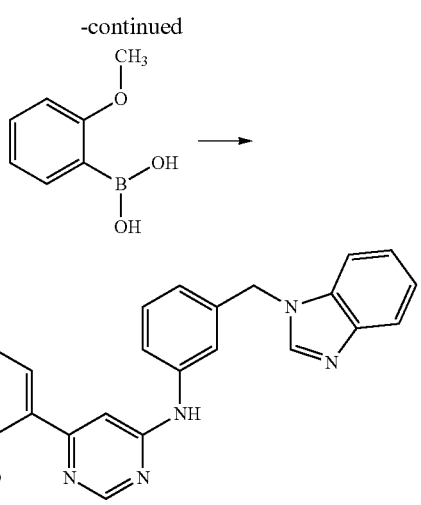

235 mg (1H-Benzoimidazol-2-yl)-[3-(6-chloro-pyrimidin-4-ylamino)-benzyl]-amine (prepared in Example 63) (0.70 mmol) was suspended in 30 cm³ dimethoxyethane and the flask was filled with argon properly. 58 mg Tetrakis(thriphenylphosphine)palladium[0] (0.05 mmol) was added and the mixture was stirred at room temperature for 30 minutes. Then 152 mg 2-methoxyphenyl-boronic acid (1 mmol), 318 mg anhydrous Na₂CO₃ (3 mmol) and 6 ml water was added. The mixture was ferluxed overnight while slow argon flow was being applied. The reaction mixture was poured to 80 cm³ 1M NaH₂PO₄ solution and it was extracted three times with 50-50 cm³ of ethyl-acetate. The combined organic layer was washed with brine, dried over MgSO₄, decolorized with activated carbon and evaporated to dryness. The residual solid was recrystallized from minimal amount of acetonitrile and air-dried to give the desired product (158 mg, 55% yield). For analitical results and compound identification see Table 1.

Example 65-66 and 79-83

Compounds were prepared according to a same manner described in Example 64 using the appropriate boronic acid and reaction time (until TLC indicates the completion of the reaction).

Yields were between 50-70%. For analitical results and compound identification see Table 1.

Example 67

(2-[3-(6-Chloro-pyrimidin-4-ylamino)-benzyl]-isoindole-1,3-dione)

Step 1:

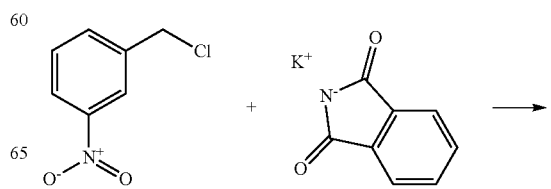

-continued

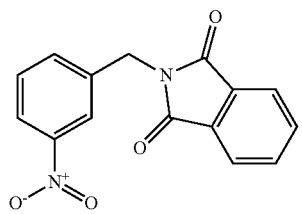

10.295 g 3-Nitrobenzyl-chloride (60 mmol) was dissolved in 100 cm³ of abs. DMF and 11.670 g phtalimide potassium salt (63 mmol) was added in small portions. The reaction mixture was stirred overnight at room temperature. Then the mixture was evaporated under reduced pressure, 150 cm³ of water and 40 cm³ of ethyl-acetate was added and it was stirred for 30 minutes vigorously. The precipitated solid was filtered off washed with ethyl-acetate and air dried. Yield: 14.420 g (85%) white powder. Ret. time: 4.00 min., (M+H)⁺=283; ¹HNMR (DMSO-$d_6$, 300 MHz), δ (ppm): 8.19 (s, 1H), 8.14 (d, J=8.16 Hz, 1H), 7.90 (m, 4H), 7.79 (d, J=7.62 Hz, 1H), 7.64 (t, J=7.98 Hz, 1H), 4.92 (s, 2H).

Step 2:

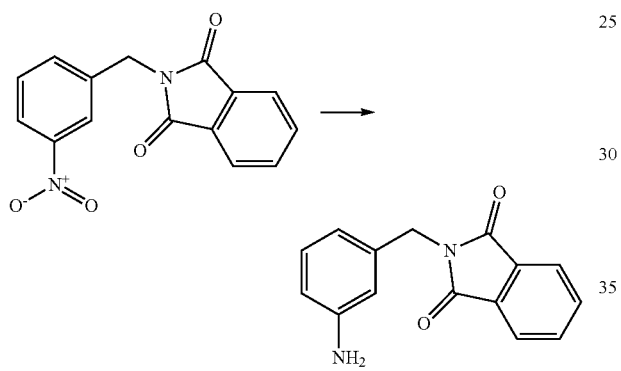

14.420 g 2-(3-Nitro-benzyl)-isoindole-1,3-dione (obtained in Step 1, 51.10 mmol) was dissolved in 250 cm³ of ethyl-alcohol and 46.108 g SnCl₂ dihydrate (204.35 mmol) was added in portions. The reaction mixture was refluxed for 6 hours. Then the mixture was evaporated under reduced pressure, 300 cm³ of 2N NaOH and 200 cm³ of ethyl-acetate was added and it was stirred for 30 minutes vigorously while it was being cooled in an ice bath. The precipitated solid was filtered off on a Buchner funnel and washed well with ethyl-acetate. Filtrate was separated and extracted further three times with 150-150 cm³ ethyl-acetate. The combined organic layer was washed with brine, dried over MgSO₄, decolorized with activated carbon and evaporated to dryness. The residual solid was recrystallized from minimal amount of acetonitrile and air-dried to give the desired product as an off-white solid. Yield: 7.950 g (62%). Ret. time: 2.42 min., (M+H)⁺=253; ¹HNMR (DMSO-$d_6$, 300 MHz), δ (ppm): 7.87 (m, 4H), 6.93 (t, J=7.62 Hz, 1H), 6.42 (m, 3H), 5.04 (bs, 2H), 4.60 (s, 2H).

Step 3:

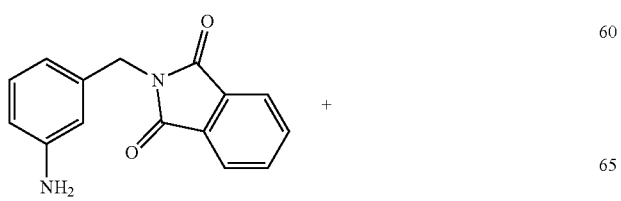

-continued

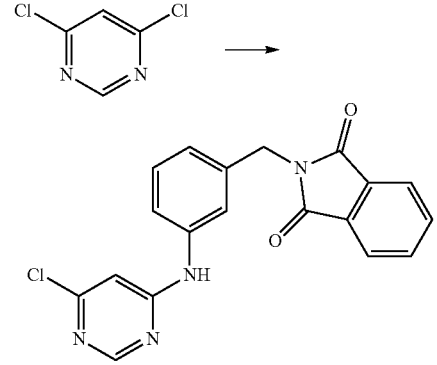

2.651 g 2-(3-Amino-benzyl)-isoindole-1,3-dione (obtained in Step 2, 10.51 mmol) and 1.879 g 4,6-dichloropyrimidine (12.61 mmol) was dissolved in 50 cm³ of isopropyl-alcohol, 2.64 cm³ N,N-diisopropyl-ethylamine (1.956 g, 15.13 mmol) was added and the mixture was refluxed for four days. The reaction mixture was cooled to room temperature and the precipitated compound was filtered off. The off-white product was washed well with diethyl-ether and air-dried. Yield: 3.630 g (95%). For analitical results and compound identification see Table 1

Example 68

(2-{3-[6-(2-Methoxy-phenyl)-pyrimidin-4-ylamino]-benzyl}-isoindole-1,3-dione)

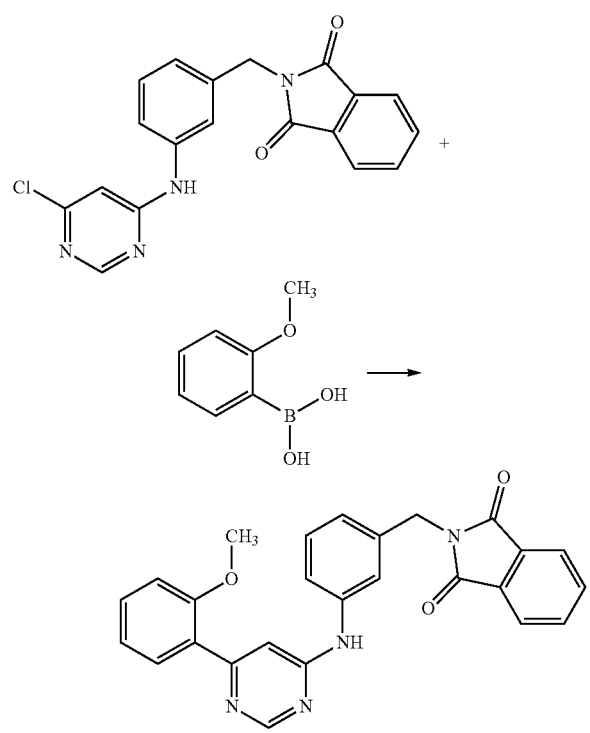

1.739 g 2-[3-(6-Chloro-pyrimidin-4-ylamino)-benzyl]-isoindole-1,3-dione (prepared in Example 67) (4.79 mmol) was suspended in 50 cm³ abs. DMF and the flask was filled with argon properly. 347 mg Tetrakis(thriphenylphosphine) palladium[0] (0.3 mmol) was added and the mixture was stirred at room temperature for 30 minutes. Then 968 mg 2-methoxyphenyl-boronic acid (6.50 mmol) and 2.123 g $K_3PO_4$ (3 mmol) was added. The mixture was ferluxed for 6 hours while slow argon flow was being applied. The reaction mixture was evaporated under reduced pressure, 150 cm³ 5% $NaHCO_3$ solution was added and it was extracted three times with 100-100 cm³ of ethyl-acetate. The combined organic layer was washed with brine, dried over $MgSO_4$, decolorized with activated carbon and evaporated under reduced pressure. The residual oil was chromatographed on silica gel eluting with chloroform containing 1% ethyl-alcohol. The residual solid was recrystallized from minimal amount of acetonitrile and air-dried to give the desired product as a yellow solid. Yield: 1.652 g (79%). For analitical results and compound identification see Table 1.

Example 69

(3-[6-(2-Methoxy-phenyl)-pyrimidin-4-ylamino]-benzyl-ammonium chloride)

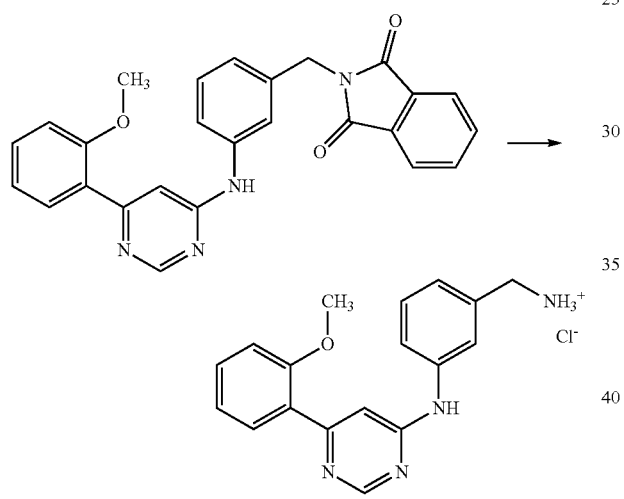

1.652 g 2-{3-[6-(2-Methoxy-phenyl)-pyrimidin-4-ylamino]-benzyl}-isoindole-1,3-dione (prepared in Example 68) (3.78 mmol) was dissolved in 100 cm³ ethyl-alcohol, 2.22 cm³ hydrazine hydrate (2.294 g 45.8 mmol) and refluxed for 2 hours. The reaction mixture was cooled to room temperature and the precipitated solid was filtered off and was washed well with ethyl-alcohol. The filtrate was evaporated to dryness and 150 cm³ 0.5 N HCl was added to the residue. The mixture was extracted well four times with 50-50 cm³ ethyl-acetate. The pH of the inorganic layer was then set to basic by addition of 5N NaOH ad then extracted well four times with 50-50 cm³ ethyl-acetate. The combined organic layer was washed with brine, dried over $MgSO_4$ and evaporated under reduced pressure. The residual oil was taken up in 50 cm³ dry ethyl acetate and 2 cm³ of ethyl acetate saturated with HCl gas was added droppwise. The precipitated solid was filtered off and washed well with diethyl-ether to obtain the desired compound as a yellow solid. Yield: 1.065 g (82%). For analitical results and compound identification see Table 1. The compound was used as a starting material in the preparation of Example 70-74, 84 and 85.

Example 70

(2,6-Dichloro-N-{3-[6-(2-methoxy-phenyl)-pyrimidin-4-ylamino]-benzyl}-benzenesulfonamide)

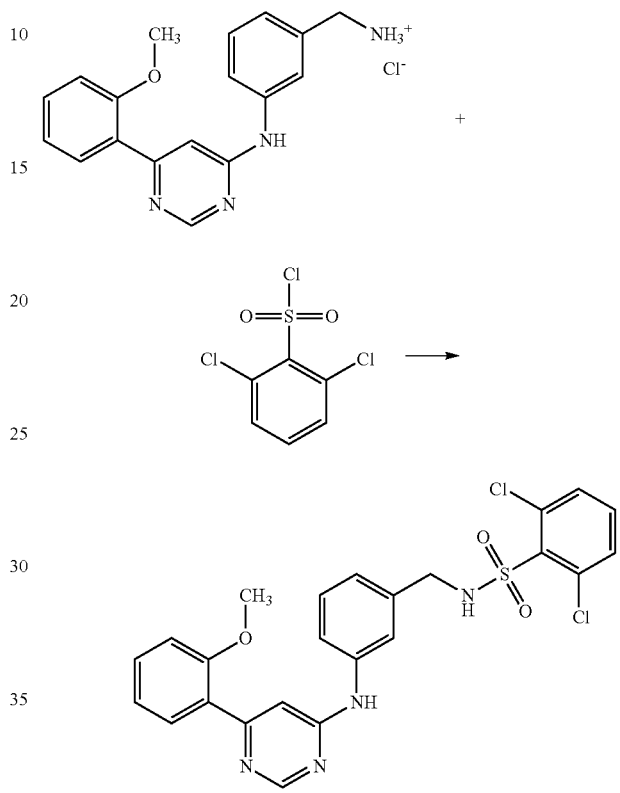

171 mg 3-[6-(2-Methoxy-phenyl)-pyrimidin-4-ylamino]-benzyl-ammonium chloride (prepared in Example 69) (0.5 mmol) was dissolved in 50 cm³ dry dichloromethane, 0.350 cm³ N,N-diisopropyl-ethylamine (259 mg, 2 mmol) was added and the mixture was cooled to 0° C. in an ice bath. After stirring it for 15 minutes 196 mg 2,6-dichlorobenzenesulfonyl-chloride (0.8 mmol) was added and the mixture was stirred for 2 hours at 0° C. and overnight at room temperature. Then 50 cm³ 5% $NaHCO_3$ solution was added and it was extracted three times with 50-50 cm³ of chloroform. The combined organic layer was washed with brine, dried over $MgSO_4$, decolorized with activated carbon and evaporated under reduced pressure. The residual solid was recrystallized from minimal amount of acetonitrile and air-dried to give the desired product as an yellow solid. Yield: 34 mg (13%). For analitical results and compound identification see Table 1.

Example 71-74, 84 and 85

Compounds were prepared according to a same manner described in Example 70 using the appropriate acid chloride or isocyanate and reaction time (until TLC indicates the completion of the reaction). Yields were between 10-60% and in some cases column chromatography was used to purify products. For analitical results and compound identification see Table 1.

Example 86

((4-Benzoimidazol-1-ylmethyl-phenyl)-(6-chloro-pyrimidin-4-yl)-amine)

Step 1:

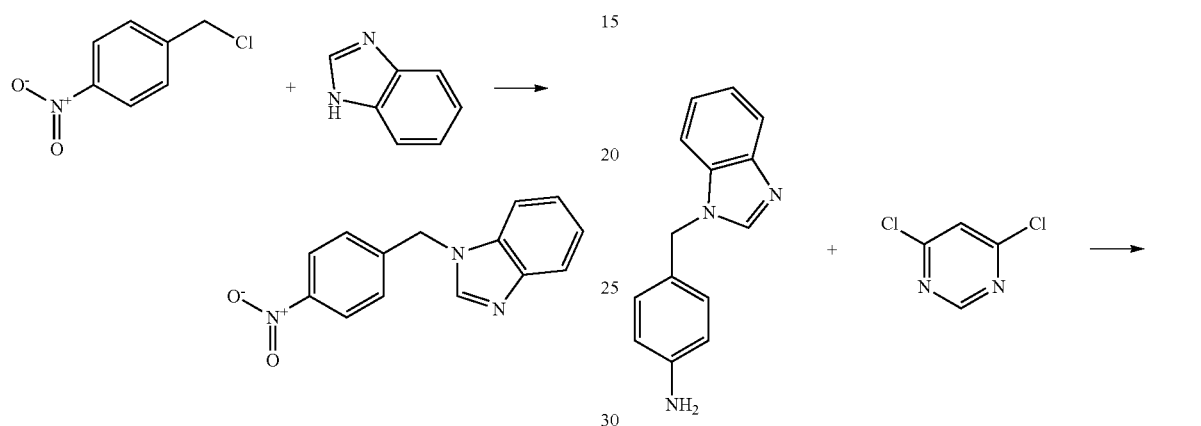

3.432 g 4-Nitrobenzyl-chloride (20 mmol) was added to a solution of 2.363 g (20 mmol) benzimidazole and 1.000 g NaH (60% in mineral oil) (25 mmol) in 50 cm$^3$ of abs. DMF at 0° C. in small portions. The reaction mixture was then stirred for additional 3 hours at room temperature. Then the mixture was evaporated under reduced pressure, 100 cm$^3$ of water was added and it was extracted with 3×70 cm$^3$ ethyl-acetate. Combined organic layer was washed with brine, dried over MgSO$_4$ and evaporated to a yellowish oil. Residue was used in the next step without any further characterization.

Step 2:

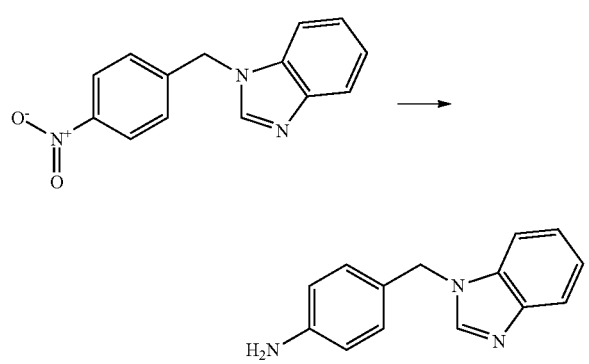

5.065 g 1-(4-Nitro-benzyl)-1H-benzoimidazole (obtained in Step 1, 20 mmol) was dissolved in 100 cm$^3$ of methyl-alcohol and 200 mg Pd catalyst (10% on activated carbon) was added. Mixture was stirred under H$_2$ atmosphere overnight. When TLC indicates the end of the reaction catalyst was filtered off and the filtrate was evaporated to dryness. The residual solid was recrystallized from minimal amount of acetonitrile and air-dried to give the desired product as an off-white solid. Overall yield for Step 1 and Step 2: 1.57 g (35%). Ret. time: 0.45-1.21 min., (M+H)$^+$=224; $^1$HNMR (DMSO-d$_6$, 300 MHz), δ (ppm): 8.30 (s, 1H), 7.62 (d, J=8.34 Hz, 1H), 7.52 (d, J=6.96 Hz, 1H), 7.19 (m, 2H), 7.04 (d, J=8.16 Hz, 2H), 7.49 (d, J=8.22 Hz, 2H), 5.25 (s, 2H), 5.08 (s, 2H).

Step 3:

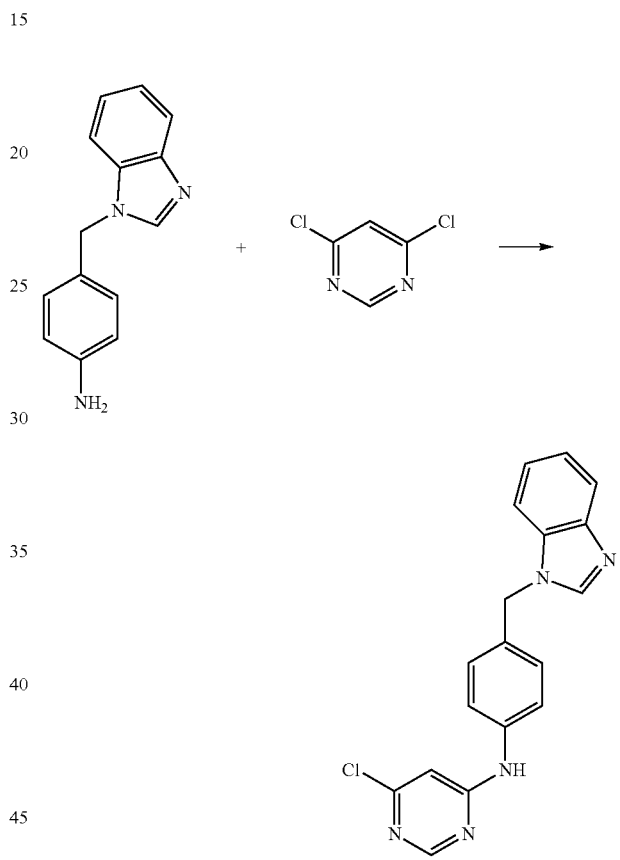

1.442 g 4-Benzoimidazol-1-ylmethyl-phenylamine (obtained in Step 2, 6.4 mmol) and 1.058 g 4,6-dichloropyrimidine (7.1 mmol) was dissolved in 50 cm$^3$ of isopropyl-alcohol, 1.69 cm$^3$ N,N-diisopropyl-ethylamine (1.252 g, 9.7 mmol) was added and the mixture was refluxed for five days. Then the mixture was evaporated under reduced pressure, 100 cm$^3$ of water was added and it was extracted with 3×70 cm$^3$ ethyl-acetate. Combined organic layer was washed with brine, dried over MgSO$_4$ and evaporated to a yellowish oil. The residue was crystallized from minimal amount of acetonitrile and washed with diethyl-ether to give the desired product as an off-white solid. Yield: 1.33 g (61%). For analitical results and compound identification see Table 1. The compound was used as a starting material in the preparation of Example 87-89.

Example 87

((1H-Benzoimidazol-2-yl)-{4-[6-(2-methoxy-phenyl)-pyrimidin-4-ylamino]-benzyl}-amine)

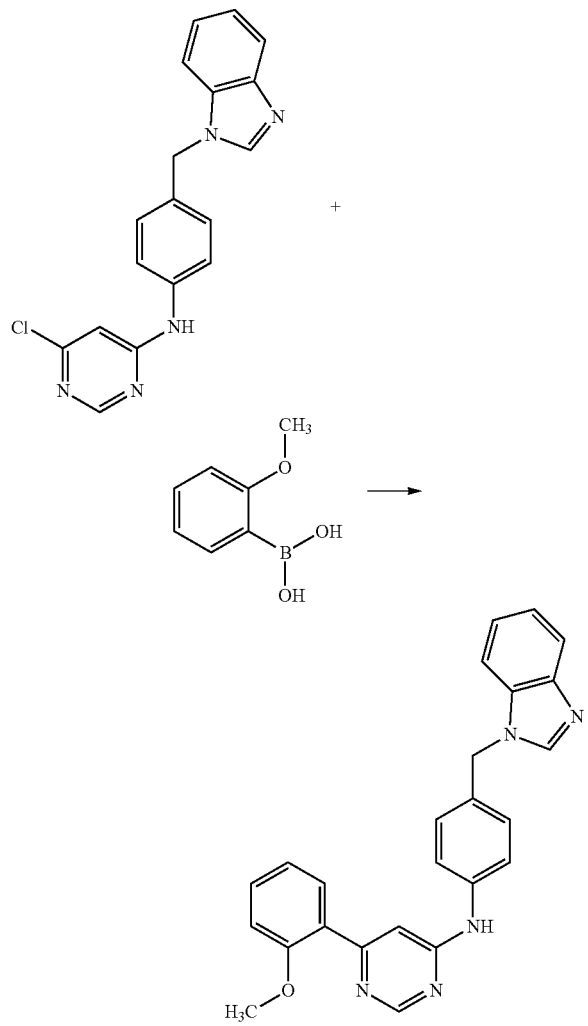

235 mg (1H-Benzoimidazol-2-yl)-[4-(6-chloro-pyrimidin-4-ylamino)-benzyl]-amine (prepared in Example 86) (0.70 mmol) was suspended in 30 cm³ dimethoxyethane and the flask was filled with argon properly. 58 mg Tetrakis(thriphenylphosphine) palladium[0] (0.05 mmol) was added and the mixture was stirred at room temperature for 30 minutes. Then 152 mg 2-methoxyphenyl-boronic acid (1 mmol), 318 mg anhydrous Na₂CO₃ (3 mmol) and 6 ml water were added. The mixture was refluxed overnight while slow argon flow was being applied. The reaction mixture was poured to 80 cm³ 1M NaH₂PO₄ solution and it was extracted three times with 50-50 cm³ of ethyl-acetate. The combined organic layer was washed with brine, dried over MgSO₄, decolorized with activated carbon and evaporated to dryness. The residual solid was recrystallized from minimal amount of acetonitrile and air-dried to give the desired product (125 mg, 44% yield). For analitical results and compound identification see Table 1.

Example 88 and 89

Compounds were prepared according to a same manner described in Example 87 using the appropriate boronic acid and reaction time (until TLC indicates the completion of the reaction). Yields were between 50-70%. For analitical results and compound identification see Table 1.

Example 90

((6-Chloro-pyrimidin-4-yl)-(3-indol-1-ylmethyl-phenyl)-amine)

Step 1:

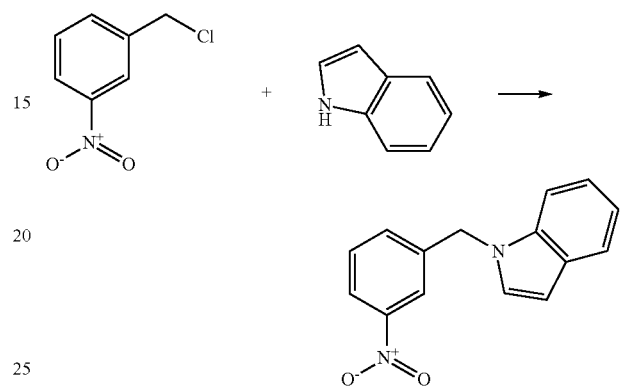

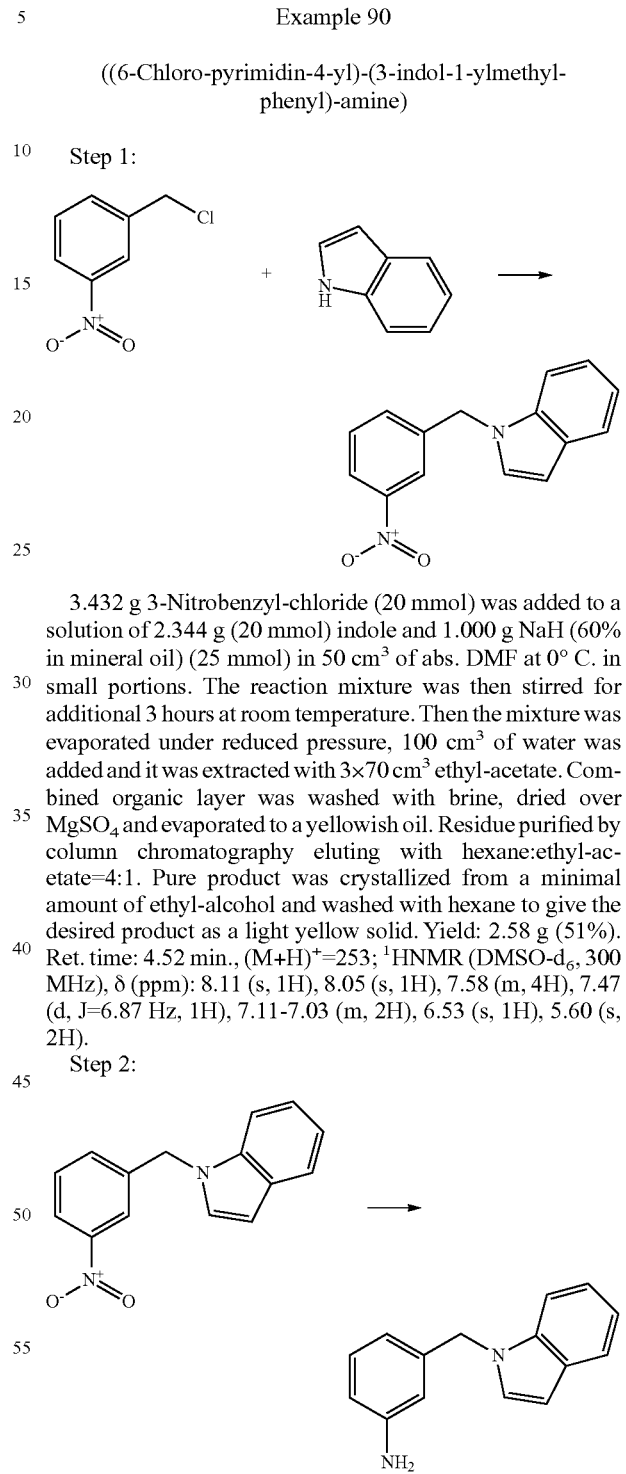

3.432 g 3-Nitrobenzyl-chloride (20 mmol) was added to a solution of 2.344 g (20 mmol) indole and 1.000 g NaH (60% in mineral oil) (25 mmol) in 50 cm³ of abs. DMF at 0° C. in small portions. The reaction mixture was then stirred for additional 3 hours at room temperature. Then the mixture was evaporated under reduced pressure, 100 cm³ of water was added and it was extracted with 3×70 cm³ ethyl-acetate. Combined organic layer was washed with brine, dried over MgSO₄ and evaporated to a yellowish oil. Residue purified by column chromatography eluting with hexane:ethyl-acetate=4:1. Pure product was crystallized from a minimal amount of ethyl-alcohol and washed with hexane to give the desired product as a light yellow solid. Yield: 2.58 g (51%). Ret. time: 4.52 min., (M+H)⁺=253; ¹HNMR (DMSO-d₆, 300 MHz), δ (ppm): 8.11 (s, 1H), 8.05 (s, 1H), 7.58 (m, 4H), 7.47 (d, J=6.87 Hz, 1H), 7.11-7.03 (m, 2H), 6.53 (s, 1H), 5.60 (s, 2H).

Step 2:

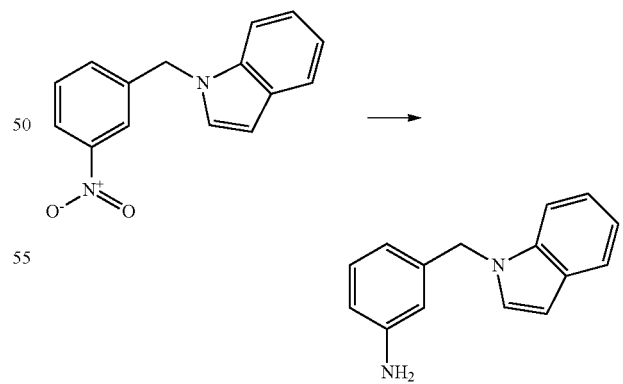

1.222 g 1-(3-Nitro-benzyl)-1H-indole (obtained in Step 1, 4.84 mmol) was dissolved in 60 cm³ of ethyl-alcohol and 4.372 g SnCl₂ dihydrate (19.38 mmol) was added in portions. The reaction mixture was refluxed for 6 hours. Then the mixture was evaporated under reduced pressure, 80 cm³ of 2N NaOH and 50 cm³ of ethyl-acetate were added and it was stirred for 30 minutes vigorously while it was being cooled in an ice bath. The precipitated solid was filtered off on a Buchner funnel and washed well with ethyl-acetate. Filtrate was separated and extracted further three times with 70-70 cm³ ethyl-acetate. The combined organic layer was washed with brine, dried over MgSO₄, decolorized with activated carbon and evaporated under reduced pressure. Residue was used in the next step without any further characterization.

Step 3:

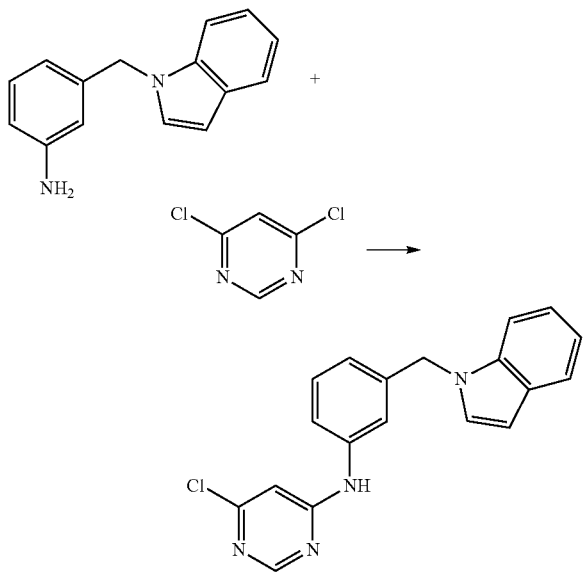

1.077 g 3-Indol-1-ylmethyl-phenylamine (obtained in Step 2, 4.84 mmol) and 0.722 g 4,6-dichloropyrimidine (4.84 mmol) was dissolved in 50 cm³ of isopropyl-alcohol, 1.27 cm³ N,N-diisopropyl-ethylamine (0.939 g, 7.27 mmol) were added and the mixture was refluxed for three days. Then the mixture was evaporated under reduced pressure, 100 cm³ of water was added and it was extracted with 3×70 cm³ ethyl-acetate. Combined organic layer was washed with brine, dried over MgSO₄ and evaporated to a yellowish oil. The residue was crystallized from minimal amount of acetonitrile and washed with diethyl-ether to give the desired product as an off-white solid. Overall yield for Step 2 and Step 3: 1.015 g (63%). For analitical results and compound identification see Table 1. The compound was used as a starting material in the preparation of Example 91.

Example 91

((3-Indol-1-ylmethyl-phenyl)-[6-(2-methoxy-phenyl)-pyrimidin-4-yl]-amine)

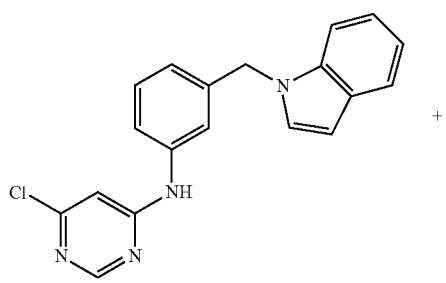

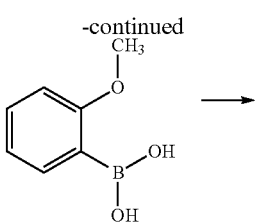

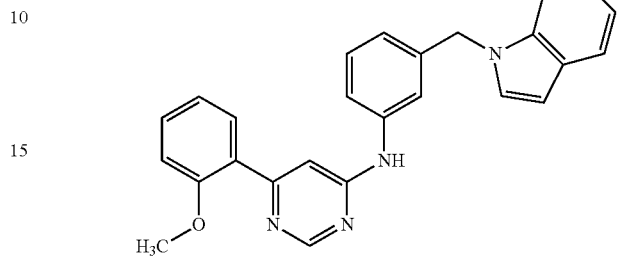

234 mg (6-Chloro-pyrimidin-4-yl)-(3-indol-1-ylmethyl-phenyl)-amine (pre-pared in Example 90) (0.70 mmol) was suspended in 30 cm³ dimethoxyethane and the flask was filled with argon properly. 58 mg Tetrakis(thriphenylphosphine) palladium[0] (0.05 mmol) was added and the mixture was stirred at room temperature for 30 minutes. Then 152 mg 2-methoxyphenyl-boronic acid (1 mmol), 318 mg anhydrous Na₂CO₃ (3 mmol) and 6 ml water were added. The mixture was ferluxed overnight while slow argon flow was being applied. The reaction mixture was poured to 80 cm³ 1M NaH₂PO₄ solution and it was extracted three times with 50-50 cm³ of ethyl-acetate. The combined organic layer was washed with brine, dried over MgSO₄, decolorized with activated carbon and evaporated to dryness. The residual solid was recrystallized from minimal amount of acetonitrile and air-dried to give the desired product (90 mg, 32% yield). For analitical results and compound identification see Table 1.

Example 92

((6-Chloro-pyrimidin-4-yl)-[3-(2-morpholin-4-ylm-ethyl-benzo-imidazol-1-ylmethyl)-phenyl]-amine)

Step 1:

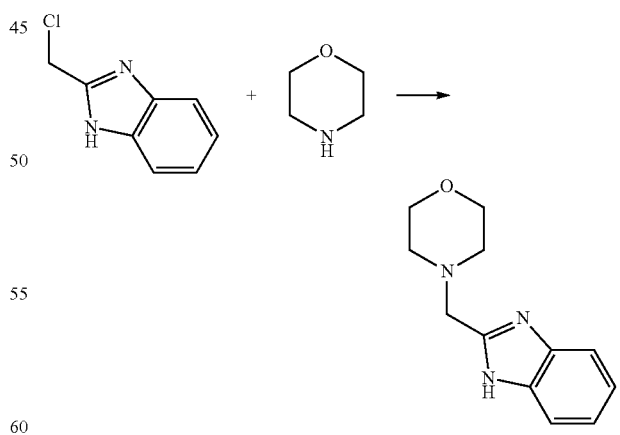

2.00 g 2-Chloromethylbenzimidazole (12 mmol) was added in portions to the solution of 5.25 cm³ morpholine (5.223 g, 60 mmol) in 50 cm³ acetonitrile at room temperature. Mixture was refluxed until TLC indicates the end of the reaction. The reaction mixture was evaporated under reduced pressure and 100 cm³ of water was added and it was extracted with 3×70 cm³ ethyl-acetate. Combined organic layer was washed with brine, dried over MgSO₄ and evaporated to dryness. Residue was recrystallized from 15 cm³ acetonitrile. Pure product was filtered off as a white solid washed with diethyl-ether and air-dried. Yield: 2.015 g (77%). Ret. time: 0.45-1.53 min., (M+H)⁺=218 (M−H)⁻=216; ¹HNMR (DMSO-d₆, 300 MHz), δ (ppm): 12.27 (s, 1H), 7.54 (d, J=7.35 Hz, 1H), 7.43 (d, J=7.05 Hz, 1H), 7.13 (m, 2H), 3.714 (s, 2H), 3.60 (t, 4H), 2.45 (t, 4H).

Step 2:

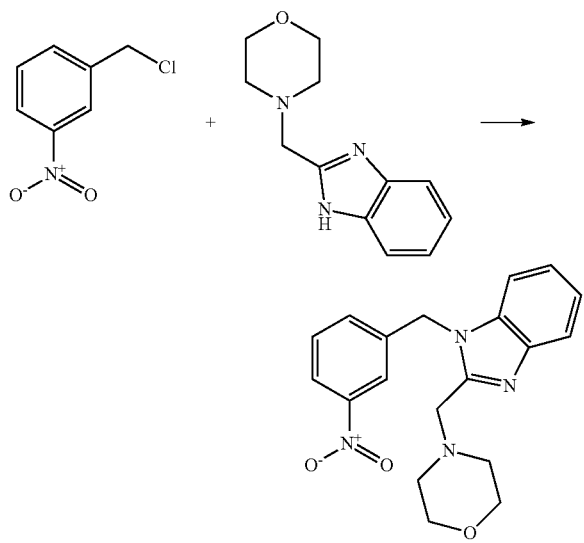

0.686 g 3-Nitrobenzyl-chloride (4 mmol) was added to a solution of 0.869 g (20 mmol) 2-morpholin-4-ylmethyl-1H-benzoimidazole (obtained in Step 1) and 0.200 g NaH (60% in mineral oil) (25 mmol) in 10 cm³ of abs. DMF at 0° C. in small portions. The reaction mixture was then stirred for additional 3 hours at room temperature. Then the mixture was evaporated under reduced pressure, 50 cm³ of water was added and it was extracted with 3×50 cm³ ethyl-acetate. Combined organic layer was washed with brine, dried over MgSO₄ and evaporated to a yellowish oil. Residue purified by column chromatography eluting with hexane:ethyl-acetate=1:1. Pure product was crystallized from a minimal amount of acetonitrile and washed with diethyl-ether to give the desired product as an off-white solid. Yield: 0.642 g (46%). Ret. time: 2.71 min., (M+H)⁺=353; ¹HNMR (DMSO-d₆, 300 MHz), δ (ppm): 8.16-8.12 (m, 1H), 8.06 (s, 1H), 7.66-7.61 (m, 3H), 7.43 (m, 1H), 7.20 (m, 2H), 5.73 (s, 2H), 3.78 (s, 2H), 3.32 (m, 4H), 2.39 (m, 4H).

Step 3:

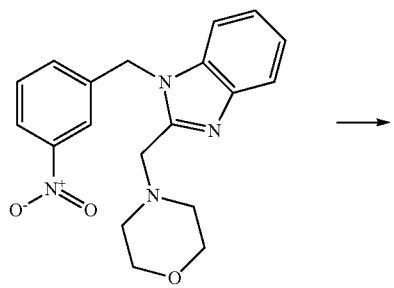

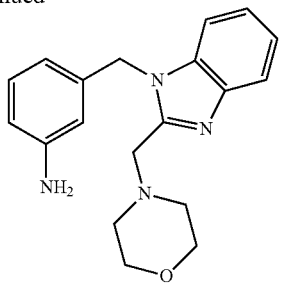

0.610 g 2-Morpholin-4-ylmethyl-1-(3-nitro-benzyl)-1H-benzoimidazole (obtained in Step 2, 1.73 mmol) was dissolved in 50 cm³ of ethyl-alcohol and 1.562 g SnCl₂ dihydrate (6.92 mmol) was added in portions. The reaction mixture was refluxed for 6 hours. Then the mixture was evaporated under reduced pressure, 80 cm³ of 2N NaOH and 50 cm³ of ethyl-acetate were added and it was stirred for 30 minutes vigorously while it was being cooled in an ice bath. The precipitated solid was filtered off on a Buchner funnel and washed well with ethyl-acetate. Filtrate was separated and extracted further three times with 70-70 cm³ ethyl-acetate. The combined organic layer was washed with brine, dried over MgSO₄ and evaporated under reduced pressure to a dark yellow solid. Pure product was crystallized from a minimal amount of acetonitrile and washed with diethyl-ether to give the desired product as an off-white solid. Yield: 0.510 g (91%). Ret. time: 0.45-1.93 min., (M+H)⁺=323; ¹HNMR (DMSO-d₆, 300 MHz), δ (ppm): 7.60 (m, 1H), 7.40 (m, 1H), 7.17 (m, 2H), 6.94 (t, 1H), 6.42 (d, J=7.89 Hz, 1H), 6.21 (d, J=7.35 Hz, 1H), 6.26 (s, 1H), 5.43 (s, 2H), 5.03 (s, 2H), 3.71 (s, 2H), 3.47 (bs, 4H), 2.40 (bs, 4H).

Step 4:

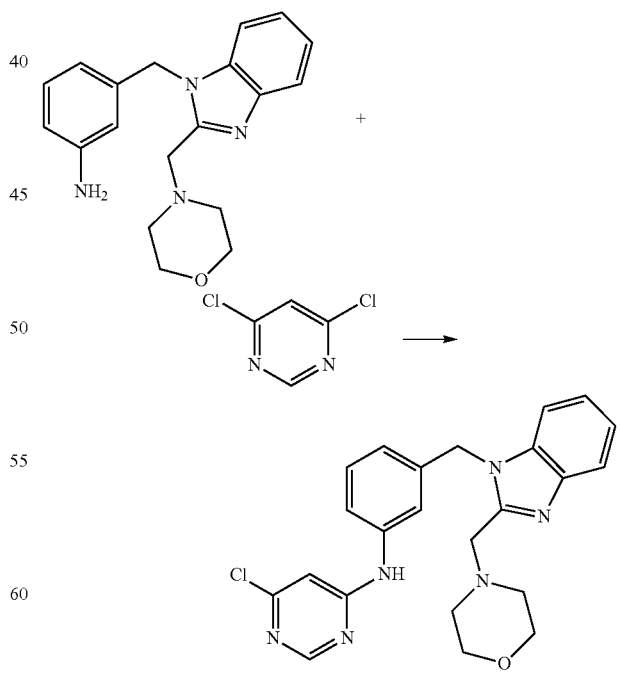

1.12 g 3-(2-Morpholin-4-ylmethyl-benzoimidazol-1-ylmethyl)-phenylamine (obtained in Step 3, 3.48 mmol) and 0.622 g 4,6-dichloropyrimidine (4.16 mmol) was dissolved in 60 cm³ of isopropyl-alcohol, 0.91 cm³ N,N-diisopropyl-ethylamine (0.674 g, 5.22 mmol) was added and the mixture was refluxed for four days. Then the mixture was evaporated under reduced pressure, 100 cm³ of water was added and it was extracted with 3×70 cm³ ethyl-acetate. Combined organic layer was washed with brine, dried over MgSO₄ and evaporated to an oil. Residue purified by column chromatography eluting with chloroform:methanol=10:1. Residual oil was taken up in 40 cm³ dry ethyl-acetate and 1 cm³ of 2-propanol (saturated with HCl) was added. Mixture was stirred at 0° C. for 30 minutes and the precipitated solid was filtered off, washed well with ethyl-acetate and dried in vacuum. The hydrochloride salt of the desired product was obtained as a light pink solid. Yield: 1.46 g (89%). For analitical results and compound identification see Table 1. The compound was used as a starting material in the preparation of Example 93 and 94.

Example 93

([6-(2-Methoxy-phenyl)-pyrimidin-4-yl]-[3-(2-morpholin-4-ylmethyl-benzoimidazol-1-ylmethyl)-phenyl]-amine)

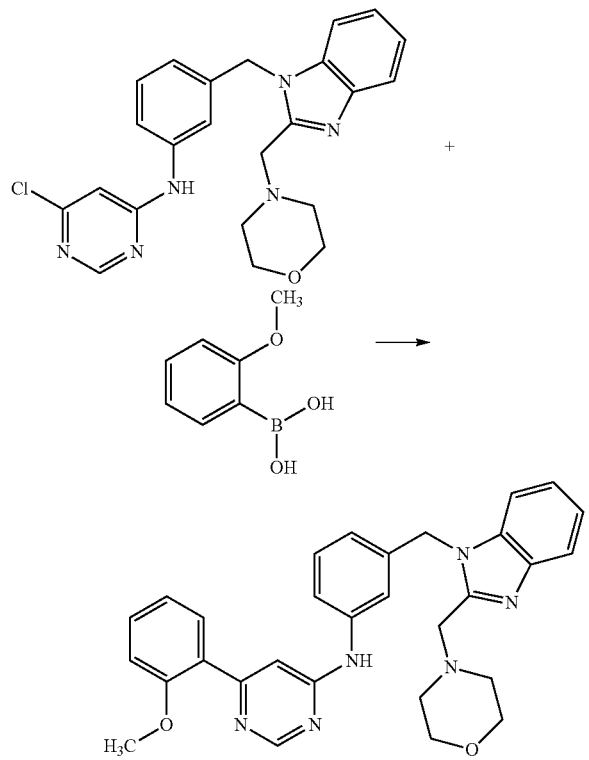

330 mg (6-Chloro-pyrimidin-4-yl)-[3-(2-morpholin-4-ylmethyl-benzoimidazol-1-ylmethyl)-phenyl]-amine (prepared in Example 92) (0.70 mmol) was suspended in 30 cm³ dimethoxyethane and the flask was filled with argon properly. 58 mg Tetrakis(triphenylphosphine) palladium[0] (0.05 mmol) was added and the mixture was stirred at room temperature for 30 minutes. Then 152 mg 2-methoxyphenyl-boronic acid (1 mmol), 424 mg anhydrous Na₂CO₃ (4 mmol) and 6 ml water were added. The mixture was ferluxed overnight while slow argon flow was being applied. The reaction mixture was poured to 80 cm³ 1M NaH₂PO₄ solution and it was extracted three times with 50-50 cm³ of ethyl-acetate. The combined organic layer was washed with brine, dried over MgSO₄, decolorized with activated carbon and evaporated to dryness. The residual solid was recrystallized from minimal amount of acetonitrile and air-dried to give the desired product (132 mg, 37% yield). For analitical results and compound identification see Table 1.

Example 94

Compounds were prepared according to a same manner described in Example 93 using the appropriate boronic acid and reaction time (until TLC indicates the completion of the reaction). Yield is 19%. For analitical results and compound identification see Table 1.

B) Test Examples

Analitical Methods (HPLC-MS, NMR)
Waters HPLC/MS:
MS detector: Waters SQD
UV detector: Waters 996 DAD
Separation module: Waters Alliance 2795
HPLC:
Column: Waters XBridge C18, 5 cm×4.6 mm, 3.5 µm.
Solvent A: Water/0.1% HCOOH
Solvent B: AcCN
Acetonitrile: Riedel-deHaën; G Chromasolv (34998)
Water: Mili-Q Academic
Formic Acid Riedel-deHaën; extra pure (27001)
Flow Rate: 2 ml/min
Gradient:

| min | B % |
|---|---|
| 0.00 | 5 |
| 0.50 | 5 |
| 5.50 | 95 |
| 6.00 | 95 |
| 6.50 | 5 |
| 7.00 | 5 |

Injection: 5 µg
MS:
Ionization: ES+/ES−
Source block temp: 110° C.
Desolvation temp: 250° C.
Desolvation Gas: 500 L/h
Cone Gas: 80 Uh
Capillary: 3000 V
Cone: 30 V
Extractor: 6 V
Rf Lens: 0.1 V
Scan: 80 to 1000 m/z in 1 sec.
Inter-scan delay: 0.1 s
¹H NMR spectra were recorded on a Brucker Avanve 300 MHz AV spectrometer in deuterated solvents (DMSO-d₆). Chemical shifts δ are in parts per million (ppm).

In Vitro CDK9/CyclinT Assay

The activity of the compounds described in the present invention can be determined by the following kinase assay, which measures the phosphorylation of a fluorescently-labeled peptide by human CDK9/CyclinT kinase complex by fluorescent polarization using a commercially available IMAP Screening Express Assay Kit (Molecular devices).

CDK9 kinase assays were performed in low protein binding 384-well plates (Corning 3676). Test compounds were diluted in 100% DMSO to 5 mM stock concentration, then further dilutions were made in H₂O or 100% DMSO to desirable concentrations.

Each reaction consisted of 5 nM enzyme: CDK9/CyclinT (Proqinase cat#0371-0345-1), 400 nM TAMRA-Rbtide (synthetic 15-mer peptide derived from human retinoblastoma tumor suppressor protein labelled with TAMRA dye, Genecust Europe), 12 μM ATP (=$Km_{app}$, Sigma-Aldrich) and kinase buffer: 20 mM MOPS pH 7 (Sigma-Aldrich), 1 mM DTT (Sigma-Aldrich), 10 mM MgCl₂ (Sigma-Aldrich), 0.01% Tween 20 (Sigma-Aldrich).

For each reaction, 4 or 6 μl containing TAMRA-Rbtide, ATP and kianse buffer were combined with 2 μl diluted compound in H₂O or 0.028 μl compound in 100% DMSO. The kinase reaction was started by the addition of 2 μl diluted enzyme. The reaction was allowed to run for 1 hours at room temperature. The reaction was stopped by adding 15 μl IMAP beads (1:400 beads in progressive (100% buffer A) 1× buffer). After an additional 1 hours, fluorescent polarization (Ex: 550-10 nm, Em: 590-10 nm, Dich: 561 nm) was measured using an Analyst GT (Molecular devices).

Results are given in Table 1 as follows:

TABLE 1

| No. | Ret. Time (min) | ESI-MS | NMR | CDK9 inhibitory range |
|---|---|---|---|---|
| 1 | 2.81 | (M + H)+ = 313<br>(M − H)− = 311 | 9.89 (s, 1H), 8.47 (s, 1H), 7.580 (m, 3H), 7.34 (t, J = 7.80 Hz, 1H), 7.63 (d, J = 7.62 Hz, 1H), 6.81 (s, 1H), 4.16 (d, J = 6.33 Hz, 2H), 2.89 (s, 3H). | D |
| 2 | 2.92 | (M + H)+ = 461<br>(M − H)− = 459 | 9.63 (s, 1H), 8.70 (s, 1H), 7.84 (d, J = 6.54 Hz, 1H), 7.64 (d, J = 8.13 Hz, 1H), 7.53 (m, 2H), 7.40 (m, 9H), 7.19 (d, J = 8.34 Hz, 1H), 7.08 (t, J = 7.47 Hz, 1H), 7.01 (d, J = 7.56 Hz, 1H), 5.27 (s, 2H), 4.14 (d, J = 5.85 Hz, 2H), 2.88 (s, 3H). | B |
| 3 | 2.72 | (M + H)+ = 381<br>(M − H)− = 379 | 9.62 (s, 1H), 8.65 (s, 1H), 7.64 (m, 2H), 7.54 (t, J = 6.30 Hz, 1H), 7.45 (m, 5H), 7.28 (t, J = 7.86 Hz, 1H), 7.00 (d, J = 7.82 Hz, 1H), 6.63 (s, 1H), 6.25 (s, 1H), 5.61 (s, 1H), 4.13 (d, J = 6.27 Hz, 2H), 2.97 (s, 3H) | C |
| 4 | 3.17 | (M + H)+ = 447<br>(M − H)− = 445 | 9.68 (s, 1H), 8.68 (s, 1H), 8.04 (d, J = 6.72 Hz, 1H), 7.63 (d, J = 8.34 Hz, 1H), 7.40 (m, 8H), 7.13 (t, J = 7.35 Hz, 1H), 6.99 (m, 4H), 4.12 (s, 2H), 2.87 (s, 3H). | B |
| 5 | 2.48 | (M + H)+ = 399<br>(M − H)− = 397 | 9.61 (s, 1H), 8.68 (s, 1H), 7.94 (dd, J1 = 7.68 Hz, J2 = 1.41 Hz, 1H), 7.70 (d, J = 8.34 Hz, 1H), 7.59 (s, 1H), 7.56 (s, 1H), 7.48 (s, 1H), 7.42 (m, 1H), 7.32 (t, J = 7.80 Hz, 1H), 7.15 (d, J = 8.25 Hz, 1H), 7.05 (m, 2H), 4.15 (M, 4H), 2.89 (s, 3H), 1.38 (t, J = 6.90 Hz, 3H). | A |
| 6 | 2.31 | (M + H)+ = 385<br>(M − H)− = 383 | 9.65 (s, 1H), 8.69 (s, 1H), 7.95 (d, J = 7.62 Hz, 1H), 7.71 (d, J = 8.07 Hz, 1H), 7.84 (s, 1H), 7.56 (bs, 1H), 7.46 (m, 2H), 7.32 (t, J = 7.74 Hz, 1H), 7.17 (d, J = 8.34 Hz, 1H), 7.08 (t, J = 7.44 Hz, 1H), 7.00 (d, J = 7.50 Hz, 1H), 4.16 (s, 2H), 3.90 (s, 3H), 2.89 (s, 3H). | A |
| 7 | 2.47 | (M + H)+ = 403<br>(M − H)− = 401 | 9.66 (s, 1H), 8.67 (s, 1H), 8.03 (dd, J1 = 8.61 Hz, J2 = 1.23 Hz, 1H), 7.70 (d, J = 8.13 Hz, 1H), 7.63 (s, 1H), 7.56 (bs, 1H), 7.45 (s, 1H), 7.32 (t, J = 7.77 Hz, 1H), 7.09 (dd, J1 = 11.43 Hz, J2 = 2.28 Hz, 1H), 7.00 (d, J = 7.47 Hz, 1H), 6.91 (m, 1H), 4.16 (s, 2H), 3.93 (s, 3H), 2.89 (s, 3H). | A |
| 8 | 2.65 | (M + H)+ = 413<br>(M − H)− = 411 | 9.60 (s, 1H), 8.67 (s, 1H), 7.91 (m, 1H), 7.59 (d, J = 8.10 Hz, 1H), 7.58 (m, 2H), 7.46 (s, 1H), 7.36 (m, 1H), 7.32 (t, J = 7.75 Hz, 1H), 7.16 (d, J = 8.28 Hz, 1H), 7.04 (m, 2H), 4.70 (m, 1H), 4.16 (s, 2H), 2.86 (s, 3H), 1.30 (d, J = 6.00 Hz, 6H). | B |
| 9 | 2.60 | (M + H)+ = 403<br>(M − H)− = 401 | 9.72 (s, 1H), 8.70 (s, 1H), 7.77 (dd, J1 = 9.99 Hz, J2 = 3.18 Hz, 1H), 7.71 (d, J = 8.31 Hz, 1H), 7.64 (s, 1H), 7.57 (m, 2H), 7.33 (m, 2H), 7.22 (m, 1H), 7.01 (d, J = 7.53 Hz, 1H), 2.09 (d, J = 6.24 Hz, 2H), 3.91 (s, 3H), 2.89 (s, 3H). | B |
| 10 | 2.99 | (M + H)+ = 479<br>(M − H)− = 477 | 9.64 (s, 1H), 8.70 (s, 1H), 7.85 (dd, J1 = 7.68 Hz, J2 = 1.38 Hz, 1H), 7.64 (d, J = 7.98 Hz, 1H), 7.58 (s, 1H), 7.47 (m, 5H), 7.30 (t, J = 7.80 Hz, 1H), 7.20 (m, 3H), 7.08 (t, J = 7.50 Hz, 1H), 7.01 (d, J = 7.59 Hz, 1H), 5.25 (s, 2H), 4.15 (s, 2H), 2.88 (s, 3H). | B |
| 11 | 2.44 | (M + H)+ = 369<br>(M − H)− = 367 | 9.65 (s, 1H), 8.68 (s, 1H), 7.67 (d, J = 8.10 Hz, 1H), 7.61 (s, 1H), 7.55 (bs, 1H), 7.41 (d, J = 7.38 Hz, 1H), 7.31 (m, 4H), 7.00 (d, J = 7.56 Hz, 1H), 6.86 (s, 1H), 4.15 (s, 2H), 2.87 (s, 3H), 2.37 (s, 3H) | C |

TABLE 1-continued

| No. | Ret. Time (min) | ESI-MS | NMR | CDK9 inhibitory range |
|---|---|---|---|---|
| 12 | 2.67 | (M + H)+ = 383 (M − H)− = 381 | 9.67 (s, 1H), 8.67 (s, 1H), 7.68 (d, J = 8.16 Hz, 1H), 7.32 (m, 5H), 7.00 (d, J = 7.56 Hz, 1H), 6.82 (s, 1H), 4.15 (s, 2H), 2.87 (s, 3H), 2.71 (m, 2H), 1.09 (t, J = 7.47 Hz, 3H). | B |
| 13 | 2.39 | (M + H)+ = 403 (M − H)− = 401 | 9.65 (s, 1H), 8.66 (s, 1H), 7.66 (d, J = 7.74 Hz, 1H), 7.59 (s, 1H), 7.55 (bs, 1H), 7.44 (m, 1H), 7.31 (t, J = 7.71 Hz, 1H), 6.99 (m, 2H), 6.90 (t, J = 8.91 Hz, 1H), 6.80 (s, 1H), 4.14 (s, 2H), 3.76 (s, 3H), 2.87 (s, 3H). | A |
| 14 | 2.87 | (M + H)+ = 431 (M − H)− = 429 | 9.59 (s, 1H), 8.64 (s, 1H), 7.99 (t, J = 8.67 Hz, 1H), 7.67 (d, J = 7.74 Hz, 1H), 7.55 (s, 2H), 7.42 (s, 1H), 7.03 (m, 2H), 6.84 (m, 1H), 4.75 (m, 1H), 4.14 (s, 2H), 2.87 (s, 3H), 1.30 (d, J = 5.91 Hz, 6H). | B |
| 15 | 3.28 | (M + H)+ = 439 (M − H)− = 437 | 9.81 (s, 1H), 8.72 (s, 1H), 7.86 (dd, J1 = 7.44 Hz, J2 = 1.62 Hz, 1H), 7.69 (d, J = 8.46 Hz, 1H), 7.57 (m, 5H), 7.32 (t, J = 7.80 Hz, 1H), 7.10 (s, 1H), 7.02 (d, J = 7.50 Hz, 1H), 4.15 (s, 2H), 2.89 (s, 3H). | C |
| 16 | 2.79 | (M + H)+ = 373 (M − H)− = 371 | 9.79 (s, 1H), 8.72 (s, 1H), 8.09 (t, J = 8.55 Hz, 1H), 7.70 (d, J = 7.45 Hz, 1H), 7.63 (s, 1H), 7.50 (m, 2H), 7.31 (m, 4H), 7.00 (d, J = 7.55 Hz, 1H), 4.15 (s, 2H), 2.98 (s, 3H). | C |
| 17 | 3.11 | (M + H)+ = 391 (M − H)− = 389 | 9.80 (s, 1H), 8.71 (s, 1H), 8.15 (m, 1H), 7.69 (d, J = 7.92 Hz, 1H), 7.63 (s, 1H), 7.55 (bs, 1H), 7.31 (m, 4H), 7.01 (d, J = 7.44 Hz, 1H), 4.15 (s, 2H), 2.88 (s, 3H). | C |
| 18 | 3.12 | (M + H)+ = 423 (M − H)− = 421 | 9.79 (s, 1H), 8.67 (s, 1H), 7.86 (d, J = 7.71 Hz, 1H), 7.77 (t, J = 7.35 Hz, 1H), 7.69 (m, 2H), 7.57 (m, 3H), 7.32 (t, J = 7.77 Hz, 1H), 7.02 (d, J = 7.50 Hz, 1H), 6.84 (s, 1H), 4.15 (s, 2H), 2.87 (s, 3H). | D |
| 19 | 2.53 | (M + H)+ = 385 (M − H)− = 383 | 9.62 (s, 1H), 8.65 (s, 1H), 7.98 (d, J = 8.85 Hz, 2H), 7.66 (d, J = 8.16 Hz, 1H), 7.62 (s, 1H), 7.26 (bs, 1H), 7.30 (t, J = 7.77 Hz, 1H), 7.17 (s, 1H), 7.06 (d, J = 8.85 Hz, 2H), 7.00 (d, J = 7.59 Hz, 1H), 4.15 (s, 2H), 3.82 (s, 3H), 2.88 (s, 3H). | C |
| 20 | 2.26 | (M + H)+ = 398 (M − H)− = 396 | 9.76 (s, 1H), 8.73 (s, 1H), 8.52 (s, 1H), 8.14 (m, 2H), 7.99 (d, J = 7.59 Hz, 1H), 7.70 (d, J = 8.16 Hz, 1H), 7.62 (m, 3H), 7.46 (bs, 1H), 7.32 (m, 2H), 7.01 (d, J = 7.53 Hz, 1H), 4.15 (d, J = 6.24 Hz, 2H), 2.88 (s, 3H). | C |
| 21 | 2.54 | (M + H)+ = 355 (M − H)− = 353 | 9.70 (s, 1H), 8.70 (s, 1H), 8.01 (m, 2H), 7.67 (d, J = 8.31 Hz, 1H), 7.63 (s, 1H), 7.56 (bs, 1H), 7.52 (m, 3H), 7.31 (t, J = 7.77 Hz, 1H), 7.25 (s, 1H), 7.01 (d, J = 7.50 Hz, 1H), 4.16 (s, 2H), 2.88 (s, 3H). | C |
| 22 | 2.10 | (M + H)+ = 370 (M − H)− = 368 | 9.66 (s, 1H), 8.65 (s, 1H), 7.67 (d, J = 8.19 Hz, 1H), 7.62 (s, 1H), 7.58 (m, 1H), 7.32 (d, J = 7.71 Hz, 1H), 7.27 (bs, 1H), 7.14 (m, 3H), 7.00 (d, J = 7.41 Hz, 1H), 6.66 (m, 1H), 5.26 (s, 2H), 4.15 (d, J = 4.26 Hz, 2H), 2.88 (s, 3H). | B |
| 23 | 2.44 | (M + H)+ = 415 (M − H)− = 413 | 9.71 (s, 1H), 8.68 (s, 1H), 7.70 (d, J = 8.10 Hz, 1H), 7.62 (s, 1H), 7.57 (bs, 1H), 7.42 (t, J = 4.71 Hz, 1H), 7.31 (m, 2H), 7.17 (m, 2H), 6.99 (d, J = 7.56 Hz, 1H), 4.14 (s, 2H), 3.85 (s, 3H), 3.72 (s, 3H), 2.87 (s, 3H). | B |
| 24 | 2.43 | (M + H)+ = 415 (M − H)− = 413 | 9.57 (s, 1H), 8.62 (s, 1H), 7.99 (d, J = 8.37 Hz, 1H), 7.68 (d, J = 7.62 Hz, 1H), 7.62 (s, 1H), 7.54 (m, 1H), 7.46 (s, 1H), 7.30 (t, J = 7.80 Hz, 1H), 6.98 (d, J = 7.44 Hz, 1H), 6.66 (m, 2H), 4.14 (d, J = 5.94 Hz, 2H), 3.90 (s, 3H), 3.82 (s, 3H), 2.87 (s, 3H). | B |
| 25 | 2.75 | (M + H)+ = 419 (M − H)− = 417 | 9.67 (s, 1H), 8.67 (s, 1H), 7.98 (d, J = 8.34 Hz, 1H), 7.69 (d, J = 7.92 Hz, 1H), 7.62 (s, 1H), 7.55 (m, 1H), 7.44 (s, 1H), 7.33 (t, J = 7.80 Hz, 1H), 7.25 (s, 1H), 7.13 (d, J = 8.01 Hz, 1H), 6.99 (d, J = 7.23 Hz, 1H), 4.14 (d, J = 5.97 Hz, 2H), 3.93 (s, 3H), 2.88 (s, 3H). | B |

TABLE 1-continued

| No. | Ret. Time (min) | ESI-MS | NMR | CDK9 inhibitory range |
|---|---|---|---|---|
| 26 | 2.34 | (M + H)+ = 399 (M − H)− = 397 | 9.62 (s, 1H), 8.66 (s, 1H), 7.77 (s, 1H), 7.69 (d, J = 8.25 Hz, 1H), 7.62 (s, 1H), 7.55 (bs, 1H), 7.44 (s, 1H), 7.30 (t, J = 7.74 Hz, 1H), 7.24 (d, J = 8.34 Hz, 1H), 7.05 (d, J = 8.43 Hz, 1H), 6.99 (d, J = 7.47 Hz, 1H), 4.14 (s, 2H), 3.85 (s, 3H), 2.87 (s, 3H), 2.29 (s, 3H). | C |
| 27 | 2.81 | (M + H)+ = 399 (M − H)− = 397 | 9.82 (s, 1H), 8.69 (s, 1H), 7.74 (d, J = 7.98 Hz, 1H), 7.68 (m, 2H), 7.54 (t, J = 5.91 Hz, 1H), 7.50 (s, 1H), 7.30 (t, J = 7.68 Hz, 1H), 6.99 (m, 3H), 6.20 (s, 2H), 4.14 (d, J = 5.88 Hz, 2H), 2.88 (s, 3H). | B |
| 28 | 2.67 | (M + H)+ = 401 (M − H)− = 399 | 9.74 (s, 1H), 8.68 (s, 1H), 7.67 (d, J = 7.58 Hz, 1H), 7.58 (m, 2H), 7.43 (m, 3H), 7.33 (d, J = 7.80 Hz, 1H), 7.25 (t, J = 6.78 Hz, 1H), 6.99 (m, 2H), 4.14 (d, J = 5.46 Hz, 2H), 2.87 (s, 3H), 2.41 (s, 3H). | B |
| 29 | 2.79 | (M + H)+ = 417 (M − H)− = 415 | 9.83 (s, 1H), 8.69 (s, 1H), 8.19 (d, J = 8.16 Hz, 1H), 7.80 (m, 2H), 7.68 (m, 2H), 7.60 (s, 1H), 7.57 (s, 1H), 7.33 (t, J = 7.58 Hz, 1H), 7.16 (s, 1H), 7.03 (d, J = 7.41 Hz, 1H), 4.16 (s, 2H), 2.90 (s, 3H), 2.88 (s, 3H). | C |
| 30 | 3.84 | (M + H)+ = 545 (M − H)− = 543 | 9.70 (s, 1H), 8.63 (s, 1H), 7.57 (m, 7H), 7.28 (m, 3H), 6.97 (m, 4H), 5.32 (s, 2H), 4.14 (d, J = 6.12 Hz, 2H), 2.87 (s, 3H). | D |
| 31 | 2.70 | (M + H)+ = 413 (M − H)− = 411 | 9.60 (s, 1H), 8.66 (s, 1H), 7.90 (d, J = 7.62 Hz, 1H), 7.67 (d, J = 8.19 Hz, 1H), 7.56 (s, 1H), 7.40 (m, 2H), 7.31 (t, J = 7.74 Hz, 1H), 7.13 (d, J = 8.31 Hz, 1H), 7.03 (m, 2H), 4.14 (s, 2H), 4.02 (t, J = 6.65 Hz, 2H), 2.87 (s, 3H), 1.75 (m, 2H), 0.92 (t, J = 7.38 Hz, 3H). | B |
| 32 | 0.46-1.96 | (M + H)+ = 345 (M − H)− = 343 | 13.19 (s, 1H), 9.55 (s, 1H), 8.56 (s, 1H), 8.3 (bs, 1H), 8.0 (bs, 1H), 7.58 (m, 3H), 7.30 (t, J = 7.98 Hz, 1H), 6.99 (d, J = 7.56 Hz, 1H), 6.96 (s, 1H), 4.15 (d, J = 6.12 Hz, 2H), 2.89 (s, 3H) | B |
| 33 | 2.68 | (M + H)+ = 313 (M − H)− = 311 | 9.85 (s, 1H), 8.45 (s, 1H), 7.57 (d, J = 8.37 Hz, 2H), 7.48 (t, J = 6.12 Hz, 1H), 7.31 (d, J = 8.37 Hz, 2H), 6.77 (s, 1H), 4.11 (d, J = 6.27 Hz, 2H), 2.83 (s, 3H). | D |
| 34 | 2.17 | (M + H)+ = 385 (M − H)− = 383 | 9.62 (s, 1H), 8.68 (s, 1H), 7.94 (dd, J1 = 7.65 Hz, J2 = 7.47 Hz, 1H), 7.68 (d, J = 8.43 Hz, 2H), 7.45 (m, 3H), 7.61 (d, J = 8.40 Hz, 2H), 7.18 (d, J = 8.31 Hz, 1H), 7.08 (t, J = 7.41 Hz, 1H), 4.11 (d, J = 6.21 Hz, 2H), 3.90 (s, 3H), 2.85 (s, 3H). | B |
| 35 | 2.88 | (M + H)+ = 461 (M − H)− = 459 | 9.59 (s, 1H), 8.69 (s, 1H), 7.84 (d, J = 6.60 Hz, 1H), 7.60 (d, J = 8.28 Hz, 2H), 7.37 (m, 10H), 7.20 (d, J = 8.34 Hz, 1H), 7.07 (t, J = 7.44 Hz, 1H), 5.26 (s, 2H), 4.11 (s, 2H), 2.84 (s, 3H). | A |
| 36 | 2.93 | (M + H)+ = 479 (M − H)− = 477 | 9.58 (s, 1H), 8.69 (s, 1H), 7.84 (d, J = 7.59 Hz, 1H), 7.59 (d, J = 8.19 Hz, 2H), 7.45 (m, 7H), 7.29 (d, J = 8.22 Hz, 2H), 7.20 (m, 3H), 7.08 (t, J = 7.44 Hz, 1H), 5.24 (s, 2H), 4.12 (s, 2H), 2.84 (s, 3H). | B |
| 37 | 2.45 | (M + H)+ = 399 (M − H)− = 397 | 9.57 (s, 1H), 8.67 (s, 1H), 7.94 (d, J = 6.45 Hz, 1H), 7.64 (d, J = 8.34 Hz, 2H), 7.44 (m, 3H), 7.32 (d, J = 8.31 Hz, 2H), 7.15 (d, J = 8.28 Hz, 1H), 7.06 (t, J = 7.50 Hz, 1H), 4.15 (m, 4H), 2.85 (s, 3H), 1.38 (t, J = 6.90 Hz, 3H). | A |
| 38 | 2.55 | (M + H)+ = 403 (M − H)− = 401 | 9.69 (s, 1H), 8.69 (s, 1H), 7.77 (dd, J1 = 9.96 Hz, J2 = 3.12 Hz, 1H), 7.68 (d, J = 8.28 Hz, 2H), 7.53 (s, 1H), 7.48 (bs, 1H), 7.32 (d, J = 8.13 Hz, 2H), 7.28 (m, 1H), 7.20 (m, 1H), 4.12 (s, 2H), 3.90 (s, 3H), 2.85 (s, 3H). | B |
| 39 | 2.42 | (M + H)+ = 403 (M − H)− = 401 | 9.63 (s, 1H), 8.69 (s, 1H), 8.03 (m, 1H), 8.03 (dd, J1 = 8.52 Hz, J2 = 7.47 Hz, 1H), 7.68 (d, J = 8.40 Hz, 2H), 7.48 (t, J = 6.15 Hz, 1H), 7.43 (s, 1H), 7.31 (d, J = 8.40 Hz, 2H), 7.09 (dd, J1 = 11.43 Hz, J2 = 2.25 Hz, 1H), 6.91 (m, 1H), 4.12 (d, J = 6.21 Hz, 2H), 2.84 (s, 3H). | A |

TABLE 1-continued

| No. | Ret. Time (min) | ESI-MS | NMR | CDK9 inhibitory range |
|---|---|---|---|---|
| 40 | 3.09 | (M + H)+ = 447 (M − H)− = 445 | 9.64 (s, 1H), 8.68 (s, 1H), 8.03 (d, J = 7.71 Hz, 1H), 7.59 (d, J = 8.16 Hz, 2H), 7.49 (t, J = 6.84 Hz, 1H), 7.38 (m, 3H), 7.32 (m, 3H), 7.13 (t, J = 7.26 Hz, 1H), 6.99 (m, 3H), 4.10 (d, J = 5.61 Hz, 2H), 2.84 (s, 3H). | B |
| 41 | 2.57 | (M + H)+ = 401 (M − H)− = 399 | 9.70 (s, 1H), 8.70 (s, 1H), 7.67 (d, J = 8.32 Hz, 2H), 7.45 (m, 4H), 7.30 (m, 3H), 6.97 (s, 1H), 4.12 (d, J = 6.15 Hz, 2H), 2.85 (s, 3H), 2.46 (s, 3H). | B |
| 42 | 3.01 | (M + H)+ = 391 (M − H)− = 389 | 9.78 (s, 1H), 8.72 (s, 1H), 8.17 (dd, J1 = 8.76 Hz, J2 = 1.80 Hz, 1H), 7.68 (d, J = 8.43 Hz, 2H), 7.44 (m, 2H), 7.32 (d, J = 8.43 Hz, 2H), 7.25 (m, 2H), 4.12 (d, J = 6.21 Hz, 2H), 2.85 (s, 3H). | D |
| 43 | 3.00 | (M + H)+ = 423 (M − H)− = 421 | 9.75 (s, 1H), 8.68 (s, 1H), 7.86 (d, J = 7.77 Hz, 1H), 7.79 (t, J = 7.41 Hz, 1H), 9.69 (m, 1H), 7.67 (d, J = 8.43 Hz, 2H), 7.57 (d, J = 7.32 Hz, 1H), 7.49 (t, J = 6.15 Hz, 1H), 7.32 (d, J = 8.43 Hz, 3H), 6.83 (s, 1H), 4.12 (d, J = 6.24 Hz, 2H), 2.85 (s, 3H). | D |
| 44 | 2.68 | (M + H)+ = 373 (M − H)− = 371 | 9.77 (s, 1H), 8.74 (s, 1H), 8.09 (dt, J1 = 9.57 Hz, J2 = 1.68 Hz, 1H), 7.69 (d, J = 8.46 Hz, 2H), 7.51 (m, 2H), 7.63 (m, 1H), 7.32 (d, J = 8.46 Hz, 2H), 7.28 (s, 1H), 4.12 (d, J = 6.24 Hz, 2H), 2.85 (s, 3H). | C |
| 45 | 2.46 | (M + H)+ = 355 (M − H)− = 353 | 9.68 (s, 1H), 8.71 (s, 1H), 8.02 (m, 2H), 7.69 (d, J = 8.40 Hz, 2H), 7.52 (m, 4H), 7.32 (d, J = 8.10 Hz, 2H), 7.23 (s, 1H), 4.12 (d, J = 6.21 Hz, 2H), 2.85 (s, 3H). | C |
| 46 | 0.46-2.02 | (M + H)+ = 370 (M − H)− = 368 | 10.95 (bs, 1H), 8.83 (s, 1H), 7.69 (d, J = 8.43 Hz, 2H), 7.54 (m, 4H), 7.38 (d, J = 8.43 Hz, 2H), 7.29 (s, 1H), 7.27 (m, 1H), 4.50 (bs, 3H), 4.15 (d, J = 3.99 Hz, 2H), 2.87 (s, 3H). | C |
| 47 | 2.64 | (M + H)+ = 385 (M − H)− = 383 | 9.68 (s, 1H), 8.71 (s, 1H), 8.02 (m, 2H), 7.69 (d, J = 8.40 Hz, 2H), 7.59 (s, 1H), 7.56 (m, 1H), 7.47 (m, 2H), 7.32 (d, J = 8.37 Hz, 2H), 7.26 (s, 1H), 7.08 (m, 1H), 4.12 (d, J = 6.24 Hz, 2H), 3.84 (s, 3H), 2.85 (s, 3H). | C |
| 48 | 2.76 | (M + H)+ = 431 (M − H)− = 429 | 9.57 (s, 1H), 8.65 (s, 1H), 7.80 (t, J = 7.68 Hz, 1H), 7.62 (d, J = 8.34 Hz, 2H), 7.49 (bs, 1H), 7.42 (s, 1H), 7.32 d, J = 8.37 Hz, 2H), 7.07 (dd, J1 = 11.67 Hz, J2 = 2.22 Hz, 1H), 6.87 (dt, J1 = 10.62 Hz, J2 = 2.19 Hz, 1H), 4.77 (m, 1H), 4.12 (s, 2H), 2.85 (s, 3H), 1.31 (d, J = 5.97 Hz, 6H). | A |
| 49 | 2.92 | (M + H)+ = 479 (M − H)− = 477 | 9.60 (s, 1H), 8.70 (s, 1H), 7.83 (d, J = 7.35 Hz, 1H), 7.62 (d, J = 8.01 Hz, 2H), 7.23 (m, 11H), 5.28 (s, 2H), 4.11 (s, 2H), 2.84 (s, 3H). | B |
| 50 | 2.86 | (M + H)+ = 491 (M − H)− = 489 | 9.55 (s, 1H), 8.67 (s, 1H), 7.82 (d, J = 7.44 Hz, 1H), 7.57 (d, J = 7.95 Hz, 2H), 7.47 (t, J = 5.70 Hz, 1H), 7.41 (s, 1H), 7.38 (bs, 1H), 7.34 (d, J = 8.49 Hz, 2H), 7.28 (d, J = 8.13 Hz, 2H), 7.19 (d, J = 8.31 Hz, 1H), 7.05 (t, J = 7.44 Hz, 1H), 6.87 (d, J = 8.13 Hz, 2H), 5.16 (s, 2H), 4.10 (d, J = 6.00 Hz, 2H), 3.71 (s, 3H), 2.83 (s, 3H). | B |
| 51 | 2.89 | (M + H)+ = 427 (M − H)− = 425 | 9.55 (s, 1H), 8.66 (s, 1H), 7.85 (d, J = 7.56 Hz, 1H), 7.60 (d, J = 8.25 Hz, 2H), 7.44 (m, 2H), 7.36 (s, 1H), 7.29 (d, J = 8.28 Hz, 2H), 7.12 (d, J = 8.34 Hz, 1H), 7.04 (t, J = 7.50 Hz, 1H), 4.10 (d, J = 6.21 Hz, 2H), 3.81 (d, J = 6.51 Hz, 2H), 2.84 (s, 3H), 2.03 (m, 1H), 0.90 (d, J = 6.63 Hz, 6H). | B |
| 52 | 2.16 | (M + H)+ = 356 (M − H)− = 354 | 9.75 (s, 1H), 9.17 (d, J = 1.98 Hz, 1H), 8.72 (s, 1H), 8.69 (d, J = 4.68 Hz, 1H), 8.34 (d, J = 6.39 Hz, 1H), 7.68 (d, J = 8.46 Hz, 2H), 7.55 (dd, J1 = 7.98 Hz, J2 = 4.80 Hz, 1H), 7.48 (t, J = 6.12 Hz, 1H), 7.31 (d, J = 8.40 Hz, 2H), 7.26 (s, 1H), 4.11 (d, J = 6.12 Hz, 2H), 2.84 (s, 3H). | C |

TABLE 1-continued

| No. | Ret. Time (min) | ESI-MS | NMR | CDK9 inhibitory range |
|---|---|---|---|---|
| 53 | 2.64 | (M + H)+ = 413<br>(M − H)− = 411 | 9.54 (s, 1H), 8.66 (s, 1H), 7.90 (dd, J1 = 7.71 Hz, J2 = 1.59 Hz, 1H), 7.61 (d, J = 8.40 Hz, 2H), 7.47 (t, J = 6.18 Hz, 1H), 7.09 (m, 2H), 7.31 (d, J = 8.43 Hz, 2H), 7.13 (d, J = 8.28 Hz, 1H), 7.04 (t, J = 7.41 Hz, 1H), 4.11)d, J = 6.21 Hz, 2H), 4.02 (t, J = 6.54 Hz, 2H), 2.84 (s, 3H), 1.75 (m, 1H), 0.92 (t, J = 7.32 Hz, 3H). | A |
| 54 | 2.69 | (M + H)+ = 419<br>(M − H)− = 417 | 9.64 (s, 1H), 8.66 (s, 1H), 7.99 (d, J = 11.37 Hz, 1H), 7.66 (d, J = 8.46 Hz, 2H), 7.47 (t, J = 6.24 Hz, 1H), 7.42 (s, 1H), 7.30 (d, J = 8.46 Hz, 2H), 7.25 (d, J = 1.83 Hz, 1H), 7.13 (dd, J1 = 8.40 Hz, J2 = 1.77 Hz, 1H), 4.10 (d, J = 6.24 Hz, 2H), 3.92 (s, 3H), 2.83 (s, 3H). | A |
| 55 | 2.37 | (M + H)+ = 415<br>(M − H)− = 413 | 9.66 (s, 1H), 8.68 (s, 1H), 7.67 (d, J = 8.43 Hz, 2H), 7.43 (m, 2H), 7.32 (s, 1H), 7.30 (d, J = 8.22 Hz, 2H), 7.16 (d, J = 1.59 Hz, 1H), 7.15 (s, 1H), 4.10 (d, J = 6.24 Hz, 2H), 3.85 (s, 3H), 3.72 (s, 3H), 2.83 (s, 3H). | B |
| 56 | 2.62 | (M + H)+ = 413<br>(M − H)− = 411 | 9.56 (s, 1H), 8.67 (s, 1H), 7.91 (d, J = 6.78 Hz, 1H), 7.63 (d, J = 8.28 Hz, 2H), 7.49 (t, J = 5.79 Hz, 1H), 7.45 (s, 1H), 7.40 (t, J = 7.35 Hz, 1H), 7.32 (d, J = 8.28 Hz, 2H), 7.16 (d, J = 8.28 Hz, 1H), 7.04 (t, J = 7.47 Hz, 1H), 4.71 (m, 1H), 4.12 (d, J = 6.00 Hz, 2H), 2.85 (s, 3H), 1.30 (d, J = 4.86 Hz, 6H). | A |
| 57 | 2.46 | (M + H)+ = 385<br>(M − H)− = 383 | 9.60 (s, 1H), 8.66 (s, 1H), 7.99 (d, J = 8.55 Hz, 2H), 7.68 (d, J = 8.19 Hz, 2H), 7.48 (t, J = 5.82 Hz, 1H), 7.31 (d, J = 8.22 Hz, 2H), 7.16 (s, 1H), 7.08 (d, J = 8.70 Hz, 2H), 4.12 (d, J = 5.73 Hz, 2H), 3.83 (s, 3H), 2.85 (s, 3H). | B |
| 58 | 0.46-1.89 | (M + H)+ = 345<br>(M − H)− = 343 | 13.19 (s, 1H), 9.52 (s, 1H), 8.56 (s, 1H), 8.3 (bs, 1H), 8.0 (bs, 1H), 7.65 (d, J = 8.37 Hz, 2H), 7.48 (t, J = 5.88 Hz, 1H), 7.29 (d, J = 8.37 Hz, 2H), 6.93 (s, 1H), 4.11 (d, J = 5.88 Hz, 2H), 2.84 (s, 3H) | D |
| 59 | 2.57 | (M + H)+ = 351<br>(M − H)− = 349 | 11.3 (bs, 1H), 9.88 (s, 1H), 8.37 (s, 1H), 7.56 (s, 1H), 7.55 (d, J = 7.56 Hz, 1H), 7.44 (bs, 1H), 7.32 (t, J = 7.80 Hz, 1H), 7.15 (m, 2H), 7.10 (d, J = 7.56 Hz, 1H), 6.91 (m, 2H), 4.54 (d, J = 2.76 Hz, 2H) | D |
| 60 | 0.45-1.95-2.27 | (M + H)+ = 423<br>(M − H)− = 421 | 11.8 (bs, 1H), 9.66 (s, 1H), 8.57 (s, 1H), 8.15 (bs, 1H), 7.93 (d, J = 6.33 Hz, 1H), 7.73 (s, 1H), 7.66 (d, J = 8.10 Hz, 1H), 7.45 (m, 2H), 7.32 (t, J = 7.86 Hz, 1H), 7.25 (m, 2H), 7.17 (d, J = 8.28 Hz, 1H), 7.09-7.01 (m, 4H), 4.60 (s, 2H), 3.88 (s, 3H) | B |
| 61 | 0.45-2.30-2.43 | (M + H)+ = 441<br>(M − H)− = 439 | 12.5 (bs, 1H), 9.71 (s, 1H), 9.85 (bs, 1H), 8.53 (s, 1H), 8.01 (t, J = 7.98 Hz, 1H), 7.77 (s, 1H), 7.67-7.54 (m, 2H), 7.44 (s, 1H), 7.37-7.30 (m, 2H), 7.15-7.05 (m, 4H), 6.90 (t, J = 8.28 Hz 1H), 4.64 (d, J = 3.69 Hz, 2H), 3.90 (s, 3H) | B |
| 62 | 0.45-2.43-2.54 | (M + H)+ = 441<br>(M − H)− = 439 | 12.1 (bs, 1H), 9.76 (s, 1H), 8.57 (s, 1H), 8.42 (bs, 1H), 7.78-7.74 (m, 2H), 7.67 (d, J = 8.25 Hz, 1H), 7.54 (s, 1H), 7.35 (d, J = 7.83 Hz, 1H), 7.30-7.26 (m, 3H), 7.19 (m, 2H), 7.07 (m, 2H), 4.61 (s, 2H), 3.88 (s, 3H) | B |
| 63 | 2.56 | (M + H)+ = 236<br>(M − H)− = 234 | 9.83 (s, 1H), 8.40 (d, J = 8.13 Hz, 2H), 7.67-7.65 (m, 1H), 7.61 (d, J = 7.98 Hz, 1H), 7.53-7.49 (m, 1H), 7.42 (s, 1H), 7.33 (t, J = 7.83 Hz, 1H), 7.25-7.17 (m, 2H), 7.02 (d, J = 7.56 Hz, 1H), 6.74 (s, 1H), 5.52 (s, 2H) | C |
| 64 | 2.34 | (M + H)+ = 408<br>(M − H)− = 406 | 9.60 (s, 1H), 8.64 (s, 1H), 8.40 (s, 1H), 7.93 (d, J = 7.44 Hz, 1H), 7.73 (d, J = 8.16 Hz, 1H), 7.67 (d, J = 5.85 Hz, 1H), 7.53-7.40 (m, 4H), 7.31 (t, J = 7.74 Hz, 1H), 7.23-7.15 (m, 3H), 7.07 (t, J = 7.38 Hz, 1H), 6.94 (d, J = 7.71 Hz, 1H), 5.52 (s, 2H), 3.87 (s, 3H) | A |

TABLE 1-continued

| No. | Ret. Time (min) | ESI-MS | NMR | CDK9 inhibitory range |
|---|---|---|---|---|
| 65 | 2.49 | (M + H)+ = 426 (M − H)− = 424 | 9.61 (s, 1H), 8.63 (s, 1H), 8.39 (s, 1H), 8.01 (t, J = 7.92 Hz, 1H), 7.72 (d, J = 8.22 Hz, 1H), 7.66 (d, J = 8.46 Hz, 1H), 7.51 (m, 2H), 7.38 (s, 1H), 7.31 (t, J = 7.83 Hz, 1H), 7.22-7-19 (m, 2H), 7.08 (dd, 3J = 11.37 Hz, 4J = 1.77 Hz, 1H), 6.96-6.87 (m, 2H), 5.51 (s, 2H), 3.90 (s, 3H) | A |
| 66 | 2.60 | (M + H)+ = 426 (M − H)− = 424 | 9.67 (s, 1H), 8.64 (s, 1H), 8.39 (s, 1H), 7.78-7.66 (m, 3H), 7.52-7.48 (m, 3H), 7.34-7.28 (m, 2H), 7.22-7.17 (m, 3H), 9.96 (d, J = 7.44 Hz, 1H), 5.52 (s, 2H), 3.87 (s, 3H) | A |
| 67 | 3.83 | (M + H)+ = 365 (M − H)− = 363 | 9.83 (s, 1H), 8.34 (s, 1H), 7.88 (m, 4H), 7.63 (d, J = 8.04 Hz, 1H), 7.43 (s, 1H), 7.30 (t, J = 7.86 Hz, 1H), 7.02 (d, J = 7.62 Hz, 1H), 6.75 (s, 1H), 4.76 (s, 1H). | D |
| 68 | 3.05 | (M + H)+ = 437 (M − H)− = 435 | 9.61 (s, 1H), 8.58 (s, 1H), 7.90 (m, 5H), 7.76 (d, J = 8.16 Hz, 1H), 7.54 (s, 1H), 7.44 (t, J = 8.19 Hz, 1H), 7.42 (s, 1H), 7.30 (t, J = 7.65 Hz, 1H), 7.16 (d, J = 8.43 Hz, 1H), 7.07 (t, J = 7.50 Hz, 1H), 6.98 (d, J = 7.44 Hz, 1H), 4.78 (s, 2H), 3.88 (s, 3H). | A |
| 69 | 0.45-1.68 | (M + H)+ = 307 | 11.62 (bs, 1H), 8.89 (s, 1H), 8.55 (bs, 3H), 7.80 (s, 1H), 7.75 (d, J = 8.34 Hz, 1H), 7.70 (d, J = 7.53 Hz, 1H), 7.62 (t, J = 8.34 Hz, 1H), 7.49 (m, 2H), 7.38 (d, J = 7.65 Hz, 1H), 7.28 (d, J = 8.40 Hz, 1H), 7.17 (t, J = 7.56 Hz, 1H), 4.04 (m, 2H), 3.92 (s, 3H). | A |
| 70 | 3.24 | (M + H)+ = 515 (M − H)− = 513 | 11.14 (s, 1H), 8.88 (s, 1H), 8.72 (t, J = 6.15 Hz, 1H), 7.70 (d, J = 6.33 Hz, 1H), 7.62 (t, J = 7.98 Hz, 1H), 7.52 (m, 4H), 7.49 (m, 1H), 7.34 (s, 1H), 7.30 (s, 1H), 7.28 (m, 1H), 7.18 (t, J = 7.56 Hz, 1H), 7.08 (d, J = 7.65 Hz, 1H), 4.18 (d, J = 5.88 Hz, 2H), 3.91 (s, 3H). | B |
| 71 | 2.76 | (M + H)+ = 413 (M − H)− = 411 | 9.65 (s, 1H), 8.68 (s, 1H), 7.95 (dd, J1 = 7.71 Hz, J2 = 1.68 Hz, 1H), 7.70 (d, J = 7.83 Hz, 1H), 7.64 (s, 1H), 7.60 (t, J = 6.42 Hz, 1H), 7.45 (m, 2H), 7.32 (t, J = 7.83 Hz, 1H), 7.18 (d, J = 8.31 Hz, 1H), 7.08 (t, J = 7.41 Hz, 1H), 7.00 (d, J = 7.05 Hz, 1H), 4.13 (d, J = 6.27 Hz, 2H), 3.90 (s, 3H), 2.92 (t, J = 7.62 Hz, 2H), 1.66 (m, 2H), 0.92 (t, J = 7.47 Hz, 3H). | A |
| 72 | 3.15 | (M + H)+ = 465 (M − H)− = 463 | 11.05 (bs, 1H), 8.88 (s, 1H), 8.28 (t, J = 6.18 Hz, 1H), 7.86 (dd, J = 8.82 Hz, J2 = 5.28 Hz, 2H), 7.70 (d, J = 7.59 Hz, 1H), 7.61 (m, 2H), 7.52 (s, 1H), 7.37 (m, 3H), 7.28 (d, J = 8.34 Hz, 1H), 7.17 (t, J = 7.53 Hz, 1H), 7.07 (d, J = 7.98 Hz, 1H), 4.02 (d, J = 6.21 Hz, 2H), 3.91 (s, 3H), | B |
| 73 | 2.98 | (M + H)+ = 453 (M − H)− = 451 | 11.33 (s, 1H), 8.91 (s, 1H), 8.47 (t, J = 6.18 Hz, 1H), 7.92 (d, J = 4.95 Hz, 1H), 7.68-7.56 (m, 5H), 7.39 (d, J = 7.77 Hz, 1H), 7.35 (s, 1H), 7.28 (d, J = 8.40 Hz, 1H), 7.20-7.10 (m, 3H), 4.08 (d, J = 6.18 Hz, 2H), 3.90 (s, 3H) | B |
| 74 | 3.08 | (M + H)+ = 461 (M − H)− = 459 | 9.65 (s, 1H), 8.68 (s, 1H), 7.95 (d, J = 6.48 Hz, 1H), 7.72-7.67 (m, 2H), 7.61 (s, 1H), 7.46-7.28 (m, 8H), 7.18 (d, J = 8.28 Hz, 1H), 7.08 (t, J = 8.28 Hz, 1H), 6.98 (d, J = 7.62 Hz, 1H), 4.33, (s, 2H), 4.09 (s, 2H), 3.90 (s, 3H) | B |
| 75 | 0.55-2.04-2.30 | (M + H)+ = 371 (M − H)− = 369 | 9.92 (bs, 1H), 9.59 (s, 1H), 8.63 (s, 1H), 7.89 (d, J = 6.84 Hz, 2H), 7.63 (m, 3H), 7.31 (m, 1H), 7.14 (s, 1H), 7.01 (m, 1H), 6.89 (d, J = 6.87 Hz, 2H), 4.16 (s, 2H), 2.89 (s, 3H). | A |
| 76 | 0.54-1.89-2.26 | (M + H)+ = 371 (M − H)− = 369 | 9.93 (bs, 1H), 9.56 (s, 1H), 8.63 (s, 1H), 7.89 (m, 2H), 7.66 (bs, 2H), 7.48 (bs, 1H), 7.31 (bs, 2H), 7.10 (s, 1H), 6.89 (m, 2H), 4.12 (s, 2H), 2.84 (s, 3H). | B |
| 77 | 0.45-2.56-2.73 | (M + H)+ = 469 (M − H)− = 467 | 10.80 (bs, 1H), 9.55 (s, 1H), 8.60 (s, 1H), 7.98 (m, 1H), 7.64 (d, J = 5.76 Hz, 1H), 7.58 (s, 1H), 7.40 (m, 1H), 7.29 (m, 1H), 7.08 (m, 5H), 6.86 (m, 3H), 4.74 (m, 1H), 4.53 (m, 2H), 1.29 (m, 6H). | A |
| 78 | 0.44-2.09 | (M + H)+ = 409 (M − H)− = 407 | 10.80 (bs, 1H), 9.90 (s, 1H), 9.53 (s, 1H), 8.56 (s, 1H), 7.86 (bs, 2H), 7.63 (bs, 2H), 7.00 (m, 10H), 4.52 (s, 2H). | B |

TABLE 1-continued

| No. | Ret. Time (min) | ESI-MS | NMR | CDK9 inhibitory range |
|---|---|---|---|---|
| 79 | 0.45-2.10-2.37 | (M + H)+ = 426 (M − H)− = 424 | 9.62 (s, 1H), 8.40 (s, 1H), 7.66 (m, 2H), 7.46 (m, 3H), 7.31 (t, J = 7.77 Hz, 1H), 7.20 (m, 2H), 7.00 (t, J = 6.93 Hz, 2H), 6.91 (t, J = 8.73 Hz, 1H), 6.75 (s, 1H), 5.52 (s, 2H), 3.75 (s, 3H). | A |
| 80 | 2.73 | (M + H)+ = 436 (M − H)− = 434 | 9.55 (bs, 1H), 8.63 (bs, 1H), 8.40 (bs, 1H), 7.90 (bs, 1H), 7.67 (bs, 2H), 7.51 (bs, 2H), 7.40 (bs, 2H), 7.33 (m. 1H), 7.19 (m, 3H), 6.99 (m, 2H), 5.51 (s, 2H), 4.67 (m. 1H), 1.25 (bs, 6H). | A |
| 81 | 2.90 | (M + H)+ = 454 (M − H)− = 452 | 9.55 (s, 1H), 8.61 (s, 1H), 8.40 (s, 1H), 7.98 (m, 1H), 7.66 (bs, 2H), 7.50 (bs, 2H), 7.34 (m, 2H), 7.19 (bs, 2H), 7.05 (d, J = 11.73 Hz, 1H), 6.99 (bs, 1H), 6.86 (m, 1H), 5.51 (s, 2H), 4.73 (m, 1H), 1.26 (bs, 6H). | A |
| 82 | 0.55-2.03-2.26 | (M + H)+ = 394 (M − H)− = 392 | 9.95 (bs, 1H), 9.54 (s, 1H), 8.59 (s, 1H), 8.41 (s, 1H), 7.85 (d, J = 6.87 Hz, 2H), 7.67 (bs, 2H), 7.52 (s, 2H), 7.25 (m, 3H), 7.05 (s, 1H), 6.97 (m, 1H), 6.88 (d, J = 6.84 Hz, 2H), 5.52 (s, 2H). | B |
| 83 | 0.47-2.11-2.31 | (M + H)+ = 394 (M − H)− = 392 | 9.73 (bs, 1H), 9.63 (s, 1H), 8.63 (m, 1H), 8.43 (m, 1H), 7.68 (m, 2H), 7.54 (s, 2H), 7.40 (m, 3H), 7.30 (m, 1H), 7.21 (m, 1H), 7.11 (s, 1H), 6.99 (m, 1H), 6.89 (m, 1H), 5.52 (s, 2H). | C |
| 84 | 0.44-2.92 | (M + H)+ = 429 (M − H)− = 427 | 11.22 (bs, 1H), 9.17 (bs, 1H), 8.85 (s, 1H), 8.01 (bs, 2H), 7.64 (m, 4H), 7.28 (m, 7H), 4.50 (s, 2H), 3.90 (s, 3H). | B |
| 85 | 0.44-2.77-2 94 | (M + H)+ = 444 (M − H)− = 442 | 9.61 (s, 1H), 8.66 (s, 1H), 8.59 (s, 1H), 7.96 (d, J = 1.71 Hz, 1H), 7.68 (d, J = 6.81 Hz, 1H), 7.58 (s, 1H), 7.43 (m, 4H), 7.30 (t, J = 7.68 Hz, 1H), 7.17 (d, J = 8.07 Hz, 1H), 7.06 (m, 3H), 6.96 (d, J = 7.26 Hz, 1H), 6.60 (bs, 1H), 4.30 (s, 2H), 3.89 (s, 3H). | C |
| 86 | 2.43 | (M + H)+ = 336 (M − H)− = 334 | 9.88 (s, 1H), 8.44 (s, 1H), 8.40 (s, 1H), 7.65 (m, 1H), 7.54 (m, 3H), 7.32 (d, J = 8.34 Hz, 2H), 7.20 (m, 2H), 6.77 (s, 1H), 5.46 (s, 2H). | D |
| 87 | 0.46-1.99-2.29 | (M + H)+ = 408 (M − H)− = 406 | 9.62 (s, 1H), 8.66 (s, 1H), 8.39 (s, 1H), 9.94 (d, J = 7.41 Hz, 1H), 7.67 (m, 3H), 7.54 (d, J = 6.90 Hz, 1H), 7.44 (m, 2H), 7.32 (d, J = 8.28 Hz, 2H), 7.20 (m, 3H), 7.07 (t, J = 7.53 Hz, 1H), 5.45 (s, 2H), 3.87 (s, 3H). | B |
| 88 | 2.77 | (M + H)+ = 454 (M − H)− = 452 | 9.56 (s, 1H), 8.62 (s, 1H), 8.40 (s, 1H), 7.98 (m, 1H), 7.64 (m, 4H), 7.40 (s, 1H), 7.34 (m, 2H), 7.20 (m, 2H), 7.07 (d, J = 10.65 Hz, 1H), 6.84 (m, 1H), 5.46 (s, 2H), 4.71 (m, 1H), 1.25 (d, J = 1.41 Hz, 6H). | B |
| 89 | 0.44-2.10 | (M + H)+ = 394 (M − H)− = 392 | 9.92 (bs, 1H), 9.56 (s, 1H), 8.60 (s, 1H), 8.39 (s. 1H), 7.87 (d, J = 8.55 Hz, 2H), 7.65 (m, 3H), 7.54 (d, J = 7.58 Hz, 1H), 7.31 (d, J = 8.31 Hz, 2H), 7.20 (m, 2H), 7.09 (s, 1H), 6.87 (d, J = 8.64 Hz, 2H), 5.45 (s, 2H). | B |
| 90 | 4.47 | (M + H)+ = 335 (M − H)− = 333 | 9.81 (s, 1H), 8.42 (m, 1H), 7.57 (m, 2H), 7.44 (m, 2H), 7.27 (m, 2H), 7.10 (m, 1H), 7.04 (m, 1H), 6.92 (m, 1H), 6.73 (m, 1H), 6.49 (s, 1H), 5.44 (s, 2H). | D |
| 91 | 3.56 | (M + H)+ = 407 (M − H)− = 405 | 9.57 (s, 1H), 8.63 (s, 1H), 7.92 (dd, J1 = 7.68 Hz, J2 = 1.56 Hz, 1H), 7.69 (d, J = 8.28 Hz, 1H), 7.55 (d, J = 7.74 Hz, 1H), 7.45 (m, 5H), 7.28 (t, J = 7.86 Hz, 1H), 7.16 (d, J = 8.37 Hz, 1H), 7.05 (m, 3H), 6.84 (d, J = 7.65 Hz, 1H), 6.48 (d, J = 3.00 Hz, 1H), 5.42 (s, 2H), 3.87 (s, 3H). | C |
| 92 | 2.70 | (M + H)+ = 435 (M − H)− = 433 | 10.23 (s, 1H), 8.40 (s, 1H), 7.80 (s, 1H), 7.62 (m, 2H), 7.49 (s, 1H), 7.36 (m, 3H), 6.91 (m, 2H), 5.74 (s, 2H), 4.76 (s, 2H), 3.85 (s, 4H), 2.50 (s, 4H). | D |
| 93 | 0.45-2.30-2.47 | (M + H)+ = 507 (M − H)− = 505 | 9.56 (s, 1H), 8.59 (s, 1H), 7.91 (d, J = 6.75 Hz, 1H), 7.69 (m, 2H), 7.28 (m, 9H), 6.84 (d, J = 6.21 Hz, 1H), 5.61 (s, 2H), 3.86 (s, 3H), 3.77 (s, 2H), 3.40 (s, 4H), 2.40 (s, 4H). | C |

TABLE 1-continued

| No. | Ret. Time (min) | ESI-MS | NMR | CDK9 inhibitory range |
|---|---|---|---|---|
| 94 | 0.44-2.59 | (M + H)+ = 525 (M − H)− = 523 | 9.57 (s, 1H), 8.57 (s, 1H), 7.99 (bs, 1H), 7.65 (m, 2H), 7.29 (m, 6H), 7.07 (d, J = 10.44 Hz, 1H), 6.88 (m, 2H), 5.61 (s, 2H), 3.88 (s, 3H), 3.76 (s, 2H), 3.40 (s, 4H), 2.41 (s, 4H). | C |

A <0.1 μM (IC50)
B <1 μM (IC50)
C <10 μM (IC50)
D 10 μM (IC50)<

The invention claimed is:

1. A compound of general formula (I) and pharmaceutically acceptable salts and solvates thereof (I)

wherein
R$^1$ is halogen;
vinylene-aryl;
aryl, which is substituted with one or more substituent selected from the following group:
  alkoxy which is optionally substituted with one or more halogen or with aryl which is optionally substituted with one or more halogen, alkyl or alkoxy,
  halogen,
  alkyl which is optionally subsituted with one or more halogen or alkoxy,
  alkylaryloxy which is optionally substituted with alkoxy which is optionally substituted with one or more halogen,
  aminocarbonyl,
  amino, which is optionally substituted with one or two alkyl;
  alkylthio,
  alkylsulfinyl or alkylsulfonyl,
  aryloxy,
  hydroxyl;
group of formula (a)

(a)

wherein m is 1, 2 or 3 and R' is hydrogen, halogen, alkyl or alkoxy;
heteroaryl;
W is a
  group of formula (b)

(b)

wherein R$^2$ stands for
  alkyl, alkoxy or aryl, which groups are optionally substituted with one or more halogen,
  heteroaryl,
  benzyl, which is optionally substituted with one or more halogen, alkyl or alkoxy,
  amino, which is optionally substituted with one or two alkyl;
heteroaryl group, which is optionally substituted with a (CH2)k-heterocycloalkyl group, where k is 0, 1, 2 or 3;
NH—R$^3$, wherein R$^3$ is hydrogen, alkyl, alkoxy, aryl, aryloxy, heteroaryl, heteroaryloxy, aminoalkyl, aminoaryl or aminoheteroaryl, or R$^3$ is —CO-aryl, —CO—NH-aryl where the aryl is optionally substituted with one or more halogen; and
n is 1, 2, 3 or 4.

2. A compound according to claim 1, where the heteroaryl in the meaning of R$^1$ is 5- or 6-membered heteroaryl containing 1 or 2 N-atom.

3. A compound according to claim 1, where the heteroaryl in the meaning of R$^2$ is 5- or 6-membered heteroaryl containing 1 or 2 S-atom.

4. A compound according to claim 1, where the heteroaryl in the meaning of W is a fused bicyclic heteroaryl group containing at least one heteroatom selected from the group of N, O and S in one of the rings and the other ring is a benzene ring, optionally substituted with 1 or 2 oxo group in the nitrogen containing ring and with one or more halogen, alkyl or alkoxy in the benzene ring.

5. A compound according to claim 1, where the heteroaryl in the meaning of W is a 1-benzoimidazolyl group.

6. A compound according to claim 1, where the heterocycloalkyl substituent of the heteroaryl in the meaning of W is a saturated ring of 4 to 7 atoms, wherein 1 or 2 ring member(s) is/are selected from the group consisting of O, S and NR$^x$, where R$^x$ is hydrogen or alkyl.

7. A compound according to claim 1, where the heteroaryl in the meaning of R$^3$ is a bicyclic fused heteroaryl group containing at least one heteroatom selected from the group of N, O and S in one of the rings and the other ring is a benzene ring.

8. A compound according to claim 1, where R$^3$ is —CO-aryl or —CO—NH-aryl, where the aryl is optionally substituted with one or more halogen.

9. Pharmaceutical composition containing as active ingredient one or more compound(s) of general formula (I) according to claim 1 together with one or more pharmaceutical auxiliary material(s).

* * * * *